(12) United States Patent
Kasai et al.

(10) Patent No.: US 9,120,777 B2
(45) Date of Patent: Sep. 1, 2015

(54) HETEROCYCLIC COMPOUND

(71) Applicant: Takeda Pharmaceutical Company Limited, Chuo-ku, Osaka-shi, Osaka (JP)

(72) Inventors: Shizuo Kasai, Kanagawa (JP); Asato Kina, Kanagawa (JP); Hideki Hirose, Kanagawa (JP); Takeshi Yamasaki, Kanagawa (JP); Tohru Yamashita, Kanagawa (JP); Yoichi Nishikawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/525,593

(22) Filed: Oct. 28, 2014

(65) Prior Publication Data

US 2015/0119412 A1    Apr. 30, 2015

(30) Foreign Application Priority Data

Oct. 29, 2013 (JP) ................................. 2013-224093

(51) Int. Cl.
    *C07D 401/12*    (2006.01)
    *C07D 211/86*    (2006.01)
    *C07D 239/22*    (2006.01)

(52) U.S. Cl.
    CPC ............ *C07D 401/12* (2013.01); *C07D 211/86* (2013.01); *C07D 239/22* (2013.01)

(58) Field of Classification Search
    None
    See application file for complete search history.

(56) References Cited

U.S. PATENT DOCUMENTS

| | | |
|---|---|---|
| 2005/0245581 A1 | 11/2005 | Nagato et al. |
| 2006/0100249 A1 | 5/2006 | Smith |
| 2006/0178399 A1 | 8/2006 | Nishizawa et al. |
| 2009/0004195 A1 | 1/2009 | Vranic et al. |

FOREIGN PATENT DOCUMENTS

| | | |
|---|---|---|
| WO | WO 93/22310 A1 | 11/1993 |
| WO | WO 01/96308 A1 | 12/2001 |
| WO | WO 03/047577 A2 | 6/2003 |
| WO | WO 2004/080966 A1 | 9/2004 |
| WO | WO 2005/047249 A1 | 5/2005 |
| WO | WO 2008/019967 A2 | 2/2008 |
| WO | WO 2008/122510 A1 | 10/2008 |
| WO | WO 2008/148710 A2 | 12/2008 |
| WO | WO 2009/036117 A1 | 3/2009 |
| WO | WO 2010/129729 A1 | 11/2010 |
| WO | WO 2012/024183 A1 | 2/2012 |
| WO | WO 2012/069917 A1 | 5/2012 |
| WO | WO 2014/142363 A1 | 9/2014 |

OTHER PUBLICATIONS

U.S. Appl. No. 14/505,907, filed Oct. 3, 2014, Kasai et al.
Chisholm et al., "Somatostatin-28 regulates GLP-1 secretion via somatostatin receptor subtype 5 in rat intestinal cultures," Am. J. Physiol. Endocrinol. Metab., 2002, 283:E311-E317.
Li et al., "Oxidative Conversion of Isoxazolidines to Isoxazolines," J. Org. Chem., 1998, 63:366-369.
Patel, Y.C., "Molecular pharmacology of somatostatin receptor subtypes," J. Endocrinol Invest., 1997, 20:348-367.
Registry Compound No. 1381469-87-9, ACS on STN (American Chemical Society, Scientific & Technical Information Network), entered Jul. 4, 2012.
Registry Compound No. 1214501-97-9, ACS on STN (American Chemical Society, Scientific & Technical Information Network), entered Mar. 25, 2010.
Registry Compound No. 1214473-59-2, ACS on STN (American Chemical Society, Scientific & Technical Information Network), entered Mar. 25, 2010.

*Primary Examiner* — Timothy R Rozof
(74) *Attorney, Agent, or Firm* — Foley & Lardner LLP

(57) ABSTRACT

A compound having an SSTR5 antagonist action and use of the compound as a medicament are provided. Specifically, a compound represented by the following formula:

wherein each symbol is as defined herein,
or a salt thereof, a medicament comprising the compound or a salt thereof, and use of the compound or a salt thereof as an agent the prophylaxis or treatment of diabetes mellitus are provided.

10 Claims, No Drawings

HETEROCYCLIC COMPOUND

The present application claims a priority right based on Japanese Patent Application No. 2013-224093 (filed Oct. 29, 2013), the content of which is incorporated herein by reference.

TECHNICAL FIELD

The present invention relates to a heterocyclic compound that has a somatostatin receptor subtype 5 (hereinafter sometimes to be abbreviated as "SSTR5") antagonist action and is useful in the treatment, improvement, or prophylaxis of diseases or states such as diabetes mellitus, insulin resistance, dyslipidemia, obesity, atherosclerosis, cardiovascular disease, metabolic syndrome, neurosis, and the like.

BACKGROUND OF THE INVENTION

Diabetes mellitus (DM) is a disease that causes a pathologic elevation in blood glucose level (glucose concentration in blood) due to impaired insulin secretion or insulin resistance and is known to serve as a risk factor for various serious complications. Diabetes mellitus is reportedly developed by the involvement of various environmental factors (a lack of exercise, overeating, and obesity, etc.) on the basis of genetic factors. The number of diabetes mellitus patients is expected to increase in the future with increases in obese population. Diabetes mellitus is classified into insulin-dependent diabetes mellitus (IDDM) (type 1 diabetes mellitus) and non-insulin-dependent diabetes mellitus (type 2 diabetes mellitus). The great part (about 90%) of diabetes mellitus patients is classified as type 2 diabetes mellitus patients.

Type 1 diabetes mellitus is a disease in which beta cells, which secrete insulin in the pancreatic islets of Langerhans, are killed due to various genetic factors and acquired factors. Type 2 diabetes mellitus is a disease that is caused by insufficient amounts of insulin secreted in response to glucose in beta cells and by reduction in insulin sensitivity in peripheral tissues (liver, muscle, and fat, etc.).

As for the treatment and prophylaxis of diabetes mellitus, diet therapy and exercise therapy as well as medication is practiced.

Examples of current typical medication include medication involving subcutaneously administering insulin, an insulin analog, or a GLP-1 (glucagon-like peptide-1) analog or the like, and medication using an orally administrable hypoglycemic drug. The orally administrable hypoglycemic drug includes sulfonylureas (SU drugs) such as glimepiride and the like; biguanides (BG drugs) such as metformin and the like; alpha-glucosidase inhibitors (alpha-GI drugs) such as voglibose, miglitol, and the like; thiazolidine derivatives (TZD drugs) such as pioglitazone and the like; DPP-IV (dipeptidyl peptidase-IV) inhibitors such as Sitagliptin, Alogliptin, and the like; etc.

Somatostatin is widely distributed in the central nervous system including the hypothalamus and the like, the pancreatic islets of Langerhans, and the intestinal mucosa, etc., and plays an important role in the control of gastrointestinal motility, digestive juice secretion, and glucose or lipid metabolism. Particularly, in living organisms, somatostatin is known to suppressively act on the production or secretion of various hormones, growth factors, and biologically active substances. The hormones on which somatostatin suppressively acts include growth hormone (GH), thyroid stimulating hormone (TSH), prolactin, insulin, glucagon, gastrin, secretin, peptide YY (PYY), gastric inhibitory polypeptide (GIP), GLP-1, GLP-2, cholecystokinin (CCK), vasoactive intestinal peptide (VIP), oxyntomodulin, and the like. In addition, somatostatin also acts as paracrine in the pancreatic islets of Langerhans or the mucosa of gastrointestinal tract where delta cells are in contact with alpha cells and beta cells. Somatostatin therefore has diverse biological functions in the endocrine system, the exocrine system, and the nervous system, etc.

Somatostatin receptor is a seven-transmembrane G protein-coupled receptor. Five subtypes have been found so far and respectively designated as SSTR1, SSTR2, SSTR3, SSTR4, and SSTR5 (Non Patent Literature 1). Among them, SSTR5 has been shown to participate in the regulation of insulin and incretin secretions (Non Patent Literature 2).

Meanwhile, Patent Literature 1 has reported that the following compound has an SSTR5 antagonist action:

[Formula 1]

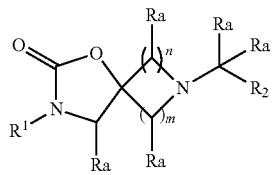

wherein each Ra is independently selected from the group consisting of a hydrogen atom, a halogen atom, a $C_{1-10}$ alkyl group, and a halogen atom-substituted $C_{1-10}$ alkyl group; $R^1$ is selected from the group consisting of a hydrogen atom, substituted phenyl, and a substituted heterocyclic ring; $R^2$ is selected from the group consisting of substituted aryl and a substituted heterocyclic ring; and n and m are each independently selected from the group consisting of 1, 2, and 3.

Patent Literatures 2 and 3 disclose that the following compound has an AMPA receptor inhibitory action and the like and may be used in the treatment of demyelinating disease or neurodegenerative disease:

[Formula 2]

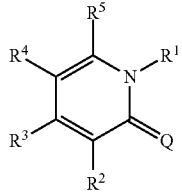

wherein Q represents NH, O, or S, $R^1$, $R^2$, $R^3$, $R^4$, and $R^5$ each represent a hydrogen atom, a halogen atom, a $C_{1-6}$ alkyl group, or a group represented by the formula —X-A (wherein X represents a single bond, substituted $C_{1-6}$ alkylene, —O—, —S—, or the like); and A represents a $C_{3-8}$ cycloalkyl group, a $C_{3-8}$ cycloalkenyl group, a 5- to 14-membered nonaromatic heterocyclic ring, a $C_{6-14}$ aromatic ring, or a 5- to 14-membered aromatic heterocyclic ring, provided that three of $R^1$ to $R^5$ are the same or different and each represent —X-A, and each of the remaining two is a hydrogen atom, a halogen atom, or a $C_{1-6}$ alkyl group.

Patent Literatures 2 and 3 also describe the following compound as one example of the above-mentioned compound in Example 379B:

[Formula 3]

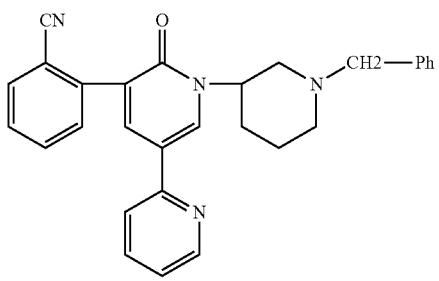

Li et al. discloses the following compound as to the oxidative conversion of isoxazolidine to isoxazoline (Non Patent Literature 3):

[Formula 4]

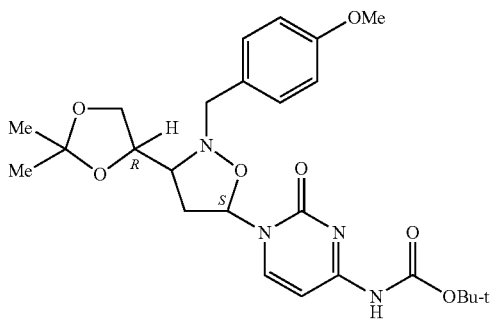

In addition to those mentioned above, the following compounds are known under CAS Registration Nos. 1381469-87-9, 1214501-97-9, and 1214473-59-2:

[Formula 5]

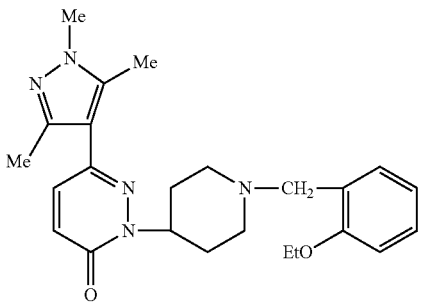

RN: 1381469-87-9

[Formula 6]

RN: 1214501-97-9

[Formula 7]

RN: 1214473-59-2

CITATION LIST

Patent Literature

[Patent Literature 1] International Publication No. WO 2012/024183

[Patent Literature 2] International Publication No. WO 2001/096308

[Patent Literature 3] International Publication No. WO 2003/047577

Non Patent Literature

[Non Patent Literature 1] Patel Y C: "Molecular pharmacology of somatostatin receptor subtypes." J Endocrinol Invest 20: 348-367, 1997

[Non Patent Literature 2] Chisholm C et al.: "Somatostatin-28 regulates GLP-1 secretion via somatostatin receptor subtype 5 in rat intestinal cultures." Am J Physiol Endocrinol Metab 283: E311-317, 2002

[Non Patent Literature 3] Pan Li et al.: "Oxidative Conversion of Isoxazolidines to Isoxazolines." J. Org. Chem. 63 (2): 366-369, 1998

SUMMARY OF INVENTION

Technical Problem

There has been a demand for the development of a compound that has an SSTR5 antagonist action and is useful in the treatment, improvement, or prophylaxis of diseases or states such as diabetes mellitus, insulin resistance, dyslipidemia, obesity, atherosclerosis, cardiovascular disease, metabolic syndrome, neurosis, and the like.

Solution to Problem

The present inventors have found for the first time a compound represented by the following formula:

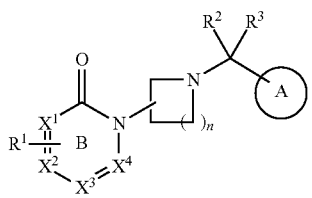
[Formula 8]

wherein ring A represents an optionally substituted benzene ring or an optionally substituted heterocyclic ring;
ring B represents a 6-membered nitrogen-containing heterocyclic ring optionally further substituted by 1 to 3 substituents selected from a halogen atom and a $C_{1-6}$ alkyl group;
$X^1$, $X^2$, $X^3$, and $X^4$ each independently represent a carbon atom or a nitrogen atom;
n represents an integer of 1 to 4;
$R^1$ represents $-L^1-L^2-COR^4$, an optionally substituted tetrazolyl group, or an optionally substituted dihydrooxadiazolyl group;
$L^1$ represents a bond, —O—, —S—, —SO—, —SO$_2$—, or —NR$^5$—;
$L^2$ represents a bond or an optionally substituted $C_{1-3}$ alkylene group;
$R^2$ and $R^3$ each independently represent a hydrogen atom or a $C_{1-6}$ alkyl group;
$R^4$ represents $NR^6R^7$ or $OR^8$; and
$R^5$, $R^6$, $R^7$, and $R^8$ each independently represent a hydrogen atom or an optionally substituted $C_{1-6}$ alkyl group,
or a salt thereof (hereinafter sometimes to be referred to as compound (I)) has a superior SSTR5 antagonist action, is useful in the treatment, improvement, or prophylaxis of diseases or states such as diabetes mellitus, insulin resistance, metabolic syndrome, dyslipidemia, obesity, atherosclerosis, cardiovascular disease, neurosis, and the like, and has superior efficacy. On the basis of this finding, the present inventors have conducted intensive studies, which resulted in the completion of the present invention.

Accordingly, the present invention relates to
[1] a compound represented by the following formula:

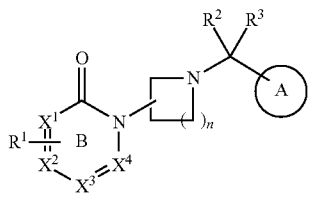
[Formula 9]

wherein ring A represents an optionally substituted benzene ring or an optionally substituted heterocyclic ring;
ring B represents a 6-membered nitrogen-containing heterocyclic ring optionally further substituted by 1 to 3 substituents selected from a halogen atom and a $C_{1-6}$ alkyl group;
$X^1$, $X^2$, $X^3$, and $X^4$ each independently represent a carbon atom or a nitrogen atom;
n represents an integer of 1 to 4;
$R^1$ represents $-L^1-L^2-COR^4$, an optionally substituted tetrazolyl group, or an optionally substituted dihydrooxadiazolyl group;
$L^1$ represents a bond, —O—, —S—, —SO—, —SO$_2$—, or —NR$^5$—;
$L^2$ represents a bond or an optionally substituted $C_{1-3}$ alkylene group;
$R^2$ and $R^3$ each independently represent a hydrogen atom or a $C_{1-6}$ alkyl group;
$R^4$ represents $NR^6R^7$ or $OR^8$; and
$R^5$, $R^6$, $R^7$, and $R^8$ each independently represent a hydrogen atom or an optionally substituted $C_{1-6}$ alkyl group,
or a salt thereof;
[2] the compound according to the above-mentioned [1] or a salt thereof, wherein ring A is
(1) a benzene ring optionally substituted by 1 to 4 substituents selected from:
a halogen atom; a $C_{3-10}$ cycloalkyl group; a $C_{1-6}$ alkoxy group; and a $C_{6-14}$ aryl group optionally substituted by 1 to 3 halogen atom(s), or
(2) pyridine optionally substituted by 1 to 3 substituents selected from:
a $C_{3-10}$ cycloalkyl group; a $C_{1-6}$ alkoxy group; and a $C_{6-14}$ aryl group optionally substituted by 1 to 3 halogen atom(s);
[3] the compound according to the above-mentioned [1] or [2] or a salt thereof, wherein ring B is pyridine or pyrimidine each optionally further substituted by 1 to 3 substituents selected from a halogen atom and a $C_{1-6}$ alkyl group;
[4] the compound according to any one of the above-mentioned [1] to [3] or a salt thereof, wherein n is 3;
[5] the compound according to any one of the above-mentioned [1] to [4] or a salt thereof, wherein $R^1$ is COOH, CONH$_2$, a tetrazolyl group, a dihydrooxadiazolyl group, or OCH$_2$COOH;
[6] the compound according to any one of the above-mentioned [1] to [5] or a salt thereof, wherein each of $R^2$ and $R^3$ is a hydrogen atom;
[7] the compound according to the above-mentioned [1] or a salt thereof, wherein ring A is
(1) a benzene ring optionally substituted by 1 to 4 substituents which are the same or different and selected from:
a halogen atom; a $C_{3-10}$ cycloalkyl group; a $C_{1-6}$ alkoxy group; and a $C_{6-14}$ aryl group optionally substituted by 1 to 3 halogen atom(s), or
(2) pyridine optionally substituted by 1 to 3 substituents which are the same or different and selected from:
a $C_{3-10}$ cycloalkyl group; a $C_{1-6}$ alkoxy group; and a $C_{6-14}$ aryl group optionally substituted by 1 to 3 halogen atom(s);
ring B is pyridine or pyrimidine each optionally further substituted by 1 to 3 substituents selected from a halogen atom and a $C_{1-6}$ alkyl group, wherein each of $X^1$, $X^2$, and $X^4$ is a carbon atom, and $X^3$ is a carbon atom or a nitrogen atom;
n is 3;
$R^1$ is COOH, CONH$_2$, a tetrazolyl group, or a dihydrooxadiazolyl group, or OCH$_2$COOH and is bonded to $X^2$ of ring B; and
each of $R^2$ and $R^3$ is a hydrogen atom;
[8] 1-(1-((2-cyclopropyl-4'-fluoro-5-isopropoxybiphenyl-4-yl)methyl)piperidin-4-yl)-2-oxo-1,2-dihydropyridin-4-carboxylic acid or a salt thereof;
[9] 1-(1-((6-cyclopropyl-2,4'-difluoro-3-isopropoxybiphenyl-4-yl)methyl)piperidin-4-yl)-3-ethyl-2-oxo-1,2-dihydropyridine-4-carboxylic acid or a salt thereof;
[10] 1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylic acid or a salt thereof;
[11] a medicament comprising the compound of the above-mentioned [1] or a salt thereof;
[12] the medicament of the above-mentioned [11], which is a somatostatin receptor 5 antagonist;
[13] the medicament of the above-mentioned [11], which is an agent for the prophylaxis or treatment of diabetes mellitus;

[14] a method for preventing or treating diabetes mellitus in a mammal, comprising administering to the mammal an effective amount of the compound according to the above-mentioned [1] or a salt thereof;

[15] a method for antagonizing somatostatin receptor subtype 5 in a mammal, comprising administering to the mammal an effective amount of the compound according to the above-mentioned [1] or a salt thereof;

[16] use of the compound according to the above-mentioned [1] or a salt thereof in the production of an agent for the prophylaxis or treatment of diabetes mellitus;

[17] the compound according to the above-mentioned [1] or a salt thereof for use in the prophylaxis or treatment of diabetes mellitus; etc.

Effects of Invention

Compound (I) has a superior SSTR5 antagonist action, is useful in the treatment, improvement, and prophylaxis of diseases or states such as diabetes mellitus, insulin resistance, metabolic syndrome, dyslipidemia, obesity, atherosclerosis, cardiovascular disease, neurosis, and the like, and has superior efficacy.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A. [substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,

(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_3$-10 cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2C(CH_3)_2$—, —$C(CH_3)_2$—$CH_2CH_2$—, —$CH_2$—$CH_2$—$CH_2$—$C(CH_3)_2$— and —$C(CH_3)_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —$C(CH_3)_2$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, triazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in compound (I) is described in detail in the following.

Ring A represents an optionally substituted benzene ring or an optionally substituted heterocyclic ring.

The "benzene ring" in the "optionally substituted benzene ring" represented by ring A may have 1 to 5, preferably 1 to 4, more preferably 3 or 4 substituents at substitutable positions. When the number of the substituents is two or more, the respective substituents may be the same or different.

Preferable examples of such substituents include a halogen atom (preferably fluorine, chlorine, bromine, iodine), a $C_{3-10}$ cycloalkyl group (preferably cyclopropyl, cyclobutyl), a $C_{1-6}$ alkoxy group (preferably methoxy, ethoxy, propoxy, isopropoxy), a $C_{3-10}$ cycloalkyloxy group (preferably cyclopentyloxy) and a $C_{6-14}$ aryl group (preferably phenyl) optionally substituted by 1 to 3 halogen atoms (preferably fluorine).

The "heterocyclic ring" in the "optionally substituted heterocyclic ring" represented by ring A is preferably a 5- to 14-membered heterocyclic ring, more preferably a 5- to 14-membered nitrogen-containing heterocyclic ring.

The "heterocyclic ring" in the "optionally substituted heterocyclic ring" represented by ring A is further preferably pyridine or indazole.

The "heterocyclic ring" in the "optionally substituted heterocyclic ring" represented by ring A is particularly preferably pyridine.

The "heterocyclic ring" may have 1 to 5, preferably 1 to 3, more preferably 3 substituents at substitutable positions. When the number of the substituents is two or more, the respective substituents may be the same or different.

Preferable examples of such substituents include a halogen atom (preferably fluorine, chlorine, bromine, iodine), a $C_{1-6}$ alkyl group (preferably methyl, ethyl, isopropyl, tert-butyl), a $C_{3-10}$ cycloalkyl group (preferably cyclopropyl), a $C_{1-6}$ alkoxy group (preferably methoxy, ethoxy, isopropoxy), and a $C_{6-14}$ aryl group (preferably phenyl) optionally substituted by 1 to 3 halogen atoms (preferably fluorine, chlorine).

Ring A is preferably an optionally substituted benzene ring, optionally substituted pyridine or optionally substituted indazole.

Ring A is more preferably an optionally substituted benzene ring or optionally substituted pyridine.

Preferable specific examples of ring A include (1) a benzene ring optionally substituted by 1 to 4 substituents selected from:

a halogen atom (preferably fluorine, chlorine); a $C_{3-10}$ cycloalkyl group (preferably cyclopropyl, cyclobutyl); a $C_{1-6}$ alkoxy group (preferably methoxy, ethoxy, isopropoxy); and a $C_{6-14}$ aryl group optionally substituted by 1 to 3 halogen atoms (preferably fluorine), or (2) pyridine optionally substituted by 1 to 3 substituents selected from:

a $C_{3-10}$ cycloalkyl group (preferably cyclopropyl); a $C_{1-6}$ alkoxy group (preferably ethoxy, isopropoxy); and a $C_{6-14}$ aryl group (preferably phenyl) optionally substituted by 1 to 3 halogen atoms (preferably fluorine, chlorine).

Particularly preferable specific examples of ring A include a benzene ring optionally substituted by 1 to 4 substituents selected from:

a halogen atom (preferably fluorine, chlorine); a $C_{3-10}$ cycloalkyl group (preferably cyclopropyl, cyclobutyl); a $C_{1-6}$ alkoxy group (preferably methoxy, ethoxy, isopropoxy); and a $C_{6-14}$ aryl group optionally substituted by 1 to 3 halogen atoms (preferably fluorine).

Ring B represents a 6-membered nitrogen-containing heterocyclic ring optionally further substituted by 1 to 3 substituents selected from a halogen atom and a $C_{1-6}$ alkyl group.

The "6-membered nitrogen-containing heterocyclic ring" represented by ring B is preferably a 6-membered nitrogen-containing aromatic heterocyclic ring. The 6-membered nitrogen-containing aromatic heterocyclic ring is particularly preferably pyridine or pyrimidine.

In the present specification, when ring B is pyridine or pyrimidine, the partial formula:

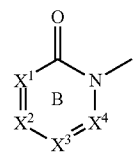

means respectively

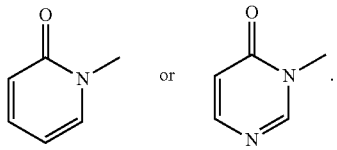

Accordingly, pyridine and pyrimidine as ring B include respectively dihydropyridine (preferably, 1,2-dihydropyridine) and dihydropyrimidine (preferably, 1,6-dihydropyrimidine).

Preferable examples of ring B include pyridine optionally further substituted by a $C_{1-6}$ alkyl group.

The "halogen atom" in the "6-membered nitrogen-containing heterocyclic ring optionally further substituted by 1 to 3 substituents selected from a halogen atom and a $C_{1-6}$ alkyl group" is preferably bromine.

The "$C_{1-6}$ alkyl group" in the "6-membered nitrogen-containing heterocyclic ring optionally further substituted by 1 to 3 substituents selected from a halogen atom and a $C_{1-6}$ alkyl group" is preferably methyl, ethyl, or propyl.

$X^1$, $X^2$, $X^3$, and $X^4$ each independently represent a carbon atom or a nitrogen atom.

Each of $X^1$, $X^2$, and $X^4$ is preferably a carbon atom.

$X^3$ is a carbon atom or a nitrogen atom and is preferably a carbon atom.

$R^1$ represents -$L^1$-$L^2$-$COR^4$, an optionally substituted tetrazolyl group, or an optionally substituted dihydrooxadiazolyl group, wherein $L^1$ represents a bond, —O—, —S—, —SO—, —$SO_2$—, or —$NR^5$—;

$L^2$ represents a bond or an optionally substituted $C_{1-3}$ alkylene group;

$R^4$ represents $NR^6R^7$ or $OR^8$; and $R^5$, $R^6$, $R^7$, and $R^8$ each independently represent a hydrogen atom or an optionally substituted $C_{1-6}$ alkyl group.

$L^1$ is preferably a bond.

$L^2$ is preferably a bond.

$R^4$ is preferably OH.

Each of $R^5$, $R^6$, $R^7$, and $R^8$ is preferably a hydrogen atom.

$R^1$ is preferably COOH, $CONH_2$, a tetrazolyl group, a dihydrooxadiazolyl group, or $OCH_2COOH$.

$R^1$ is more preferably COOH.

The binding position of $R^1$ on ring B is not particularly limited. Preferably, $R^1$ is bonded to $X^2$.

$R^2$ and $R^3$ each independently represent a hydrogen atom or a $C_{1-6}$ alkyl group. Each of $R^2$ and $R^3$ is preferably a hydrogen atom.

n represents an integer of 1 to 4. n is preferably 3.

When n is 3, piperidine is formed. In this case, preferably, the carbon atom at 4-position of this piperidine is bonded to the nitrogen atom of ring B as shown in [Formula 10] below.

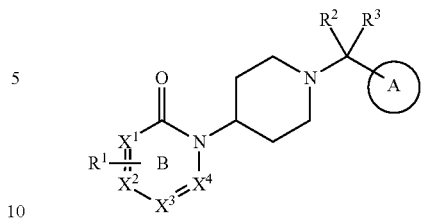

Preferable examples of compound (I) include the following compound:

[Compound A]

Compound (I) wherein ring A is (1) a benzene ring optionally substituted by 1 to 4 substituents which are the same or different and selected from a halogen atom (preferably fluorine, chlorine); a $C_{3-10}$ cycloalkyl group (preferably cyclopropyl, cyclobutyl); a $C_{1-6}$ alkoxy group (preferably methoxy, ethoxy, isopropoxy); and a $C_{6-14}$ aryl group optionally substituted by 1 to 3 halogen atoms (preferably fluorine); or (2) pyridine optionally substituted by 1 to 3 substituents which are the same or different and selected from a $C_{3-10}$ cycloalkyl group (preferably cyclopropyl); a $C_{1-6}$ alkoxy group (preferably ethoxy, isopropoxy); and an optionally substituted $C_{6-14}$ aryl group (preferably phenyl optionally substituted by 1 to 3 halogen atoms (preferably fluorine));

ring B is pyridine or pyrimidine (wherein each of $X^1$, $X^2$, and $X^4$ is a carbon atom, and $X^3$ is a carbon atom or a nitrogen atom);

n is 3;

$R^1$ is COOH, $CONH_2$, a tetrazolyl group, a dihydrooxadiazolyl group, or $OCH_2COOH$ and is bonded to $X^2$ of ring B; and each of $R^2$ and $R^3$ is a hydrogen atom.

[Compound A']

Compound (I) wherein ring A is (1) a benzene ring optionally substituted by 1 to 4 substituents which are the same or different and selected from a halogen atom (preferably fluorine, chlorine); a $C_{3-10}$ cycloalkyl group (preferably cyclopropyl, cyclobutyl); a $C_{1-6}$ alkoxy group (preferably methoxy, ethoxy, isopropoxy); and a $C_{6-14}$ aryl group optionally substituted by 1 to 3 halogen atoms (preferably fluorine); or (2) pyridine optionally substituted by 1 to 3 substituents which are the same or different and selected from a $C_{3-10}$ cycloalkyl group (preferably cyclopropyl); a $C_{1-6}$ alkoxy group (preferably ethoxy, isopropoxy); and a $C_{6-14}$ aryl group (preferably phenyl) optionally substituted by 1 to 3 halogen atoms (preferably fluorine);

ring B is pyridine or pyrimidine each optinaly further substituted by 1 to 3 substituents selected from a halogen atom and a $C_{1-6}$ alkyl group (wherein each of $X^1$, $X^2$, and $X^4$ is a carbon atom, and $X^3$ is a carbon atom or a nitrogen atom);

n is 3;

$R^1$ is COOH, $CONH_2$, a tetrazolyl group, a dihydrooxadiazolyl group, or $OCH_2COOH$ and is bonded to $X^2$ of ring B; and each of $R^2$ and $R^3$ is a hydrogen atom.

[Compound A'-1]
Compound A' wherein
ring A is a benzene ring optionally substituted by 1 to 4 substituents selected from
a halogen atom (preferably fluorine, chlorine); a $C_{3-10}$ cycloalkyl group (preferably cyclopropyl, cyclobutyl); a $C_{1-6}$ alkoxy group (preferably methoxy, ethoxy, isopropoxy); and a $C_{6-14}$ aryl group (preferably phenyl) optionally substituted by 1 to 3 halogen atoms (preferably fluorine).
[Compound A'-2]
Compound A'-1 wherein
ring B is pyridine optinaly further substituted by a $C_{1-6}$ alkyl group (preferably methyl or ethyl) (wherein each of $X^1$, $X^2$, $X^3$, and $X^4$ is a carbon atom.
[Compound A'-3]
Compound A'-1 or compound A'-2 wherein
$R^1$ is COOH and is bonded to $X^2$ of ring B.

The salt of compound (I) is preferably a pharmacologically acceptable salt. Examples of such salt include salts with inorganic bases, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (I) may be used as a prodrug.

A prodrug of compound (I) is a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

Examples of a prodrug of compound (I) include:
a compound wherein an amino group of compound (I) is acylated, alkylated or phosphorylated (e.g., compound wherein an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like);
a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated or dimethylaminomethylcarbonylated);
a compound wherein a carboxy group of compound (I) is esterified or amidated (e.g., a compound wherein a carboxy group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated); and the like. These compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, the prodrug may form a salt. Examples of such a salt include those exemplified as the above-mentioned salt of compound (I).

Alternatively, compound (I) may be labeled with an isotope (e.g., $^3H$, $^{13}C$, $^{14}C$, $^{18}F$, $^{35}S$, $^{125}I$) or the like.

Furthermore, compound (I) may be a hydrate, a non-hydrate, a non-solvate, or a solvate.

In addition, a deuterium conversion form wherein $^1H$ is converted to $^2H(D)$ is also included in compound (I).

Compound (I) labeled or substituted with an isotope can be used as, for example, a tracer (PET tracer) for use in Positron Emission Tomography (PET), and is useful in the fields of medical diagnosis and the like.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

Compound (I) or a prodrug thereof (hereinafter to be sometimes abbreviated simply as the compound of the present invention) shows low toxicity. Thus, the compound of the present invention can be prepared into a pharmaceutical composition alone or in admixture with a pharmacologically acceptable carrier or the like and thereby used as an agent for the prophylaxis or treatment of various diseases mentioned below in a mammal (e.g., human, mouse, rat, rabbit, dog, cat, bovine, horse, pig, monkey).

In this context, any of various organic or inorganic carrier materials that are conventionally used as preparation materials can be used as the pharmacologically acceptable carrier. These are formulated as an excipient, a lubricant, a binding agent, and a disintegrant for solid preparations or as a solvent, a solubilizing agent, a suspending agent, an isotonic agent, a buffering agent, a soothing agent, and the like for liquid preparations. Further, if necessary, formulation additives such as preservative, antioxidant, colorant, sweetening agent, and the like can also be used.

Preferable examples of the excipient include lactose, sucrose, D-mannitol, D-sorbitol, starch, pregelatinized starch, dextrin, crystalline cellulose, low-substituted hydroxypropylcellulose, carboxymethylcellulose sodium, gum arabic, pullulan, light anhydrous silicic acid, synthetic aluminum silicate, and magnesium alumino metasilicate.

Preferable examples of the lubricant include magnesium stearate, calcium stearate, talc, and colloidal silica.

Preferable examples of the binding agent include pregelatinized starch, sucrose, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, and polyvinylpyrrolidone.

Preferable examples of the disintegrant include lactose, sucrose, starch, carboxymethylcellulose, carboxymethylcellulose calcium, croscarmellose sodium, carboxymethyl starch sodium, light anhydrous silicic acid, and low-substituted hydroxypropylcellulose.

Preferable examples of the solvent include water for injection, physiological saline, Ringer's solution, alcohol, propylene glycol, polyethylene glycol, sesame oil, corn oil, olive oil, and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, and sodium acetate.

Preferable examples of the suspending agent include surfactants such as stearyl triethanolamine, sodium lauryl sulfate, laurylaminopropionic acid, lecithin, benzalkonium chloride, benzethonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, and polyoxyethylene hydrogenated castor oil.

Preferable examples of the isotonic agent include sodium chloride, glycerin, D-mannitol, D-sorbitol, and glucose.

Preferable examples of the buffering agent include buffer solutions such as phosphates, acetates, carbonates, citrates and the like.

Preferable examples of the soothing agent include benzyl alcohol.

Preferable examples of the preservative include parahydroxybenzoic acid esters, chlorobutanol, benzyl alcohol, phenethyl alcohol, dehydroacetic acid, and sorbic acid.

Preferable examples of the antioxidant include sulfites and ascorbates.

Preferable examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), and natural dyes (e.g., beta-carotene, chlorophyll, ferric oxide red).

Preferable examples of the sweetening agent include saccharin sodium, dipotassium glycyrrhizinate, aspartame, and stevia.

A medicament comprising the compound of the present invention can be obtained using the compound of the present invention alone or in admixture with a pharmacologically acceptable carrier, and safely administered orally or parenterally (e.g., administered intravenously, intramuscularly, subcutaneously, into an organ, into a nasal cavity, intracutaneously, through ocular instillation, intracerebrally, rectally, vaginally, intraperitoneally, to the inside of tumor, to the proximity of tumor, and the like, and administered directly to a lesion) to a mammal as a pharmaceutical composition, for example, tablets (inclusive of sugar-coated tablets, film-coated tablets, sublingual tablets, orally disintegrating tablets, buccal tablets, and the like), pills, powders, granules, capsules (inclusive of soft capsules, microcapsules), troches, syrups, liquids, emulsions, suspensions, aerosols, films, (e.g., orally disintegrating films, patch films for application to the oral mucosa), injections (e.g., subcutaneous injections, intravenous injections, intramuscular injections, intraperitoneal injections), transfusions, dermal preparations, ointments, lotions, patches, suppositories (e.g., rectal suppositories, vaginal suppositories), pellets, nasal preparations, pulmonary preparations (inhalants), eye drops, and the like.

The pharmaceutical composition may be a controlled release preparation such as a rapid release preparation, a sustained release preparation, and the like (e.g., a sustained release microcapsule).

The pharmaceutical composition can be produced by a method that is conventionally used in the field of formulation technology, for example, the method described in the Japanese Pharmacopoeia and the like.

The content of the compound of the present invention in the pharmaceutical composition differs depending on the dosage form, the dose of the compound of the present invention, etc. and is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention is low in its toxicity (e.g., acute toxicity, chronic toxicity, genetic toxicity, reproductive toxicity, pulmonary toxicity, carcinogenicity), shows a few side effects, and can be used for a mammal as an agent for the prophylaxis or treatment of various diseases or as a diagnostic drug for various diseases.

The compound of the present invention has a superior SSTR5 antagonist action.

The compound of the present invention can be used as an agent for the prophylaxis or treatment of, for example, diabetes mellitus (e.g., type 1 diabetes mellitus, type 2 diabetes mellitus, gestational diabetes mellitus, obese diabetes mellitus), obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like), hyperphagia, hyperlipidemia/dyslipidemia (e.g., hypertriglyceridemia, hypercholesterolemia, high LDL-cholesterolemia, low HDL-cholesterolemia, postprandial hyperlipemia), hypertension, cardiovascular disease, (e.g., cardiac failure, arrhythmia, ischemic heart disease, valvular heart disease, arteriosclerosis), diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (disease states having 3 or more selected from hypertriglycerid(TG)emia, low HDL cholesterol(HDL-C)emia, hypertension, abdominal obesity and impaired glucose tolerance), sarcopenia, affective disorder, sexual dysfunction, depression, anxiety, neurosis, arteriosclerosis, knee arthritis and the like.

"Report of the Committee on the classification and diagnostic criteria of diabetes mellitus" was reported by The Japan Diabetes Society in 2010 about the diagnostic criteria of diabetes mellitus.

According to this report, diabetes mellitus refers to a state that meets any of a fasting blood glucose level (glucose concentration in venous plasma) of 126 mg/dL or more, a 2-hr value (glucose concentration in venous plasma) of 200 mg/dL or more in the 75 g oral glucose tolerance test (75 g OGTT), a casual blood glucose level (glucose concentration in venous plasma) of 200 mg/dL or more, and HbA1c (international standard value) of 6.5% or more. However, HbA1c (international standard value) (%) is indicated as an internationally standardized value corresponding to NGSP (National Glycohemoglobin Standardization Program) by 0.4% plus the conventional JDS (Japan Diabetes Society) value of HbA1c (JDS value) (%). Also, a state that does not apply to the above-mentioned diabetes mellitus, and is not a state exhibiting "a fasting blood glucose level (glucose concentration in venous plasma) less than 110 mg/dL or a 2-hr value (glucose concentration in venous plasma) less than 140 mg/dL in the 75 g oral glucose tolerance test (75 g OGTT)" (normal type) is called "borderline type".

According to the report by World Health Organization (WHO) in 2006, diabetes mellitus refers to a state that meets a fasting blood glucose level (glucose concentration in venous plasma) of 126 mg/dL or more or a 2-hr value (glucose concentration in venous plasma) of 200 mg/dL or more in the 75 g oral glucose tolerance test.

According to the above-mentioned reports, impaired glucose tolerance (IGT) refers to a state that meets a fasting blood glucose level (glucose concentration in venous plasma) less than 126 mg/dL and a 2-hr value (glucose concentration in venous plasma) of 140 mg/dL or more and less than 200 mg/dL in the 75 g oral glucose tolerance test. According to the report of WHO, a state exhibiting a fasting blood glucose level (glucose concentration in venous plasma) of 110 mg/dL or more and less than 126 mg/dL and a 2-hr value (glucose concentration in venous plasma) less than 140 mg/dL in the 75 g oral glucose tolerance test, if it has been measured, is called IFG (Impaired Fasting Glucose).

The compound of the present invention is also used as an agent for the prophylaxis or treatment of diabetes mellitus, borderline type diabetes mellitus, impaired glucose tolerance or IFG (Impaired Fasting Glucose) determined according to the above-mentioned reports. Moreover, the compound of the present invention can prevent progress of borderline type, impaired glucose tolerance or IFG (Impaired Fasting Glucose) into diabetes mellitus.

The compound of the present invention is also useful as an agent for the prophylaxis or treatment of metabolic syndrome. The incidence of cardiovascular disease is significantly high in metabolic syndrome patients, compared with patients with a single lifestyle-related disease. Thus, the prophylaxis or treatment of metabolic syndrome is exceedingly important for preventing cardiovascular disease.

The diagnostic criteria of metabolic syndrome were announced by WHO in 1999 and by NCEP in 2001. According to the diagnostic criteria of WHO, an individual having hyperinsulinemia or abnormal glucose tolerance as a requirement and two or more of visceral obesity, dyslipidemia (high TG or low HDL) and hypertension is diagnosed as having metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the diagnostic criteria of the Adult Treatment Panel III of the National Cholesterol Education Program (guideline of ischemic heart disease) in USA, an individual having three or more of visceral obesity, hypertriglyceridemia, low HDL-cholesterolemia, hypertension and abnormal glucose tolerance is diagnosed as having metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used as an agent for the prophylaxis or treatment of, for example, osteoporosis, cachexia (e.g., cancerous cachexia, tuberculous cachexia, diabetic cachexia, cachexia associated with blood disease, cachexia associated with endocrine disease, cachexia associated with infectious disease or cachexia caused by acquired immunodeficiency syndrome), fatty liver, polycystic ovary syndrome, renal disease (e.g., diabetic nephropathy, glomerulonephritis, glomerulosclerosis, Nephrotic syndrome, hypertensive nephrosclerosis, end-stage renal disease), muscular dystrophy, myocardial infarction, angina pectoris, cerebrovascular disorder (e.g., cerebral infarction, stroke), Alzheimer's disease, Parkinson's disease, dementia, insulin resistant syndrome, syndrome X, hyperinsulinemia, paresthesia caused by hyperinsulinemia, acute or chronic diarrhea, inflammatory disease (e.g., chronic rheumatoid arthritis, spondylitis deformans, arthritis deformans, lumbago, gout, post-operational or post-traumatic inflammation, bloating, neuralgia, laryngopharyngitis, cystitis, hepatitis (including non-alcoholic steatohepatitis), pneumonia, pancreatitis, ulcers, gastritis, digestion disorders, gastric mucosal injury (including gastric mucosal injury caused by aspirin)), cul-de-sac syndrome, inflammatory bowel disease (including inflammatory large bowel disease), celiac sprue (for example arising from gluten induced enteropathy or celiac disease), tropical sprue, hypogammaglobulinemic sprue, enteritis, regional enteritis (Crohn's disease), irritable bowel syndrome associated with diarrhea, small intestine damage (including small intestinal mucosal injury) and short bowel syndrome, reflux esophagitis, ulcerous colitis, malabsorption, testicular dysfunction, visceral obesity syndrome and sarcopenia.

Moreover, the compound of the present invention can also be used as an agent for the prophylaxis or treatment of various cancers (particularly, breast cancer (e.g., invasive ductal breast cancer, noninvasive ductal breast cancer, inflammatory breast cancer, etc.), prostate cancer (e.g., hormone-dependent prostate cancer, hormone-independent prostate cancer, etc.), pancreatic cancer (e.g., ductal pancreatic cancer, etc.), gastric cancer (e.g., papillary adenocarcinoma, mucous adenocarcinoma, adenosquamous carcinoma, etc.), lung cancer (e.g., non-small cell lung cancer, small-cell lung cancer, malignant mesothelioma, etc.), colon cancer (e.g., gastrointestinal stromal tumor, etc.), rectal cancer (e.g., gastrointestinal stromal tumor, etc.), colorectal cancer (e.g., familial colorectal cancer, hereditary non-polyposis colorectal cancer, gastrointestinal stromal tumor, etc.), small intestinal cancer (e.g., non-Hodgkin's lymphoma, gastrointestinal stromal tumor, etc.), esophageal cancer, duodenal cancer, tongue cancer, pharyngeal cancer (e.g., nasopharyngeal cancer, oropharynx cancer, hypopharyngeal cancer, etc.), salivary gland cancer, brain tumor (e.g., pineal astrocytoma, pilocytic astrocytoma, diffuse astrocytoma, anaplastic astrocytoma, etc.), neurilemmoma, liver cancer (e.g., primary liver cancer, extrahepatic bile duct cancer, etc.), renal cancer (e.g., renal cell cancer, transitional cell cancer of the renal pelvis and ureter, etc.), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential, etc.), bladder cancer, urethral cancer, skin cancer (e.g., intraocular (ocular) melanoma, Merkel cell carcinoma, etc.), hemangioma, malignant lymphoma, malignant melanoma, thyroid cancer (e.g., medullary thyroid cancer, etc.), parathyroid cancer, nasal cavity cancer, sinus cancer, bone tumor (e.g., osteosarcoma, Ewing tumor, uterine sarcoma, soft tissue sarcoma, etc.), angiofibroma, sarcoma of the retina, penis cancer, testicular tumor, pediatric solid tumor (e.g., Wilms' tumor, childhood kidney tumor, etc.), Kaposi's sarcoma, Kaposi's sarcoma caused by AIDS, tumor of maxillary sinus, fibrous histiocytoma, leiomyosarcoma, rhabdomyosarcoma, leukemia (e.g., acute myeloid leukemia, acute lymphoblastic leukemia, etc.), etc.).

The compound of the present invention can also be used for secondary prevention or suppression of progression of the above-mentioned various diseases (e.g., cardiovascular events such as myocardial infarction and the like).

The dosage of the compound of the present invention is appropriately determined according to the subject of administration, administration route, target disease, symptom and the like. For example, when the compound of the present invention is administered orally to an adult obesity patient, a single dose is typically about 0.01 to 100 mg/kg body weight, preferably about 0.05 to 30 mg/kg body weight, more preferably about 0.5 to 10 mg/kg body weight. The single dose of the compound is preferably administered once to three times a day.

The compound of the present invention can be used in combination with a drug (hereinafter abbreviated as a concomitant drugs) such as therapeutic agents for diabetes mellitus, therapeutic agents for diabetic complications, therapeutic agents for hyperlipidemia, antihypertensive agents, antiobesity agents, diuretics, antithrombotic agents and the like for the purpose of promoting the action of the compound, reducing the dose of the compound, or the like. In this respect, the time of administration of the compound of the present invention and that of the concomitant drug are not limited. These concomitant drugs may be low-molecular-weight compounds or may be macromolecules such as proteins, polypeptides, antibodies, vaccines, and the like. The compound of the present invention and the concomitant drug may be administered simultaneously or in a staggered manner to the administration subject. Furthermore, the compound of the present invention and the concomitant drug may be administered as two types of preparations respectively comprising the active ingredients or as a single preparation comprising both of the active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01 to 100 parts by weight relative to 1 part by weight of the compound of the present invention.

Here, as the therapeutic agent for diabetes mellitus, for example, insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), a-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors (e.g., Alogliptin or a salt thereof (preferably, benzoate), Vildagliptin, Sitagliptin, Saxagliptin, Tenegliptin, Linagliptin, Anagliptin, Melogliptin, Dutogliptin, PF-00734200, ALS2-0426, TA-6666, TS-021, KRP-104, Trelagliptin or a salt thereof (preferably, succinate)), beta-3 agonists (e.g., N-5984), GPR40 agonists (e.g., fasiglifam, compound described in WO2004/041266, WO2004/106276, WO2005/063729, WO2005/063725, WO2005/087710, WO2005/095338, WO2007/013689 or WO2008/001931), GLP-1 receptor agonists [e.g., GLP-1, GLP-1 MR preparations, liraglutide, exenatide, AVE-0010, BIM-51077, Aib(8, 35)hGLP-1(7,37)NH$_2$, CJC-1131, albiglutide], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., dapagliflozin, AVE2268, TS-033, YM543, TA-7284, Remogliflozin, ASP1941), SGLT1 inhibitors, 11-beta-hydroxysteroid dehydrogenase inhibitors (e.g., BVT-3498), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO006/112549, WO007/028135, WO008/047821, WO008/050821, WO008/136428 or WO008/156757), GIP (Glucose-dependent insulinotropic peptide) and the like can be mentioned.

As the therapeutic agent for diabetic complications, for example, aldose reductase inhibitors (e.g., tolrestat, epalrestat, zopolrestat, fidarestat, CT-112, ranirestat (AS-3201), lidorestat), neurotrophic factor and increasing agents thereof (e.g., NGF, NT-3, BDNF, neurotrophic production/secretion promoting agent described in WO01/14372 (e.g., 4-(4-chlorophenyl)-2-(2-methyl-1-imidazolyl)-5-[3-(2-methylphenoxyl)propyl]oxazole), compound described in WO2004/039365), nerve regeneration-promoting drugs (e.g., Y-128), PKC inhibitors (e.g., ruboxistaurin mesylate), AGE inhibitors (e.g., ALT946, N-phenacylthiazolium bromide (ALT766), ALT-711, EXO-226, Pyridorin, pyridoxamine), GABA receptor agonists (e.g., gabapentin, pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like can be mentioned.

As the therapeutic agent for hyperlipidemia, for example, statin compounds (e.g., pravastatin, simvastatin, lovastatin, atorvastatin, fluvastatin, rosuvastatin, pitavastatin, cerivastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), probucol, nicotinic acid drugs (e.g., nicomol, niceritrol, niaspan), ethyl icosapentate, phytosterol (e.g., soysterol, gamma oryzanol, cholesterol absorption inhibitors (e.g., zechia), CETP inhibitors (e.g., dalcetrapib, anacetrapib), omega-3 fatty acid preparations (e.g., omega-3-fatty acid ethyl esters 90) and the like can be mentioned.

Examples of the antihypertensive agent include angiotensin converting enzyme inhibitors (e.g., captopril, enalapril, delapril, etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, amlodipine, cilnidipine, etc.), beta blockers (e.g., metoprolol, atenolol, propranolol, carvedilol, pindolol), renin inhibitors (e.g., aliskiren), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor, GABA modulator (e.g., topiramate), MCH receptor antagonists (e.g., SB-568849; SNAP-7941; the compounds described in WO01/82925 or WO01/87834), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists (e.g., almorexant), melanocortin 4 receptor agonists, 11-beta-hydroxysteroid dehydrogenase inhibitors (e.g., AZD-4017), pancreatic lipase inhibitors (e.g., orlistat, cetilistat), beta-3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, dapagliflozin, canagliflozin, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., meterleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized by using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), combination of a sustained release preparation of naltrexone hydrochloride and a sustained release preparation of bupropion hydrochloride, anorexigenic agents (e.g., P-57) and the like.

As the diuretic, for example, xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene, potassium canrenoate), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like can be mentioned.

As the antithrombotic agent, for example, heparin (e.g., heparin sodium, heparin calcium, enoxaparin sodium, dalteparin sodium), warfarin (e.g., warfarin potassium), antithrombin drugs (e.g., aragatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride, prasugrel, ticagrelor), Fxa inhibitors (e.g., rivaroxaban, apixaban, edoxaban, YM150, compound described in WO02/06234, WO2004/048363, WO2005/030740, WO2005/058823 or WO2005/113504) and the like can be mentioned.

The time of administration of the above-mentioned concomitant drug is not limited, and the compound of the present invention and the concomitant drug may be administered simultaneously or in a staggered manner to the administration subject. The dose of the concomitant drug can conform to the dose employed in clinical situations and can be appropriately determined depending on the administration subject, administration route, disease, combination and the like.

The administration mode of the concomitant drug is not particularly limited, and it is only required that the compound of the present invention and the concomitant drug should be combined at the time of administration. Examples of such administration mode include the following:
1) administration of a single preparation obtained by simultaneously processing the compound of the present invention and the concomitant drug,
2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes, 5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug can be appropriately determined depending on the administration subject, administration route, disease and the like.

Methods for producing the compound of the present invention are described in the following.

In production methods given below, starting materials or reagents used in each step and obtained compounds may each form a salt. Examples of such salt include the same as the above-mentioned salt of the compound of the present invention and the like.

When the compound obtained in each step is a free compound, it can be converted to a salt of interest by a method known per se. On the contrary, when the compound obtained in each step is a salt, it can be converted to a free form or a different type of salt of interest by a method known per se.

The compound obtained in each step may be used in subsequent reaction directly in the form of a reaction solution thereof or after being obtained as a crude product. Alternatively, the compound obtained in each step can be isolated and/or purified from the reaction mixture by separation means such as concentration, crystallization, recrystallization, distillation, solvent extraction, fractionation, chromatography, and the like according to a conventional method.

When compounds of starting materials or reagents for each step are commercially available, these commercially available products can be used directly.

For reaction in each step, the reaction time may differ depending on the reagent or solvent used and is usually 1 minute to 48 hours, preferably 10 minutes to 8 hours, unless otherwise specified.

For reaction in each step, the reaction temperature may differ depending on the reagent or solvent used and is usually −78 C ("C" represents "degrees Celsius") to 300 C, preferably −78 C to 150 C, unless otherwise specified.

For reaction in each step, the pressure may differ depending on the reagent or solvent used and is usually 1 atm to 20 atm, preferably 1 atm to 3 atm, unless otherwise specified.

For reaction in each step, for example, a microwave synthesis apparatus such as Initiator manufactured by Biotage Japan Ltd. and the like may be used. The reaction temperature may differ depending on the reagent or solvent used and is usually room temperature to 300 C, preferably 50 C to 250 C, unless otherwise specified. The reaction time may differ depending on the reagent or solvent used and is usually 1 minute to 48 hours, preferably 1 minute to 8 hours, unless otherwise specified.

For reaction in each step, a reagent is used at 0.5 equivalents to 20 equivalents, preferably 0.8 equivalents to 5 equivalents, relative to a substrate, unless otherwise specified. When a reagent is used as a catalyst, the reagent is used at 0.001 equivalents to 1 equivalent, preferably 0.01 equivalents to 0.2 equivalents, relative to a substrate. When a reagent also serves as a reaction solvent, the reagent is used in the amount of the solvent.

For reaction in each step, the reaction is performed without a solvent or after dissolution or suspension in an appropriate solvent, unless otherwise specified. Specific examples of the solvent include the solvents described in Examples and the following:

Alcohols: methanol, ethanol, tert-butyl alcohol, 2-methoxyethanol, etc.;
Ethers: diethyl ether, diphenyl ether, tetrahydrofuran, 1,2-dimethoxyethane, etc.;
Aromatic hydrocarbons: chlorobenzene, toluene, xylene, etc.;
Saturated hydrocarbons: cyclohexane, hexane, etc.;
Amides: N,N-dimethylformamide, N-methylpyrrolidone, etc.;
Halogenated hydrocarbons: dichloromethane, carbon tetrachloride, etc.;
Nitriles: acetonitrile, etc.; Sulfoxides: dimethyl sulfoxide, etc.;
Aromatic organic bases: pyridine, etc.;
Acid anhydrides: acetic anhydride, etc.;
Organic acids: formic acid, acetic acid, trifluoroacetic acid, etc.;
Inorganic acids: hydrochloric acid, sulfuric acid, etc.;
Esters: ethyl acetate, etc.;
Ketones: acetone, methyl ethyl ketone, etc.; and
Water.

These solvents may be used as a mixture of two or more thereof at an appropriate ratio.

When a base is used for reaction in each step, any of the following bases or the bases described in Examples, for example, is used.
Inorganic bases: sodium hydroxide, magnesium hydroxide, etc.;
Basic salts: sodium carbonate, calcium carbonate, sodium bicarbonate, etc.;
Organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, etc.;
Metal alkoxides: sodium ethoxide, potassium tert-butoxide, etc.;
Alkali metal hydrides: sodium hydride, etc.;
Metal amides: sodium amide, lithium diisopropylamide, lithium hexamethyldisilazide, etc.; and
Organic lithiums: n-butyllithium, etc.

When an acid or acidic catalyst is used for reaction in each step, any of the following acids or acidic catalysts or the acids or acidic catalysts described in Examples, for example, is used.
Inorganic acids: hydrochloric acid, sulfuric acid, nitric acid, hydrobromic acid, phosphoric acid, etc.;
Organic acids: acetic acid, trifluoroacetic acid, citric acid, p-toluenesulfonic acid, 10-camphorsulfonic acid, etc.; and
Lewis acids: boron trifluoride-diethyl ether complex, zinc iodide, anhydrous aluminum chloride, anhydrous zinc chloride, anhydrous iron chloride, etc.

Reaction in each step is performed in accordance with a method known per se, for example, the method described in Jikken Kagaku Koza (Encyclopedia of Experimental Chemistry in English), 5th Ed., Vol. 13-19 (edited by The Chemical Society of Japan); Shin Jikken Kagaku Koza (New Encyclopedia of Experimental Chemistry in English), Vol. 14-15 (edited by The Chemical Society of Japan); Reactions and Syntheses in the Organic Chemistry Laboratory, Revised, 2nd Ed. (L. F. Tietze, Th. Eicher, Nankodo Co., Ltd.); Revised Organic Name Reactions; The Reaction Mechanism and Essence (Hideo Togo, Kodansha Ltd.); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY Press); Comprehensive Heterocyclic Chemistry III, Vol. 1-14 (Elsevier B.V.); Strategic Applications of Named Reactions in Organic Synthesis (translated by Kiyoshi Tomioka, published by Kagaku-Dojin Publishing Company, INC); Comprehensive Organic Transformations (VCH Publishers Inc.) (1989), etc., or the method described in Examples, unless otherwise specified.

The protection or deprotection reaction of a functional group in each step is performed in accordance with a method known per se, for example, the method described in "Protective Groups in Organic Synthesis, 4th Ed." (Theodora W. Greene, Peter G. M. Wuts), Wiley-Interscience (2007); "Protecting Groups 3rd Ed." (P. J. Kocienski), Thieme Medical Publishers (2004), etc., or the method described in Examples.

Examples of protecting groups for the hydroxyl group or phenolic hydroxyl group of an alcohol or the like include ether type protecting groups such as methoxymethyl ether, benzyl ether, t-butyldimethylsilyl ether, tetrahydropyranyl ether, and the like; carboxylic acid ester type protecting groups such as acetic acid ester and the like; sulfonic acid ester type protecting groups such as methanesulfonic acid ester and the like; carbonic acid ester type protecting groups such as t-butyl carbonate and the like; etc.

Examples of protecting groups for the carbonyl group of an aldehyde include acetal type protecting groups such as dimethyl acetal and the like; cyclic acetal type protecting groups such as cyclic 1,3-dioxane and the like; etc.

Examples of protecting groups for the carbonyl group of a ketone include ketal type protecting groups such as dimethyl ketal and the like; cyclic ketal type protecting groups such as cyclic 1,3-dioxane and the like; oxime type protecting groups such as O-methyloxime and the like; hydrazone type protecting groups such as N,N-dimethylhydrazone and the like; etc.

Examples of protecting groups for the carboxyl group include ester type protecting groups such as methyl ester and the like; amide type protecting groups such as N,N-dimethylamide and the like; etc.

Examples of protecting groups for thiol include ether type protecting groups such as benzylthio ether and the like; ester type protecting groups such as thioacetic acid ester, thiocarbonate, thiocarbamate, and the like; etc.

Examples of protecting groups for the amino group or an aromatic heterocyclic ring such as imidazole, pyrrole, indole, or the like include carbamate type protecting groups such as benzyl carbamate and the like; amide type protecting groups such as acetamide and the like; alkylamine type protecting groups such as N-triphenylmethylamine and the like; sulfonamide type protecting groups such as methanesulfonamide and the like; etc.

A protecting group can be removed by a method known per se, for example, a method using acid, base, ultraviolet light, hydrazine, phenylhydrazine, sodium N-methyldithiocarbamate, tetrabutylammonium fluoride, palladium acetate, or trialkylsilyl halide (e.g., trimethylsilyl iodide, trimethylsilyl bromide), a reduction method, or the like.

In the case of performing reduction reaction in each step, examples of the reducing agent used include metal hydrides such as lithium aluminum hydride, sodium triacetoxy borohydride, sodium cyanoborohydride, diisobutyl aluminum hydride (DIBAL-H), sodium borohydride, tetramethylammonium triacetoxy borohydride, and the like; boranes such as borane-tetrahydrofuran complex and the like; Raney nickel; Raney cobalt; hydrogen; formic acid; etc. A catalyst such as palladium-carbon, a Lindlar's catalyst, or the like may be used in a method for reducing a carbon-carbon double bond or triple bond.

In the case of performing oxidation reaction in each step, examples of the oxidizing agent used include peracids such as m-chloroperbenzoic acid (MCPBA), hydrogen peroxide, t-butyl hydroperoxide, and the like; perchlorates such as tetrabutylammonium perchlorate and the like; chlorates such as sodium chlorate and the like; chlorites such as sodium chlorite and the like; periodates such as sodium periodate and the like; high-valent iodine reagents such as iodosylbenzene and the like; manganese-containing reagents such as manganese dioxide, potassium permanganate, and the like; leads such as lead tetraacetate and the like; chromium-containing reagents such as pyridinium chlorochromate (PCC), pyridinium dichromate (PDC), Jones reagents, and the like; halogen compounds such as N-bromosuccinimide (NBS) and the like; oxygen; ozone; sulfur trioxide-pyridine complex; osmium tetraoxide; selenium dioxide; 2,3-dichloro-5,6-dicyano-1,4-benzoquinone (DDQ); etc.

In the case of performing radical cyclization reaction in each step, examples of the radical initiator used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide; etc. Examples of the radical reagent used include tributylstannane, tristrimethylsilylsilane, 1,1,2,2-tetraphenyldisilane, diphenylsilane, samarium iodide, and the like.

In the case of performing Wittig reaction in each step, examples of the Wittig reagent used include alkylidene phosphoranes. The alkylidene phosphoranes can be prepared by a method known per se, for example, the reaction of a phosphonium salt with a strong base.

In the case of performing Horner-Emmons reaction in each step, examples of the reagent used include phosphonoacetic acid esters such as methyl dimethylphosphonoacetate, ethyl diethylphosphonoacetate, and the like; and bases such as alkali metal hydrides, organic lithiums, and the like.

In the case of performing Friedel-Crafts reaction in each step, examples of the reagent used include a Lewis acid and an acid chloride or an alkylating agent (e.g., alkyl halides, alcohols, olefins, etc.). Alternatively, an organic or inorganic acid may be used instead of the Lewis acid, and an acid anhydride such as acetic anhydride or the like may be used instead of the acid chloride.

In the case of aromatic nucleophilic substitution reaction in each step, a nucleophile (e.g., amines, imidazole, etc.) and a base (e.g., basic salts, organic bases, etc.) are used as reagents.

In the case of performing carbanion-mediated nucleophilic addition reaction, carbanion-mediated nucleophilic 1,4-addition reaction (Michael addition reaction), or carbanion-mediated nucleophilic substitution reaction in each step, examples of the base used for generating a carbanion include organic lithiums, metal alkoxides, inorganic bases, organic bases, and the like.

In the case of performing Grignard reaction in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, the reaction of alkyl halide or aryl halide with metal magnesium in the presence of ether or tetrahydrofuran as a solvent.

In the case of performing Knoevenagel condensation reaction in each step, an active methylene compound flanked by two electron withdrawing groups (e.g., malonic acid, diethyl malonate, malononitrile, etc.) and a base (e.g., organic bases, metal alkoxides, inorganic bases) are used as reagents.

In the case of performing Vilsmeier-Haack reaction in each step, phosphoryl chloride and an amide derivative (e.g., N,N-dimethylformamide, etc.) are used as reagents.

In the case of performing the azidation reaction of alcohols, alkyl halides, or sulfonic acid esters in each step, examples of the azidation agent used include diphenylphosphorylazide (DPPA), trimethylsilyl azide, sodium azide, and the like. For the azidation of alcohols, for example, a method using diphenylphosphorylazide and 1,8-diazabicyclo[5,4,0]undec-7-ene (DBU), a method using trimethylsilyl azide and a Lewis acid, or the like is used.

In the case of performing reductive amination reaction in each step, examples of the reducing agent used include sodium triacetoxy borohydride, sodium cyanoborohydride, hydrogen, formic acid, and the like. When a substrate is an amine compound, examples of the carbonyl compound used include paraformaldehyde as well as aldehydes such as acetaldehyde and the like and ketones such as cyclohexanone and the like. When a substrate is a carbonyl compound, examples of the amines used include primary amines such as ammonia, methylamine, and the like; secondary amines such as dimethylamine and the like; etc.

In the case of performing Mitsunobu reaction in each step, azodicarboxylic acid esters (e.g., diethyl azodicarboxylate (DEAD), diisopropyl azodicarboxylate (DIAD), etc.) and triphenylphosphine are used as reagents.

In the case of performing esterification reaction, amidation reaction, or urea formation reaction in each step, examples of the reagent used include acyl halides such as acid chloride, acid bromide, and the like; acid anhydrides, active esters, and activated carboxylic acids such as sulfuric acid ester and the like. Examples of the activator for carboxylic acids include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonic acid ester condensing agents such as 1,1-carbonyldiimidazole (CDI) and the like; diphenylphosphorylazide (DPPA); benzotriazol-1-yloxy-trisdimethylamino phosphonium salt (BOP reagent); 2-chloro-1-methyl-pyridinium iodide (Mukaiyama reagent); thionyl chloride; lower alkyl halo-formates such as ethyl chloroformate and the like; O-(7-azabenzotriazol-1-yl)-N,N,N',N'-tetramethyluronium hexafluorophosphate (HATU); sulfuric acid; combinations thereof; etc. In the case of using a carbodiimide condensing agent, an additive such as 1-hydroxybenzotriazole (HOBt), N-hydroxysuccinimide (HOSu), dimethylaminopyridine (DMAP), or the like may be further added to the reaction.

In the case of performing coupling reaction in each step, examples of the metal catalyst used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, and the like; platinum compounds; etc. A base may be further added to the reaction. Examples of such a base include inorganic bases, basic salts, and the like.

In the case of performing thiocarbonylation reaction in each step, typically, diphosphorus pentasulfide is used as a thiocarbonylation agent. In addition to diphosphorus pentasulfide, a reagent having a 1,3,2,4-dithiadiphosphetane-2,4-disulfide structure, such as 2,4-bis(4-methoxyphenyl-1,3,2,4-dithiadiphosphetane-2,4-disulfide (Lawesson's reagent) or the like may be used.

In the case of performing Wohl-Ziegler reaction in each step, examples of the halogenating agent used include N-iodosuccinimide, N-bromosuccinimide (NBS), N-chlorosuccinimide (NCS), bromine, sulfuryl chloride, and the like. Heat, light, or a radical initiator such as benzoyl peroxide, azobisisobutyronitrile, or the like can be added to the reaction to thereby accelerate the reaction.

In the case of performing the halogenation reaction of a hydroxy group in each step, examples of the halogenating agent used include a hydrohalic acid and an acid halide of an inorganic acid, specifically, hydrochloric acid, thionyl chloride, phosphorus oxychloride, or the like for chlorination, and 48% hydrobromic acid or the like for bromination. Also, a method for obtaining an alkyl halide from an alcohol by the action of triphenylphosphine and carbon tetrachloride or carbon tetrabromide, etc. may be used. Alternatively, a method for synthesizing an alkyl halide through two reaction steps involving the conversion of an alcohol to sulfonic acid ester and subsequent reaction with lithium bromide, lithium chloride, or sodium iodide, may be used.

In the case of performing Arbuzov reaction in each step, examples of the reagent used include alkyl halides such as ethyl bromoacetate and the like; and phosphites such as triethylphosphite, tri(isopropyl)phosphite, and the like.

In the case of performing sulfone esterification reaction in each step, examples of the sulfonating agent used include methanesulfonyl chloride, p-toluenesulfonyl chloride, methanesulfonic anhydride, p-toluenesulfonic anhydride, and the like.

In the case of performing hydrolysis reaction in each step, an acid or a base is used as a reagent. For the acid hydrolysis reaction of t-butyl ester, formic acid, triethylsilane, or the like may be added in order to reductively trap t-butyl cation by-products.

In the case of performing dehydration reaction in each step, examples of the dehydrating agent used include sulfuric acid, diphosphorus pentaoxide, phosphorus oxychloride, N,N'-dicyclohexylcarbodiimide, alumina, polyphosphoric acid, and the like.

Compound (1) can be produced by a method mentioned below from compound (2).

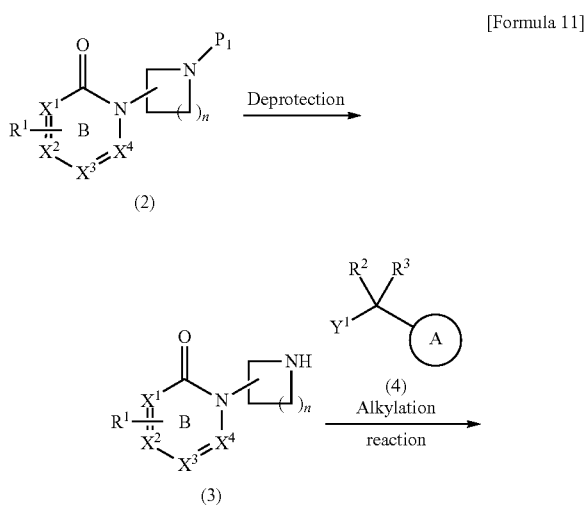

-continued

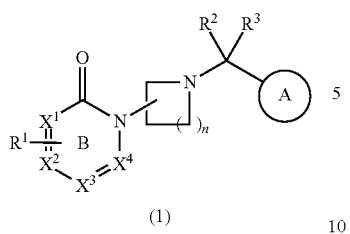

(1)

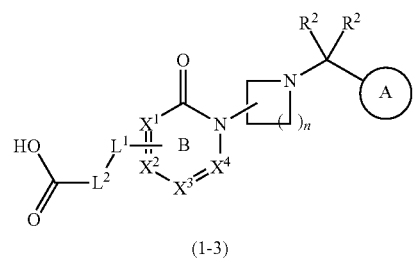

(1-3)

wherein $P^1$ represents a protecting group for the amino group; and $Y^1$ represents a sulfonate group or a halogen atom.

Compound (1) can be produced by alkylation reaction using compound (3), compound (4) and a base. Examples of the base include potassium carbonate, sodium carbonate, and the like. Compound (4) can be produced by a method known per se.

Of compounds (1), compound (1-1) can be produced by a method mentioned below from compound (3).

Of compounds (2), compound (2-1) can be produced by a method mentioned below from compound (6) and compound (7).

[Formula 12]

[Formula 14]

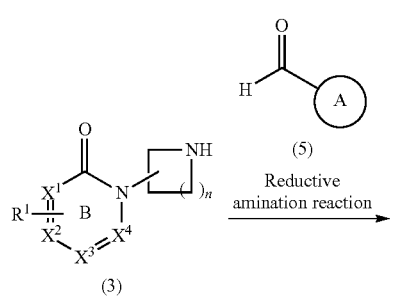

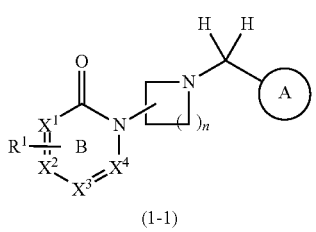

(1-1)

Compounds (5) can be produced by a method known per se.

Of compounds (1), compound (1-3) can be produced by a method mentioned below from compound (1-2).

Compound (2-1) can be produced by alkylation reaction using compound (6), compound (7), and a base. Examples of the base include potassium carbonate, sodium carbonate, potassium tert-butoxide, and the like. Compound (6) and compound (7) can be produced by a method known per se.

Of compounds (2), compound (2-2) can be produced by a method mentioned below from compound (8) and compound (7).

[Formula 13]

[Formula 15]

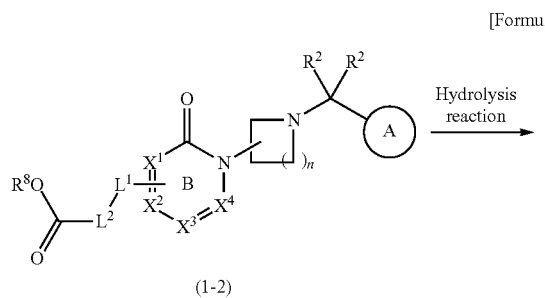

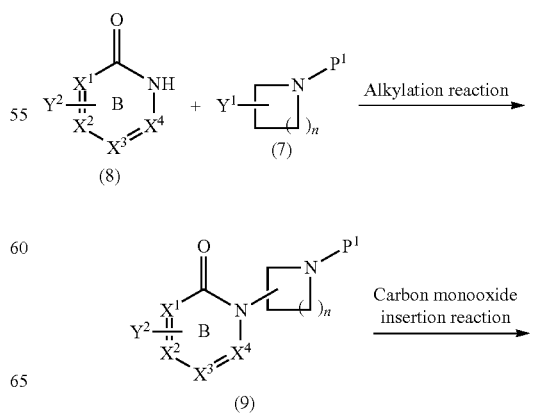

-continued

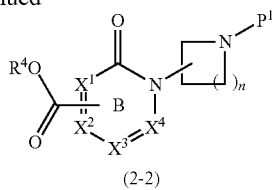

(2-2)

wherein $Y^2$ represents a sulfonate group, a halogen atom and a protected hydroxyl group. Compound (8) can be produced by a method known per se.

Compound (9) can be produced by alkylation reaction using compound (8), compound (7), and a base. Examples of the base include potassium carbonate, sodium carbonate, potassium tert-butoxide, and the like.

Compound (2-2) can be produced by carbon monooxide insertion reaction using compound (9), carbon monooxide, a base, and a palladium catalyst. Examples of the palladium catalyst include palladium acetate, a dichloromethane adduct of [1,1'-bis(diphenylphosphino)ferrocene]dichloropalladium (II), tris(dibenzylideneacetone)dipalladium, and the like. Examples of the base include triethylamine and the like.

Of compounds (2), compound (2-3) can be produced by a method mentioned below from compound (10) and compound (11).

[Formula 16]

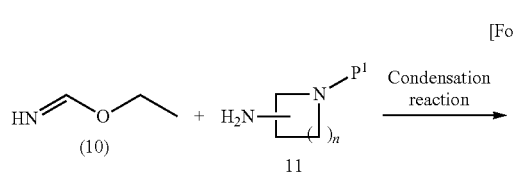

(10)    11

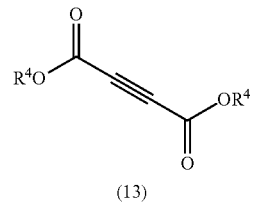

(13)

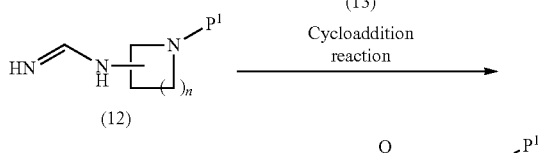

(12)

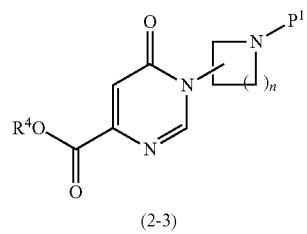

(2-3)

Compound (12) can be produced by the condensation reaction of compound (10) and compound (11).

Compound (2-3) can be produced by cycloaddition reaction using compound (12), compound (13), and a base. Examples of the base include triethylamine, N,N-diisopropylethylamine, and the like. Compound (10) and compound (11) can each be produced by a method known per se.

Of compounds (1), compound (1-5) can be produced by a method mentioned below from compound (1-4).

[Formula 17]

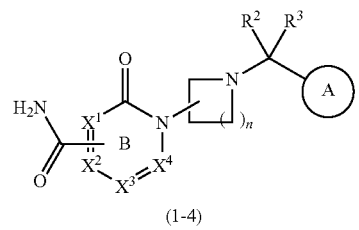

(1-4)

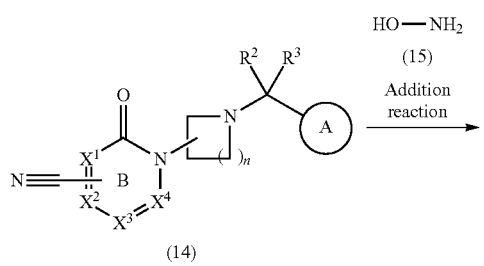

(14)

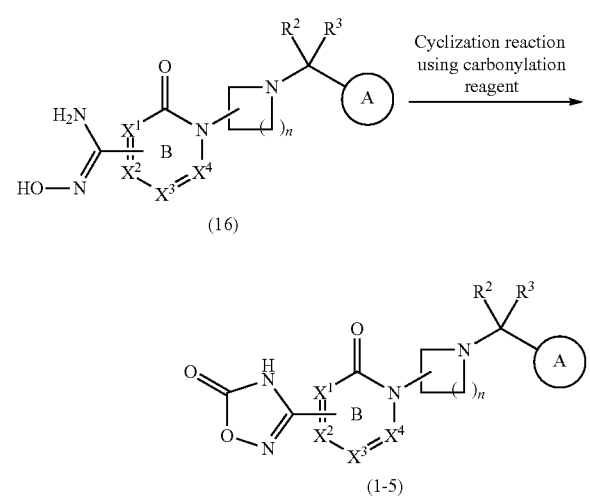

(1-5)

Compound (14) can be produced by dehydration reaction using compound (1-4), a dehydrating agent, and a base. Examples of the dehydrating agent include trifluoroacetic anhydride and the like. Examples of the base include triethylamine and the like.

Compound (16) can be produced by addition reaction using compound (15) and a base. Examples of the base include sodium bicarbonate and the like. A salt of compound (15) may be used.

Compound (1-5) can be produced by the cyclization reaction of compound (16) using a carbonylation reagent and a base. Examples of the carbonylation reagent include 1,1'-carbonylbis-1H-imidazole, diphosgene, triphosgene, phenyl chloroformate, and the like. Examples of the base include 1,8-diazabicyclo[5.4.0]unde-7-cene (DBU) and the like.

Compound (15) can be produced by a method known per se.

Of compounds (9), compound (9-1) can be produced by a method mentioned below from compound (17).

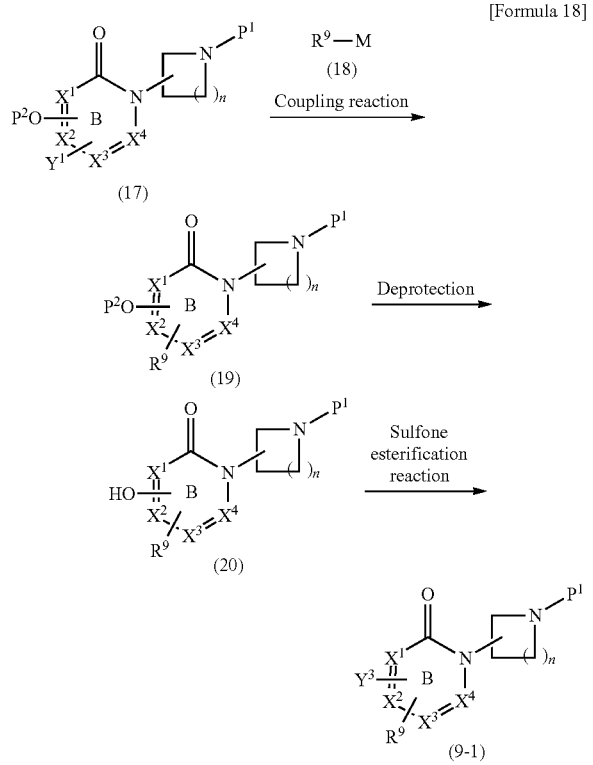

[Formula 18]

wherein $P^2$ represents a protecting group for the hydroxyl group; M represents boronic acid ($B(OR)_2$ or $B^-F_3K^+$) or zinc halide; $R^9$ represents $C_{1-6}$ alkyl, $C_{3-10}$ cycloalkyl, or vinyl; and $Y^3$ represents a sulfonate group. Compound (18) can be produced by a method known per se.

Of compounds (17), compound (17-1) can be produced by a method mentioned below from compound (8-1) and compound (7).

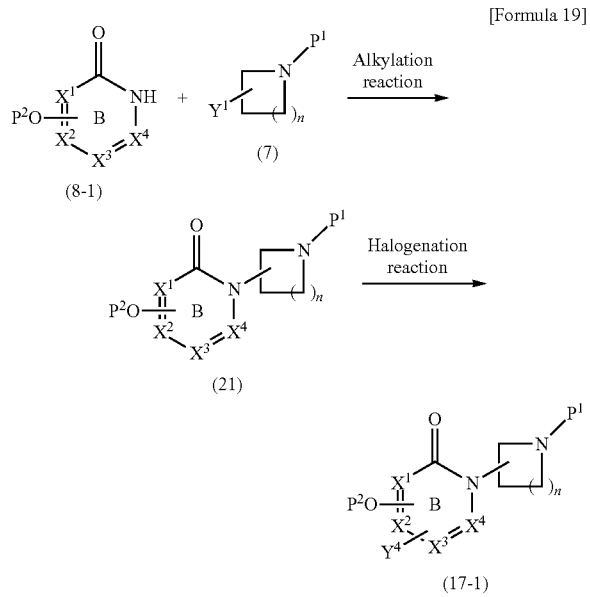

[Formula 19]

wherein $Y^4$ represents a halogen atom.

Compound (21) can be produced by alkylation reaction using compound (8-1), compound (7), and a base. Examples of the base include potassium carbonate, sodium carbonate, potassium tert-butoxide, and the like. Compound (8-1) can be produced by a method known per se.

Compound (17-1) can be produced by the halogenation reaction of compound (21) with a halogenating agent. Examples of the halogenating agent include N-iodosuccinimide (NIS), N-bromosuccinimide (NBS), N-chlorosuccinimide (NCS), iodine, bromine, sulfuryl chloride, and the like.

Of compounds (8), compound (8-2) can be produced by a method mentioned below from compound (22).

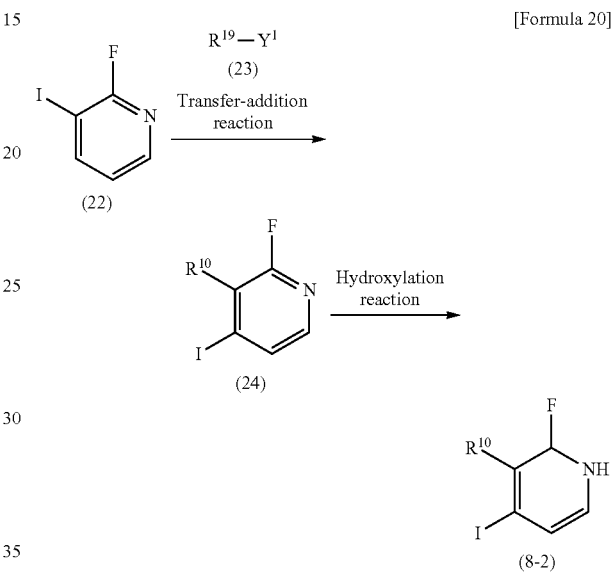

[Formula 20]

wherein $R^{10}$ represents $C_{1-6}$ alkyl or $C_{3-10}$ cycloalkyl.

Compound (24) can be produced by transfer-addition reaction using compound (22), a base, and compound (23). Examples of the base include lithium diisopropylamide, lithium hexamethyldisilazide, n-butyllithium, and the like. Compound (22) and (23) can each be produced by a method known per se.

Compound (8-2) can be produced by hydroxylation reaction using compound (24) and an acid. Examples of the acid include hydrochloric acid, sulfuric acid, and the like.

The present invention is explained in detail in the following by referring to the following Examples, Test Examples and Formulation Examples, which are not to be construed as limitative. In addition, the present invention may be modified without departing from the scope of invention.

The term "room temperature" in the following Examples indicates the range of generally from about 10 C to about 35 C. A ratio used for a mixed solvent indicates a volume ratio, unless otherwise specified. % indicates wt %, unless otherwise specified.

The term "NH" in silica gel column chromatography indicates that an aminopropylsilane-bound silica gel was used. The term "diol" in silica gel column chromatography indicates that a 3-(2,3-dihydroxypropoxy)propylsilane-bound silica gel was used. The term "C18" in HPLC (high-performance liquid chromatography) indicates that an octadecyl-bound silica gel was used. A ratio used for elution solvents indicates a volume ratio, unless otherwise specified.

Abbreviations described below are used in the following Examples.

THF: tetrahydrofuran
DMF: dimethylformamide
DMA: dimethylacetamide
DME: 1,2-dimethoxyethane
DMSO: dimethyl sulfoxide $^1$H NMR (proton nuclear magnetic resonance spectrum) was measured by Fourier transform type NMR. ACD/SpecManager (trade name) or the like was used in analysis. No mention was made about the very broad peaks of protons of a carboxy group, a hydroxyl group, an amino group, and the like.

Other abbreviations used herein indicate meanings described below.
s: singlet
d: doublet
t: triplet
q: quartet
quin: quintet
m: multiplet
br: broad
J: coupling constant
Hz: Hertz
CDCl$_3$: deuterated chloroform
DMSO-d$_6$: d$_6$-dimethyl sulfoxide
CD$_3$OD: deuterated methanol
$^1$H-NMR: proton nuclear magnetic resonance
TFA: trifluoroacetic acid MS (mass spectrum) was measured using LC/MS (liquid chromatograph mass spectrometer). ESI (ElectroSpray Ionization) or APCI (Atmospheric Pressure Chemical Ionization) was used as an ionization method. Both or either one of a positive mode (ESI+) and a negative mode (ESI−) was used as an ionization mode, and any data was described. Data was indicated by actual measurement value (found). In general, molecular ion peaks are observed. In the case of a compound having a tert-butoxycarbonyl group (-Boc), a fragment ion peak derived from the elimination of the tert-butoxycarbonyl group or the tert-butyl group (-tBu) may be observed. In the case of a compound having a hydroxyl group (—OH), a fragment ion peak derived from the elimination of H$_2$O may be observed. In the case of salt, a molecular ion peak or fragment ion peak of a free form is generally observed.

Example 1

1-(1-(4-Cyclobutyl-5-cyclopropyl-2-ethoxybenzyl) piperidin-4-yl)-2-oxo-1,2-dihydropyridine-4-carboxylic acid A) Methyl 2-(benzyloxy)-4-cyclobutylbenzoate Iodine (40 mg) and 1,2-dibromoethane (0.5 mL) were added to a mixture of magnesium (11.8 g) and anhydrous diethyl ether (250 mL), then bromocyclobutane (44.0 g) was slowly added thereto, and the mixture was stirred at 40C for 2 hours. A THF (450 mL) solution of zinc chloride (54 g) prepared at 160 C under high vacuum was added to the reaction mixture at 0 C, and the mixture was stirred at the same temperature as above for 1 hour. A mixture of methyl 2-(benzyloxy)-4-iodobenzoate (20 g), tris(dibenzylideneacetone)dipalladium(0) (4.97 g), 4,5-bis(diphenylphosphino)-9,9-dimethylxanthene (3.14 g), and THF (500 mL) was deaerated in an argon stream. The zinc reagent (350 mL) prepared above was added thereto, and the mixture was stirred overnight at 60 C. The reaction mixture was filtered through celite. The solvent was concentrated under reduced pressure. Water was added to the obtained residue, followed by extraction with ethyl acetate three times. Combined organic layers were washed with water and dried over anhydrous sodium sulfate, and then, the solvent was distilled off under reduced pressure. The obtained residue was purified by silica gel column chromatography (hexane/ethyl acetate) to obtain the title compound (9.5 g).

MS (ESI+): [M+H]$^+$ 297.3.

B) Methyl 2-(benzyloxy)-5-bromo-4-cyclobutylbenzoate

Sodium carbonate (7.51 g) was added to a dichloromethane (150 mL) solution of methyl 2-(benzyloxy)-4-cyclobutylbenzoate (14 g), then a dichloromethane (25 mL) solution of bromine (3.17 mL) was slowly added thereto at 10 C, and the mixture was stirred at the same temperature as above for 1 hour. A saturated aqueous solution of sodium bicarbonate was added to the reaction mixture, followed by extraction with ethyl acetate twice. The obtained organic layer was washed with a saturated aqueous solution of sodium bisulfite and saturated saline in this order and dried over anhydrous sodium sulfate, and then, the solvent was distilled off under reduced pressure. The obtained residue was purified by silica gel column chromatography (hexane/ethyl acetate) to obtain the title compound (12.2 g).

MS (ESI+): [M+H]$^+$ 375.1.

C) Methyl 2-(benzyloxy)-4-cyclobutyl-5-cyclopropylbenzoate

Cyclopropylboronic acid (6.18 g) and sodium carbonate (15.3 g) were added to a mixed solution of methyl 2-(benzyloxy)-5-bromo-4-cyclobutylbenzoate (13.5 g) in toluene (240 mL) and water (60 mL), and the mixture was deaerated for 20 minutes in an argon stream. Then, tris(dibenzylideneacetone)dipalladium(0) (6.25 g) and dicyclohexyl(2',6'-dimethoxybiphenyl-2-yl)phosphine (2.80 g) were added thereto, and the mixture was further deaerated for 5 minutes. The reaction mixture was stirred at 100 C for 16 hours. The reaction mixture was filtered through celite, and the celite was washed with ethyl acetate. Combined organic layers were washed with water and saturated saline in this order, and the solvent was distilled off under reduced pressure. The obtained residue was purified by silica gel column chromatography (hexane/ethyl acetate) to obtain the title compound (8.5 g).

MS (ESI+): [M+H]$^+$ 337.3.

D) Methyl 4-cyclobutyl-5-cyclopropyl-2-hydroxybenzoate

A methanol (100 mL) solution of methyl 2-(benzyloxy)-4-cyclobutyl-5-cyclopropylbenzoate (8.5 g) was deaerated for 20 minutes in a nitrogen stream. Then, 10% palladium carbon (containing 55% water, 1.1 g) was added thereto, and the mixture was stirred at room temperature for 3 hours in a hydrogen atmosphere. The reaction mixture was filtered through celite, and the solvent was distilled off under reduced pressure to obtain the title compound (6.0 g).

MS (ESI+): [M+H]$^+$ 247.2.

E) Methyl 4-cyclobutyl-5-cyclopropyl-2-ethoxybenzoate

Cesium carbonate (3.44 g) and iodoethane (0.55 mL) were added to a DMF (25 mL) solution of methyl 4-cyclobutyl-5-cyclopropyl-2-hydroxybenzoate (1.3 g) under ice cooling, and the mixture was stirred overnight at room temperature.

The reaction mixture was diluted with water, followed by extraction with ethyl acetate twice. Combined organic layers were washed with water and saturated saline in this order and dried over anhydrous sodium sulfate, and then, the solvent was distilled off under reduced pressure to obtain the title compound (1.2 g).

MS (ESI+): [M+H]$^+$ 275.5.

F) 4-Cyclobutyl-5-cyclopropyl-2-ethoxybenzaldehyde

Lithium aluminum hydride (1 M THF solution, 12.0 mL) was added at 0 C to a THF (50 mL) solution of methyl 4-cyclobutyl-5-cyclopropyl-2-ethoxybenzoate (3.0 g). The reaction mixture was stirred at room temperature for 2 hours. A saturated aqueous solution of sodium sulfate was added to the reaction mixture at 0 C, followed by extraction with ethyl acetate. Combined organic layers were washed with water and saturated saline in this order and dried over anhydrous sodium sulfate, and then, the solvent was distilled off under reduced pressure.

Manganese dioxide (8.4 g) was added in small portions at room temperature to an acetone (40 mL) solution of the obtained residue, and the mixture was stirred overnight at room temperature. The reaction mixture was filtered through celite, and the solvent was distilled off under reduced pressure. The obtained residue was purified by silica gel column chromatography (hexane/ethyl acetate) to obtain the title compound (1.8 g).

MS (ESI+): [M+H]$^+$ 245.5.

G) tert-Butyl 4-(4-bromo-2-oxopyridin-1(2H)-yl) piperidine-1-carboxylate

Potassium tert-butoxide (7.09 g) was added at room temperature to a mixture of 4-bromopyridin-2(1H)-one (10 g) in DME (287 mL). The reaction mixture was stirred at room temperature for 10 minutes. Then, potassium carbonate (15.9 g) and tert-butyl 4-(((4-methylphenyl)sulfonyl)oxy)piperidine-1-carboxylate (37.8 g) were added thereto, and the mixture was stirred at 85 C for 1 day, at 95 C for 1 day, and at 100 C for 1 day in a nitrogen atmosphere. Saturated saline was added to the reaction mixture, followed by extraction with ethyl acetate twice. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (14.7 g).

MS (ESI+): [M+H-tBu]$^+$ 301.1.

H) Methyl 1-(1-(tert-butoxycarbonyl)piperidin-4-yl)-2-oxo-1,2-dihydropyridine-4-carboxylate A mixture of tert-butyl 4-(4-bromo-2-oxopyridin-1(2H)-yl)piperidine-1-carboxylate (14.7 g), triethylamine (11.5 mL), methanol (50 mL), 1,1'-bis(diphenylphosphino)ferrocene-palladium(II) dichloride (3.01 g), and DMF (137 mL) was stirred at 80 C for 4 hours in a carbon monooxide atmosphere of 0.3 MPa. Water was added to the reaction mixture, followed by extraction with ethyl acetate twice. The obtained organic layer was washed with saturated saline twice and dried over anhydrous magnesium sulfate, and then, the solvent was distilled off under reduced pressure. The obtained residue was purified by silica gel column chromatography (hexane/ethyl acetate) and silica gel column chromatography (NH, hexane/ethyl acetate) to obtain the title compound (8.32 g).

MS (ESI+): [M+H-tBu]$^+$ 281.2.

I) Methyl 1-(1-(4-cyclobutyl-5-cyclopropyl-2-ethoxybenzyl)piperidin-4-yl)-2-oxo-1,2-dihydropyridine-4-carboxylate A mixture of methyl 1-(1-(tert-butoxycarbonyl)piperidin-4-yl)-2-oxo-1,2-dihydropyridine-4-carboxylate (500 mg) and formic acid (2 mL) was stirred at 70 C for 1 hour, and then, the solvent was distilled off under reduced pressure. 4-Cyclobutyl-5-cyclopropyl-2-ethoxybenzaldehyde (436 mg), THF (3 mL), and DMA (1 mL) were added to the obtained residue, and the mixture was stirred at room temperature for 10 minutes. Then, sodium triacetoxyborohydride (945 mg) was added thereto, and the mixture was stirred overnight at room temperature. A saturated aqueous solution of sodium bicarbonate was added to the reaction mixture, followed by extraction with ethyl acetate twice. Combined organic layers were washed with saturated saline and dried over anhydrous magnesium sulfate, and the solvent was distilled off under reduced pressure. The obtained residue was purified by silica gel column chromatography (hexane/ethyl acetate) to obtain the title compound (567 mg).

MS (ESI+): [M+H]$^+$ 465.4.

J) 1-(1-(4-Cyclobutyl-5-cyclopropyl-2-ethoxybenzyl)piperidin-4-yl)-2-oxo-1,2-dihydropyridine-4-carboxylic acid A mixture of methyl 1-(1-(4-cyclobutyl-5-cyclopropyl-2-ethoxybenzyl)piperidin-4-yl)-2-oxo-1,2-dihydropyridine-4-carboxylate (567 mg), a 1 M aqueous sodium hydroxide solution (3 mL), and ethanol (3 mL) was stirred at 70 C for 2 hours. The reaction mixture was pH-adjusted to 4 using 1 M hydrochloric acid and stirred at room temperature for 30 minutes. The resulting solid was collected by filtration and recrystallized (DMSO/ethanol) to obtain the title compound (358 mg).

$^1$H NMR (300 MHz, DMSO-d$_6$) delta 0.45-0.55 (2H, m), 0.80-0.91 (2H, m), 1.33 (3H, t, J=6.9 Hz), 1.66-2.39 (13H, m), 2.97 (2H, d, J=11.5 Hz), 3.51 (2H, s), 3.76-3.95 (1H, m), 4.05 (2H, q, J=7.0 Hz), 4.53-4.74 (1H, m), 6.55 (1H, dd, J=7.1, 1.8 Hz), 6.81 (2H, d, J=2.3 Hz), 6.90 (1H, s), 7.84 (1H, d, J=7.3 Hz).

Example 2

1-(1-((5-Cyclopropyl-6-(4-fluorophenyl)-2-isopropoxypyridin-3-yl)methyl)piperidin-4-yl)-2-oxo-1,2-dihydropyridin-4-carboxylic acid A) 6-(4-Fluorophenyl)-2-hydroxynicotinonitrile 2-Cyanoacetamide (4.31 g) and 3-(dimethylamino)-1-(4-fluorophenyl)prop-2-en-1-one (9.00 g) were added in this order to a mixture of sodium hydride (60% oil, 4.10 g) and DMF (90 mL), and the resultant mixture was stirred at 105 C for 2 hours. The solvent was distilled off. Water was added to the obtained residue, and then, the mixture was rendered acidic by the addition of acetic acid and stirred at 70 C for 15 minutes. Methanol was added to the reaction mixture for suspension, and the deposited solid was washed with ethyl acetate to obtain the title compound (9.98 g).

¹H NMR (300 MHz, DMSO-d₆) delta 6.78 (1H, d, J=7.2 Hz), 7.38 (2H, t, J=8.9 Hz), 7.89 (2H, dd, J=8.8, 5.4 Hz), 8.19 (1H, d, J=7.6 Hz).

B) 5-Bromo-6-(4-fluorophenyl)-2-hydroxynicotinonitrile

N-Bromosuccinimide (3.66 g) was added to a mixture of 6-(4-fluorophenyl)-2-hydroxynicotinonitrile (4.00 g), THF (30 mL), and methanol (30 mL), and the resultant mixture was stirred at room temperature for 10 minutes. The solvent was distilled off, and the obtained residue was suspended in a mixed solvent of water, ethyl acetate, and hexane. Then, the obtained solid was washed with hexane to obtain the title compound (5.18 g).
¹H NMR (300 MHz, DMSO-d₆) delta 7.28-7.44 (2H, m), 7.63 (2H, dd, J=8.6, 5.5 Hz), 8.54 (1H, s), 13.11 (1H, brs).

C) 5-Bromo-6-(4-fluorophenyl)-2-isopropoxynicotinonitrile

2-Bromopropane (3.32 mL) was added to a mixture of 5-bromo-6-(4-fluorophenyl)-2-hydroxynicotinonitrile (5.18 g), potassium carbonate (4.89 g), and DMF (30 mL), and the resultant mixture was stirred at 80 C for 30 minutes. Water was added to the reaction mixture, followed by extraction with ethyl acetate. The organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (5.92 g)
¹H NMR (300 MHz, CDCl₃) delta 1.41 (6H, d, J=6.2 Hz), 5.27-5.56 (1H, m), 7.16 (2H, t, J=8.7 Hz), 7.66-7.82 (2H, m), 8.08 (1H, s).

D) Methyl 5-bromo-6-(4-fluorophenyl)-2-isopropoxynicotinate

An 8 M aqueous potassium hydroxide solution (22.1 mL) was added to a mixture of 5-bromo-6-(4-fluorophenyl)-2-isopropoxynicotinonitrile (5.92 g) and ethanol (50 mL), and the resultant mixture was stirred overnight at 100 C. The reaction mixture was neutralized with 6 M hydrochloric acid at 0 C, followed by extraction with ethyl acetate. The organic layer was dried over anhydrous magnesium sulfate, and then, the solvent was distilled off under reduced pressure. Potassium carbonate (4.88 g) and iodomethane (1.66 mL) were added to a mixture of the obtained residue and DMF (30 mL), and the mixture was stirred at 60 C for 30 minutes. Water was added to the reaction mixture, followed by extraction with ethyl acetate. The organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (3.65 g).
¹H NMR (300 MHz, CDCl₃) delta 1.40 (6H, d, J=6.1 Hz), 3.91 (3H, s), 5.35-5.51 (1H, m), 7.14 (2H, t, J=8.7 Hz), 7.78 (2H, dd, J=8.9, 5.4 Hz), 8.38 (1H, s).

E) Methyl 5-cyclopropyl-6-(4-fluorophenyl)-2-isopropoxynicotinate

Tris(dibenzylideneacetone)dipalladium(0) (635 mg) was added to a mixture of methyl 5-bromo-6-(4-fluorophenyl)-2-isopropoxynicotinate (3.65 g), cyclopropylboronic acid (2.55 g), dicyclohexyl(2',6'-dimethoxybiphenyl-2-yl)phosphine (610 mg), a 2 M aqueous sodium carbonate solution (14.9 mL), and toluene (25 mL), and the resultant mixture was stirred at 100 C for 2 hours in an argon atmosphere. The reaction mixture was allowed to cool to room temperature and poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (3.18 g).
¹H NMR (300 MHz, CDCl₃) delta 0.60-0.68 (2H, m), 0.79-0.99 (2H, m), 1.39 (6H, d, J=6.1 Hz), 1.87-2.00 (1H, m), 3.89 (3H, s), 5.37-5.53 (1H, m), 7.14 (2H, t, J=8.7 Hz), 7.71-7.80 (2H, m), 7.82 (1H, s).

F) 5-Cyclopropyl-6-(4-fluorophenyl)-2-isopropoxynicotinaldehyde

A THF (20 mL) solution of methyl 5-cyclopropyl-6-(4-fluorophenyl)-2-isopropoxynicotinate (3.17 g) was added to a THF (20 mL) suspension of lithium aluminum hydride (365 mg) under ice cooling in a nitrogen atmosphere. After stirring at the same temperature as above for 30 minutes, water (0.35 mL) and a 15% aqueous sodium hydroxide solution (0.35 mL) were added thereto, and the mixture was stirred for 5 minutes. Then, water (1.05 mL) was further added thereto. The reaction mixture was stirred for 30 minutes and then filtered. The filtrate was concentrated under reduced pressure. Manganese dioxide (8.36 g) was added to a toluene (30 mL) solution of the obtained residue, and the mixture was stirred at 60 C for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (2.45 g)
¹H NMR (300 MHz, CDCl₃) delta 0.58-0.72 (2H, m), 0.87-0.99 (2H, m), 1.40 (6H, d, J=6.2 Hz), 1.81-2.01 (1H, m), 5.35-5.66 (1H, m), 7.15 (2H, t, J=8.7 Hz), 7.69-7.84 (3H, m), 10.36 (1H, s).

G) Methyl 1-(1-((5-cyclopropyl-6-(4-fluorophenyl)-2-isopropoxypyridin-3-yl)methyl)piperidin-4-yl)-2-oxo-1,2-dihydropyridin-4-carboxylate The mixture of Methyl 1-(1-(tert-butoxycarbonyl)piperidin-4-yl)-2-oxo-1,2-dihydropyridin-4-carboxylate (150 mg) and formic acid was stirred at 70 C for 1 hour. Then, the solvent was distilled off under reduced pressure. 5-Cyclopropyl-6-(4-fluorophenyl)-2-isopropoxynicotinaldehyde (174 mg) and THF (2 mL) were added to the obtained residue, and the mixture was stirred at room temperature for 10 minutes. Then, sodium triacetoxyborohydride (378 mg) was added thereto, and the mixture was stirred overnight at room temperature. A saturated aqueous solution of sodium bicarbonate was added to the reaction mixture, followed by extraction with ethyl acetate twice. The obtained organic layer was washed with saturated saline and dried over anhydrous magnesium sulfate, and the solvent was distilled off under reduced pressure. The obtained residue was purified by silica gel column chromatography (hexane/ethyl acetate) to obtain the title compound (189 mg).
MS (ESI+): [M+H]⁺ 520.4.

H) 1-(1-((5-Cyclopropyl-6-(4-fluorophenyl)-2-isopropoxypyridin-3-yl)methyl)piperidin-4-yl)-2-oxo-1,2-dihydropyridine-4-carboxylic acid A mixture of methyl 1-(1-((5-cyclopropyl-6-(4-fluorophenyl)-2-isopropoxypyridin-3-yl)methyl)piperidin-4-yl)-2- oxo-1,2-dihydropyridine-4-carboxylate (189 mg), a 1 M aqueous sodium hydroxide solution (1.5 mL), and ethanol (3 mL) was stirred at 70 C for 1 hour. The obtained reaction mixture was neutralized with 1 M hydrochloric acid and stirred overnight at room temperature. The resulting solid was collected by filtration and recrystallized (ethanol/ethyl acetate) to obtain the title compound (91 mg).

$^1$H NMR (300 MHz, DMSO-$d_6$) delta 0.57 (2H, d, J=5.7 Hz), 0.87 (2H, d, J=6.7 Hz), 1.30 (6H, d, J=6.1 Hz), 1.68-1.78 (2H, m), 1.82-1.98 (3H, m), 2.24 (2H, d, J=17.3 Hz), 2.99 (2H, d, J=9.0 Hz), 3.51 (2H, s), 4.64 (1H, d, J=11.4 Hz), 5.19-5.32 (1H, m), 6.57 (1H, d, J=6.9 Hz), 6.83 (1H, d, J=1.5 Hz), 7.29 (2H, t, J=8.9 Hz), 7.37 (1H, s), 7.74 (2H, dd, J=8.7, 5.7 Hz), 7.90 (1H, d, J=6.9 Hz).

Example 3

1-(1-((2-Cyclopropyl-4'-fluoro-5-isopropoxybiphenyl-4-yl)methyl)piperidin-4-yl)-2-oxo-1,2-dihydropyridin-4-carboxylic acid A) Methyl 4-iodo-2-isopropoxybenzoate 2-Bromopropane (6.49 mL) was added to a DMF (70 mL) suspension of methyl 2-hydroxy-4-iodobenzoate (12.8 g) and potassium carbonate (12.7 g), and the mixture was stirred at 60 C for 2 hours. The reaction mixture was allowed to cool to room temperature, and then, water was added thereto, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (NH, hexane/ethyl acetate) to obtain the title compound (14.0 g).

$^1$H NMR (300 MHz, CDCl$_3$) delta 1.37 (6H, d, J=6.0 Hz), 3.86 (3H, s), 4.41-4.67 (1H, m), 7.29-7.35 (2H, m), 7.46 (1H, d, J=8.6 Hz).

B) Methyl 4'-fluoro-3-isopropoxybiphenyl-4-carboxylate

A mixture of methyl 4-iodo-2-isopropoxybenzoate (7.50 g), (4-fluorophenyl)boronic acid (6.56 g), dicyclohexyl(2',6'-dimethoxybiphenyl-2-yl)phosphine (1.44 g), a 2 M aqueous sodium carbonate solution (35.1 mL), tris(dibenzylideneacetone)dipalladium(0) (1.50 g), and toluene (50 mL) was stirred at 100 C for 2 hours in an argon atmosphere. The reaction mixture was allowed to cool to room temperature. Then, the organic layer was separated and passed through a short silica gel (NH) column, and the solvent was distilled off under reduced pressure. The obtained residue was purified by silica gel column chromatography (hexane/ethyl acetate) to obtain the title compound (6.61 g).

$^1$H NMR (300 MHz, CDCl$_3$) delta 1.41 (6H, d, J=6.0 Hz), 3.90 (3H, s), 4.56-4.78 (1H, m), 7.07-7.19 (4H, m), 7.49-7.59 (2H, m), 7.80-7.90 (1H, m).

C) Methyl 2-bromo-4'-fluoro-5-isopropoxybiphenyl-4-carboxylate

Dibromoisocyanuric acid (4.60 g) was added to a mixture of methyl 4'-fluoro-3-isopropoxybiphenyl-4-carboxylate (6.61 g) and DMF (60 mL), and the resultant mixture was stirred at room temperature for 5 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (7.53 g).

$^1$H NMR (300 MHz, CDCl$_3$) delta 1.37 (6H, d, J=6.0 Hz), 3.90 (3H, s), 4.45-4.69 (1H, m), 6.91 (1H, s), 7.06-7.18 (2H, m), 7.32-7.44 (2H, m), 8.05 (1H, s).

D) (2-Cyclopropyl-4'-fluoro-5-isopropoxybiphenyl-4-yl)methanol

A mixture of methyl 2-bromo-4'-fluoro-5-isopropoxybiphenyl-4-carboxylate (7.53 g), cyclopropylboronic acid (4.40 g), dicyclohexyl(2',6'-dimethoxybiphenyl-2-yl)phosphine (1.26 g), a 2 M aqueous sodium carbonate solution (30.8 mL), tris(dibenzylideneacetone)dipalladium(0) (1.31 g), and toluene (150 mL) was stirred overnight at 100 C in an argon atmosphere. The reaction mixture was allowed to cool to room temperature. Then, the organic layer was separated, washed with saturated saline, and passed through a short silica gel (NH) column, and the solvent was distilled off under reduced pressure. A THF (50 mL) solution of the obtained residue was added to a THF (50 mL) suspension of lithium aluminum hydride (2.00 g) under ice cooling in a nitrogen atmosphere. After stirring at the same temperature as above for 30 minutes, water (2 mL) and a 15% aqueous sodium hydroxide solution (2 mL) were added thereto, and the mixture was stirred for 5 minutes. Water (6 mL) was further added to the reaction mixture, and the mixture was stirred for 30 minutes and then filtered. The filtrate was concentrated under reduced pressure. The obtained residue was purified by silica gel column chromatography (hexane/ethyl acetate) to obtain the title compound (5.75 g).

$^1$H NMR (300 MHz, CDCl$_3$) delta 0.55-0.64 (2H, m), 0.68-0.83 (2H, m), 1.31-1.40 (6H, m), 1.67-1.89 (1H, m), 2.45 (1H, t, J=6.6 Hz), 4.51-4.64 (1H, m), 4.66 (2H, d, J=6.6 Hz), 6.73 (1H, s), 6.86 (1H, s), 7.05-7.15 (2H, m), 7.34-7.45 (2H, m).

E) 2-Cyclopropyl-4'-fluoro-5-isopropoxybiphenyl-4-carbaldehyde

Manganese dioxide (16.6 g) was added to a toluene (80 mL) solution of (2-cyclopropyl-4'-fluoro-5-isopropoxybiphenyl-4-yl)methanol (5.75 g), and the mixture was stirred at 60 C for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (4.54 g).

$^1$H NMR (300 MHz, CDCl$_3$) delta 0.61-0.72 (2H, m), 0.75-0.85 (2H, m), 1.39 (6H, d, J=6.0 Hz), 1.71 (1H, tt, J=8.4, 5.4 Hz), 4.54-4.76 (1H, m), 6.83 (1H, s), 7.07-7.20 (2H, m), 7.35-7.50 (3H, m), 10.46 (1H, s).

F) Methyl 1-(1-((2-Cyclopropyl-4'-fluoro-5-isopropoxybiphenyl-4-yl)methyl)piperidin-4-yl)-2-oxo-1,2-dihydropyridin-4-carboxylate A mixture of methyl 1-(1-(tert-butoxycarbonyl)piperidin-4-yl)-2-oxo-1,2-dihydropyridin-4-carboxylate (170 mg) and formic acid (2 mL) was added, and the mixture was stirred at 70 C for 1 hour. Then, the solvent was distilled off. 2-Cyclopropyl-4'-fluoro-5-isopropoxybiphenyl-4-carbaldehyde (181 mg) and THF (2 mL) were added to the obtained residue, and the mixture was stirred at room temperature for 10 minutes. Then, sodium triacetoxyborohydride (428 mg) was added thereto, and the mixture was stirred overnight at room temperature. A saturated aqueous solution of sodium bicarbonate was added to the obtained reaction solution, followed by extraction with ethyl acetate twice. The obtained organic layer was washed with saturated saline and dried over anhydrous magnesium sulfate, and the solvent was distilled off under reduced pressure. The obtained residue was purified by silica gel column chromatography (hexane/ethyl acetate) to obtain the title compound (103 mg).

MS (ESI+): [M+H]$^+$ 519.4.

G) 1-(1-((2-Cyclopropyl-4'-fluoro-5-isopropoxybiphenyl-4-yl)methyl)piperidin-4-yl)-2-oxo-1,2-dihydropyridine-4-carboxylic acid A mixed solution of methyl 1-(1-((2-cyclopropyl-4'-fluoro-5-isopropoxybiphenyl-4-yl)methyl)piperidin-4-yl)-2-oxo-1,2-dihydropyridine-4-carboxylate (103 mg), a 1 M aqueous sodium hydroxide solution (1 mL), and ethanol (2 mL) was stirred at 70 C for 1 hour. The obtained reaction solution was neutralized with 1 M hydrochloric acid and, in this state, stirred at room temperature for 3 hours. The resulting solid was collected by filtration and recrystallized (ethyl acetate) to obtain the title compound (70.3 mg).

$^1$H NMR (300 MHz, DMSO-d$_6$) delta 0.49-0.59 (2H, m), 0.71-0.84 (2H, m), 1.26 (6H, d, J=5.9 Hz), 1.67-1.79 (3H, m), 1.89 (2H, d, J=10.9 Hz), 2.22 (2H, t, J=12.6 Hz), 3.02 (2H, d, J=11.0 Hz), 3.55 (2H, s), 4.54-4.73 (2H, m), 6.57 (1H, dd, J=7.1, 1.8 Hz), 6.78 (1H, s), 6.82 (1H, d, J=1.7 Hz), 6.98 (1H, s), 7.27 (2H, t, J=8.9 Hz), 7.49 (2H, dd, J=8.7, 5.7 Hz), 7.87 (1H, d, J=7.3 Hz).

Example 4

1-(1-(4,5-Dicyclopropyl-2-isopropoxybenzyl)piperidin-4-yl)-2-oxo-1,2-dihydropyridine-4-carboxylic acid

A) Methyl 4-iodo-2-isopropoxybenzoate

2-Iodopropane (6.42 g) was added at room temperature to a mixture of methyl 2-hydroxy-4-iodobenzoate (7.00 g), potassium carbonate (6.96 g), and DMF (100 mL), and the resultant mixture was stirred at 70 C for 2 days in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (7.92 g)

$^1$H NMR (300 MHz, CDCl$_3$) delta 1.37 (6H, d, J=6.0 Hz), 3.86 (3H, s), 4.49-4.63 (1H, m), 7.28-7.33 (2H, m), 7.46 (1H, d, J=8.5 Hz).

B) Methyl 4-cyclopropyl-2-isopropoxybenzoate

Cyclopropylboronic acid (3.19 g), a 2 M aqueous sodium carbonate solution (37 mL), tris(dibenzylideneacetone)dipalladium(0) (1.59 g), and dicyclohexyl(2',6'-dimethoxybiphenyl-2-yl)phosphine (1.52 g) were added at room temperature to a toluene (100 mL) solution of methyl 4-iodo-2-isopropoxybenzoate (7.92 g), and the mixture was stirred at 100 C for 15 hours in an argon atmosphere. Water was added to the reaction mixture at room temperature. The mixture was filtered through celite, and then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (5.43 g).

$^1$H NMR (300 MHz, CDCl$_3$) delta 0.70-0.76 (2H, m), 0.98-1.05 (2H, m), 1.36 (6H, d, J=6.1 Hz), 1.82-1.93 (1H, m), 3.85 (3H, s), 4.49-4.63 (1H, m), 6.62 (1H, dd, J=8.1, 1.6 Hz), 6.69 (1H, d, J=1.5 Hz), 7.69 (1H, d, J=8.1 Hz).

C) Methyl 5-bromo-4-cyclopropyl-2-isopropoxybenzoate

Dibromoisocyanuric acid (3.99 g) was added at room temperature to a DMF (80 mL) solution of methyl 4-cyclopropyl-2-isopropoxybenzoate (5.43 g), and the mixture was stirred at 90 C for 1 hour in a nitrogen atmosphere. An aqueous sodium thiosulfate solution was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (6.89 g).

$^1$H NMR (300 MHz, CDCl$_3$) delta 0.65-0.72 (2H, m), 1.04-1.11 (2H, m), 1.34 (6H, d, J=6.1 Hz), 2.12-2.23 (1H, m), 3.86 (3H, s), 4.42-4.56 (1H, m), 6.50 (1H, s), 7.96 (1H, s).

D) Methyl 4,5-dicyclopropyl-2-isopropoxybenzoate

Cyclopropylboronic acid (2.83 g), a 2 M aqueous sodium carbonate solution (33 mL), tris(dibenzylideneacetone)dipalladium(0) (1.41 g), and dicyclohexyl(2',6'-dimethoxybiphenyl-2-yl)phosphine (1.36 g) were added at room temperature to a toluene (100 mL) solution of methyl 5-bromo-4-cyclopropyl-2-isopropoxybenzoate (6.89 g), and the mixture was stirred at 100 C for 15 hours in an argon atmosphere. Water was added to the reaction mixture at room temperature. The mixture was filtered through celite, and then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (5.90 g)

$^1$H NMR (300 MHz, CDCl$_3$) delta 0.62-0.72 (4H, m), 0.88-0.96 (2H, m), 0.98-1.06 (2H, m), 1.33 (6H, d, J=6.1 Hz), 1.99-2.11 (1H, m), 2.21-2.32 (1H, m), 3.85 (3H, s), 4.40-4.53 (1H, m), 6.51 (1H, s), 7.43 (1H, d, J=0.4 Hz).

E) (4,5-Dicyclopropyl-2-isopropoxyphenyl)methanol

A THF (15 mL) solution of methyl 4,5-dicyclopropyl-2-isopropoxybenzoate (5.90 g) was added at 0 C to a mixture of lithium aluminum hydride (1.71 g) and THF (85 mL), and the resultant mixture was stirred at room temperature for 30 minutes in a nitrogen atmosphere. Water (1.8 mL), a 1 M aqueous sodium hydroxide solution (1.8 mL), and water (5.4 mL) were added in this order to the reaction mixture at 0 C. The mixture was filtered through celite, and then, the filtrate was concentrated under reduced pressure. The obtained residue was purified by silica gel chromatography (hexane/ethyl acetate) to obtain the title compound (5.22 g).

$^1$H NMR (300 MHz, CDCl$_3$) delta 0.59-0.68 (4H, m), 0.86-1.00 (4H, m), 1.33 (6H, d, J=6.0 Hz), 2.02-2.13 (1H, m), 2.15-2.27 (1H, m), 2.41 (1H, t, J=6.5 Hz), 4.48-4.64 (3H, m), 6.49 (1H, s), 6.86 (1H, s).

F) 4,5-Dicyclopropyl-2-isopropoxybenzaldehyde

Manganese dioxide (14.7 g) was added at room temperature to a toluene (80 mL) solution of (4,5-dicyclopropyl-2-isopropoxyphenyl)methanol (5.22 g), and the mixture was stirred at 80 C for 1 hour in a nitrogen atmosphere. The reaction mixture was filtered through celite, and then, the filtrate was concentrated. The obtained residue was purified by silica gel column chromatography (hexane/ethyl acetate) to obtain the title compound (4.88 g).
$^1$H NMR (300 MHz, CDCl$_3$) delta 0.64-0.76 (4H, m), 0.88-0.96 (2H, m), 1.03-1.11 (2H, m), 1.36 (6H, d, J=6.0 Hz), 1.98-2.09 (1H, m), 2.25-2.37 (1H, m), 4.53-4.66 (1H, m), 6.49 (1H, s), 7.47 (1H, d, J=0.6 Hz), 10.37 (1H, s).

G) Methyl 1-(1-(4,5-dicyclopropyl-2-isopropoxybenzyl)piperidin-4-yl)-2-oxo-1,2-dihydropyridine-4-carboxylate A mixture of methyl 1-(1-(tert-butoxycarbonyl)piperidin-4-yl)-2-oxo-1,2-dihydropyridine-4-carboxylate (536 mg) in formic acid (8 mL) was stirred at 70 C for 30 minutes in a nitrogen atmosphere, and then, the solvent was distilled off under reduced pressure. Sodium triacetoxyborohydride (676 mg) was added to a mixture of the obtained residue and 4,5-dicyclopropyl-2-isopropoxybenzaldehyde (476 mg) in THF (10 mL), and the mixture was stirred at room temperature for 15 hours in a nitrogen atmosphere. A saturated aqueous solution of sodium bicarbonate was added to the reaction mixture, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (429 mg).
MS (ESI+): [M+H]$^+$ 465.3.

H) 1-(1-(4,5-Dicyclopropyl-2-isopropoxybenzyl) piperidin-4-yl)-2-oxo-1,2-dihydropyridine-4-carboxylic acid A 2 M aqueous sodium hydroxide solution (3 mL) was added to an ethanol (8 mL) solution of methyl 1-(1-(4,5-dicyclopropyl-2-isopropoxybenzyl)piperidin-4-yl)-2-oxo-1,2-dihydropyridine-4-carboxylate (426 mg), and the mixture was stirred at 90 C for 2 hours in a nitrogen atmosphere. The solvent in the reaction mixture was distilled off under reduced pressure. The obtained residue was dissolved in water, and the solution was neutralized with 2 M hydrochloric acid. The resulting solid was collected by filtration and dissolved in ethyl acetate and THF. The solvent in the obtained solution was distilled off under reduced pressure. The obtained residue was crystallized (ethyl acetate/hexane) and recrystallized (ethanol/hexane) to obtain the title compound (286 mg).
$^1$H NMR (300 MHz, DMSO-d$_6$) delta 0.53-0.59 (2H, m), 0.62-0.69 (2H, m), 0.85-0.98 (4H, m), 1.23 (6H, d, J=5.9 Hz), 1.67-1.79 (2H, m), 1.82-1.98 (2H, m), 2.01-2.12 (1H, m), 2.14-2.34 (3H, m), 3.00 (2H, d, J=11.4 Hz), 3.53 (2H, s), 4.48-4.75 (2H, m), 6.47 (1H, s), 6.57 (1H, dd, J=7.2, 1.8 Hz), 6.81 (1H, d, J=1.7 Hz), 6.94 (1H, s), 7.82 (1H, d, J=7.2 Hz).

Example 5

1-(1-((2-Chloro-6-cyclopropyl-2',4'-difluoro-3-isopropoxybiphenyl-4-yl)methyl)piperidin-4-yl)-2-oxo-1,2-dihydropyridine-4-carboxylic acid A) Methyl 3-(benzyloxy)-2',4'-difluorobiphenyl-4-carboxylate A mixture of methyl 2-hydroxy-4-iodobenzoate (22 g), 2,4-difluorophenylboronic acid (25 g), a 2 M aqueous sodium carbonate solution (119 mL), tris(dibenzylideneacetone)dipalladium(0) (5.07 g), and dicyclohexyl(2',6'-dimethoxybiphenyl-2-yl)phosphine (4.87 g) in toluene (150 mL) was stirred at 100 C for 2 hours. The reaction mixture was poured to water, and the mixture was filtered through celite. Then, the filtrate was subjected to extraction with ethyl acetate. The obtained organic layer was washed with saturated saline and passed through a basic silica gel, and the solvent was distilled off under reduced pressure. Benzyl bromide (10.4 mL) was added at room temperature to a mixture of the obtained residue, potassium carbonate (21.9 g), and DMF (100 mL), and the mixture was stirred at 70 C for 1 hour in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (30.5 g)
$^1$H NMR (300 MHz, CDCl$_3$) delta 3.92 (3H, s), 5.22 (2H, s), 6.85-7.02 (2H, m), 7.09-7.19 (2H, m), 7.28-7.45 (3H, m), 7.47-7.56 (2H, m), 7.62 (1H, dd, J=6.8, 2.9 Hz), 7.90 (1H, d, J=8.0 Hz).

B) Methyl 5-(benzyloxy)-2-bromo-2',4'-difluorobiphenyl-4-carboxylate

Dibromoisocyanuric acid (15.9 g) was added at room temperature to a DMF (150 mL) solution of methyl 3-(benzyloxy)-2',4'-difluorobiphenyl-4-carboxylate (28.0 g), and the mixture was stirred overnight at room temperature. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (34.0 g)
$^1$H NMR (300 MHz, CDCl$_3$) delta 3.92 (3H, s), 5.15 (2H, s), 6.87-7.01 (3H, m), 7.10-7.55 (6H, m), 8.11 (1H, s).

C) Methyl 5-(benzyloxy)-2-cyclopropyl-2',4'-difluorobiphenyl-4-carboxylate

A mixture of methyl 5-(benzyloxy)-2-bromo-2',4'-difluorobiphenyl-4-carboxylate (34.3 g), cyclopropylboronic acid (17.0 g), a 2 M aqueous sodium carbonate solution (119 mL), tris(dibenzylideneacetone)dipalladium(0) (5.07 g), and dicyclohexyl(2',6'-dimethoxybiphenyl-2-yl)phosphine (4.87 g) in toluene (150 mL) was stirred overnight at 100 C. The reaction mixture was poured to water, followed by extraction with ethyl acetate. The obtained organic layer was washed with saturated saline and passed through a basic silica gel, and the solvent was distilled off under reduced pressure. The obtained residue was purified by silica gel column chromatography (hexane/ethyl acetate) to obtain the title compound (20.3 g)

$^1$H NMR (300 MHz, CDCl$_3$) delta 0.54-0.63 (2H, m), 0.70-0.80 (2H, m), 1.59-1.72 (1H, m), 3.87-3.93 (3H, m), 5.14 (2H, s), 6.83-7.01 (3H, m), 7.18-7.41 (4H, m), 7.44-7.51 (3H, m).

D) Methyl 2-cyclopropyl-2',4'-difluoro-5-hydroxybiphenyl-4-carboxylate

A mixture of methyl 5-(benzyloxy)-2-cyclopropyl-2',4'-difluorobiphenyl-4-carboxylate (20.3 g), 10% palladium carbon (containing 55% water, 10.0 g), and THF (100 mL) was stirred at room temperature for 1 hour in a hydrogen atmosphere of balloon pressure. The catalyst was filtered off, and the solvent was distilled off under reduced pressure. The obtained residue was purified by silica gel column chromatography (hexane/ethyl acetate) to obtain the title compound (15.0 g).

MS (ESI+): [M+H]$^+$ 305.2.

E) Methyl 2-chloro-6-cyclopropyl-2',4'-difluoro-3-isopropoxybiphenyl-4-carboxylate N-Chlorosuccinimide (1.58 g) was added in small portions at room temperature to a DMF (30 mL) solution of methyl 2-cyclopropyl-2',4'-difluoro-5-hydroxybiphenyl-4-carboxylate (3.0 g), and then, the mixture was stirred at room temperature for 2 hours. Water was added to the reaction mixture at room temperature, followed by extraction with ethyl acetate. The obtained organic layer was washed with saturated saline twice and dried over anhydrous magnesium sulfate, and then, the solvent was distilled off under reduced pressure. 2-Iodopropane (2.95 mL) was added to a mixture of the obtained residue, potassium carbonate (4.09 g), and DMF (40 mL), and the mixture was stirred at 80 C for 1 hour. Water was added to the reaction mixture, followed by extraction with ethyl acetate. The obtained organic layer was washed with saturated saline twice and dried over anhydrous magnesium sulfate, and then, the solvent was distilled off under reduced pressure. The obtained residue was purified by silica gel column chromatography (hexane/ethyl acetate) to obtain the title compound (3.10 g)

$^1$H NMR (300 MHz, CDCl$_3$) delta 0.54-0.68 (2H, m), 0.70-0.78 (2H, m), 1.32 (6H, d, J=6.1 Hz), 1.43-1.54 (1H, m), 3.89-3.96 (3H, m), 4.26-4.46 (1H, m), 6.86-7.03 (2H, m), 7.13-7.23 (1H, m), 7.28 (1H, s).

F) (2-Chloro-6-cyclopropyl-2',4'-difluoro-3-isopropoxybiphenyl-4-yl)methanol Diisobutylaluminum hydride (1.5 M toluene solution, 16.3 mL) was added at 0 C to a THF (30 mL) solution of methyl 2-chloro-6-cyclopropyl-2',4'-difluoro-3-isopropoxybiphenyl-4-carboxylate (3.10 g), and then, the mixture was stirred at 0 C for 20 minutes in a nitrogen atmosphere. Sodium sulfate decahydrate was added to the reaction mixture, and the mixture was stirred for 1 hour. After filtration, the solvent was distilled off under reduced pressure. The obtained residue was purified by silica gel column chromatography (hexane/ethyl acetate) to obtain the title compound (2.18 g).

$^1$H NMR (300 MHz, CDCl$_3$) delta 0.50-0.76 (4H, m), 1.35 (6H, dd, J=6.1, 4.6 Hz), 1.42-1.55 (1H, m), 2.16-2.34 (1H, m), 4.57 (1H, dt, J=12.3, 6.2 Hz), 4.65-4.84 (2H, m), 6.82-7.02 (3H, m), 7.19 (1H, td, J=8.3, 6.5 Hz).

G) 2-Chloro-6-cyclopropyl-2',4'-difluoro-3-isopropoxybiphenyl-4-carbaldehyde Manganese dioxide (5.37 g) was added at room temperature to a toluene (30 mL) solution of (2-chloro-6-cyclopropyl-2',4'-difluoro-3-isopropoxybiphenyl-4-yl)methanol (2.18 g), and the mixture was stirred at 60 C for 1 hour in a nitrogen atmosphere. The solid was filtered off, and then, the filtrate was concentrated under reduced pressure. The obtained residue was purified by silica gel column chromatography (hexane/ethyl acetate) to obtain the title compound (1.67 g)

$^1$H NMR (300 MHz, CDCl$_3$) delta 0.61-0.84 (4H, m), 1.39 (6H, dd, J=6.1, 3.1 Hz), 1.43-1.55 (1H, m), 4.39-4.65 (1H, m), 6.86-7.06 (2H, m), 7.20 (1H, td, J=8.3, 6.4 Hz), 7.40 (1H, s), 10.39 (1H, s).

H) Methyl 1-(1-((2-chloro-6-cyclopropyl-2',4'-difluoro-3-isopropoxybiphenyl-4-yl)methyl)piperidin-4-yl)-2-oxo-1,2-dihydropyridine-4-carboxylate A mixture of methyl 1-(1-(tert-butoxycarbonyl)piperidin-4-yl)-2-oxo-1,2-dihydropyridine-4-carboxylate (400 mg) and formic acid (6 mL) was stirred at 70 C for 1 hour in a nitrogen atmosphere, and then, the solvent was distilled off under reduced pressure. Sodium triacetoxyborohydride (504 mg) was added to a mixture of the obtained residue and 2-chloro-6-cyclopropyl-2',4'-difluoro-3-isopropoxybiphenyl-4-carbaldehyde (459 mg) in THF (10 mL) and DMA (2 mL), and the mixture was stirred at room temperature for 16 hours in a nitrogen atmosphere. A saturated aqueous solution of sodium bicarbonate was added to the reaction mixture, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (601 mg).

MS (ESI+): [M+H]$^+$ 571.9.

I) 1-(1-((2-Chloro-6-cyclopropyl-2',4'-difluoro-3-isopropoxybiphenyl-4-yl)methyl)piperidin-4-yl)-2-oxo-1,2-dihydropyridine-4-carboxylic acid A 2 M aqueous sodium hydroxide solution (2 mL) was added to an ethanol (8 mL) solution of methyl 1-(1-((2-chloro-6-cyclopropyl-2',4'-difluoro-3-isopropoxybiphenyl-4-yl)methyl)piperidin-4-yl)-2-oxo-1,2-dihydropyridine-4-carboxylate (590 mg), and the mixture was stirred at 80 C for 4 hours in a nitrogen atmosphere. The reaction mixture was concentrated to dryness under reduced pressure. The obtained residue was dissolved in water, and the solution was neutralized with 2 M hydrochloric acid. The resulting solid was collected by filtration and recrystallized (DMSO/ethanol) to obtain the title compound (157 mg).

$^1$H NMR (300 MHz, DMSO-d$_6$) delta 0.48-0.80 (4H, m), 1.27 (6H, d, J=6.1 Hz), 1.37-1.52 (1H, m), 1.69-1.98 (4H, m), 2.05-2.35 (2H, m), 2.89-3.04 (2H, m), 3.60 (2H, s), 4.37-4.51 (1H, m), 4.56-4.77 (1H, m), 6.57 (1H, dd, J=7.1, 1.9 Hz), 6.84 (1H, d, J=1.8 Hz), 7.07 (1H, s), 7.13-7.30 (1H, m), 7.32-7.48 (2H, m), 7.89 (1H, d, J=7.2 Hz).

Example 6

1-(1-((2-Cyclopropyl-2',4'-difluoro-5-isopropoxybiphenyl-4-yl)methyl)piperidin-4-yl)-3-ethyl-2-oxo-1,2-dihydropyridine-4-carboxylic acid

A) Methyl 2',4'-difluoro-3-isopropoxybiphenyl-4-carboxylate

A mixture of methyl 4-iodo-2-isopropoxybenzoate (4.10 g), (2,4-difluorophenyl)boronic acid (4.04 g), dicyclohexyl(2',6'-dimethoxybiphenyl-2-yl)phosphine (0.789 g), a 2 M aqueous sodium carbonate solution (19.2 mL), tris(dibenzylideneacetone)dipalladium(0) (0.821 g), and toluene (50 mL) was stirred at 100 C for 2 hours. The reaction mixture was poured to water at room temperature, and the mixture was passed through celite, followed by extraction with ethyl acetate. The obtained organic layer was washed with saturated saline and passed through a short silica gel (NH) column, and the solvent was distilled off under reduced pressure. The obtained residue was purified by silica gel column chromatography (hexane/ethyl acetate) to obtain the title compound (3.90 g)

$^1$H NMR (300 MHz, CDCl$_3$) delta 1.40 (6H, d, J=6.0 Hz), 3.90 (3H, s), 4.52-4.70 (1H, m), 6.83-7.01 (2H, m), 7.04-7.15 (2H, m), 7.33-7.49 (1H, m, J=6.4 Hz), 7.83 (1H, d, J=8.0 Hz).

B) Methyl 2-bromo-2',4'-difluoro-5-isopropoxybiphenyl-4-carboxylate

Dibromoisocyanuric acid (2.19 g) was added to a mixture of methyl 2',4'-difluoro-3-isopropoxybiphenyl-4-carboxylate (3.90 g) and DMF (40 mL), and the mixture was stirred at room temperature for 3 hours. Water was added to the reaction mixture, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (4.90 g)

$^1$H NMR (300 MHz, CDCl$_3$) delta 1.37 (6H, d, J=6.0 Hz), 3.90 (3H, s), 4.41-4.63 (1H, m), 6.85-7.02 (3H, m), 7.17-7.33 (1H, m), 8.04 (1H, s).

C) (2-Cyclopropyl-2',4'-difluoro-5-isopropoxybiphenyl-4-yl)methanol

A mixture of methyl 2-bromo-2',4'-difluoro-5-isopropoxybiphenyl-4-carboxylate (4.90 g), cyclopropylboronic acid (3.28 g), dicyclohexyl(2',6'-dimethoxybiphenyl-2-yl)phosphine (0.783 g), a 2 M aqueous sodium carbonate solution (19.1 mL), tris(dibenzylideneacetone)dipalladium(0) (0.815 g), and toluene (50 mL) was stirred overnight at 100 C. The organic layer was separated from the reaction mixture, washed with saturated saline, and passed through a short silica gel (NH) column, and the solvent was distilled off under reduced pressure. The obtained residue was purified by silica gel column chromatography (hexane/ethyl acetate). A THF (50 mL) solution of this purified product was added to a THF (50 mL) suspension of lithium aluminum hydride (0.474 g) under ice cooling. After stirring at the same temperature as above for 30 minutes, water (0.5 mL) and a 15% aqueous sodium hydroxide solution (0.5 mL) were added thereto, and the mixture was stirred for 5 minutes. Water (1.5 mL) was further added to the reaction mixture, and the mixture was stirred for 30 minutes and then filtered. The filtrate was concentrated under reduced pressure. The obtained residue was purified by silica gel column chromatography (hexane/ethyl acetate) to obtain the title compound (3.97 g).

$^1$H NMR (300 MHz, CDCl$_3$) delta 0.48-0.60 (2H, m), 0.66-0.79 (2H, m), 1.35 (6H, d, J=6.0 Hz), 1.59-1.72 (1H, m), 2.45 (1H, t, J=6.5 Hz), 4.47-4.63 (1H, m), 4.67 (2H, d, J=6.4 Hz), 6.71 (1H, s), 6.86-6.99 (3H, m), 7.19-7.36 (1H, m).

D) 2-Cyclopropyl-2',4'-difluoro-5-isopropoxybiphenyl-4-carbaldehyde

Manganese dioxide (10.8 g) was added to a toluene (30 mL) solution of (2-cyclopropyl-2',4'-difluoro-5-isopropoxybiphenyl-4-yl)methanol (3.97 g), and the mixture was stirred at 60 C for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (3.53 g).

$^1$H NMR (300 MHz, CDCl$_3$) delta 0.56-0.66 (2H, m), 0.70-0.80 (2H, m), 1.39 (6H, d, J=6.1 Hz), 1.58-1.70 (1H, m), 4.52-4.74 (1H, m), 6.82 (1H, s), 6.87-7.04 (2H, m), 7.28-7.35 (1H, m), 7.48 (1H, s), 10.47 (1H, s).

E) tert-Butyl 4-(4-(benzyloxy)-2-oxopyridin-1(2H)-yl)piperidine-1-carboxylate Potassium tert-butoxide (5.05 g) was added at room temperature to a DME (70 mL) solution of 4-(benzyloxy)pyridin-2(1H)-one (7.55 g). The reaction mixture was stirred at room temperature for 10 minutes. Then, potassium carbonate (10.4 g) and tert-butyl 4-(((4-methylphenyl)sulfonyl)oxy)piperidine-1-carboxylate (20.0 g) were added thereto, and the mixture was stirred at 100 C for 1 day in a nitrogen atmosphere. Then, DME (30 mL) was added thereto, and the mixture was further stirred during the weekend at 100 C. Saturated saline was added to the reaction mixture, followed by extraction with ethyl acetate twice. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (4.40 g).

MS (ESI+): [M+H]$^+$ 385.3.

F) tert-Butyl 4-(4-(benzyloxy)-3-iodo-2-oxopyridin-1(2H)-yl)piperidine-1-carboxylate N-Iodosuccinimide (2.85 g) was added at room temperature to an acetic acid (57.6 mL) solution of tert-butyl 4-(4-(benzyloxy)-2-oxopyridin-1(2H)-yl)piperidine-1-carboxylate (4.43 g), and the mixture was stirred at room temperature for 2 hours. The reaction mixture was rendered basic by the addition of a saturated aqueous solution of sodium bicarbonate, followed by extraction with ethyl acetate twice. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (4.83 g).

MS (ESI+): [M+H]$^+$ 511.1.

G) tert-Butyl 4-(4-(benzyloxy)-2-oxo-3-vinylpyridin-1(2H)-yl)piperidine-1-carboxylate A mixture of tert-butyl 4-(4-(benzyloxy)-3-iodo-2-oxopyridin-1(2H)-yl)piperidine-1-carboxylate (2.4 g), potassium vinyl trifluoroborate (0.945 g), triethylamine (1.3 mL), a dichloromethane adduct of 1,1'-bis(diphenylphosphino)ferrocene-palladium(II) dichloride (0.269 g), and ethanol (47 mL) was stirred overnight at 90 C in a nitrogen atmosphere. After cooling to room temperature, the solvent was distilled off under reduced pressure. Water and ethyl acetate were added to the obtained residue, and the organic layer was separated. The obtained organic layer was washed with saturated saline and dried over anhydrous magnesium sulfate, and the solvent was distilled off under reduced pressure. The obtained residue was purified by silica gel column chromatography (NH, hexane/ethyl acetate) to obtain the title compound (1.48 g).

MS (ESI+): [M+H]$^+$ 411.2.

H) tert-Butyl 4-(3-ethyl-4-hydroxy-2-oxopyridin-1(2H)-yl)piperidine-1-carboxylate 10% palladium carbon (containing 55% water, 0.767 g) was added to an ethanol (30 mL) solution of tert-butyl 4-(4-(benzyloxy)-2-oxo-3-vinylpyridin-1(2H)-yl)piperidine-1-carboxylate (1.48 g), and the mixture was stirred at room temperature for 3 hours in a hydrogen atmosphere. The reaction mixture was filtered through celite, and then, the solvent in the filtrate was distilled off under reduced pressure. The obtained residue was passed through a silica gel, and then, the solvent was distilled off under reduced pressure to obtain the title compound (1.12 g).

MS (ESI+): [M+H-tBu]$^+$ 267.1.

I) tert-Butyl 4-(3-ethyl-2-oxo-4-(((trifluoromethyl)sulfonyl)oxy)pyridin-1(2H)-yl)piperidine-1-carboxylate Trifluoromethanesulfonic anhydride (1.76 mL) was added at 0 C to a mixture of tert-butyl 4-(3-ethyl-4-hydroxy-2-oxopyridin-1(2H)-yl)piperidine-1-carboxylate (1.12 g) in pyridine (17.4 mL), and the mixture was stirred at 0 C for 30 minutes in a nitrogen atmosphere. Water was added thereto, and then, the solvent was distilled off under reduced pressure. Water was added again to the residue, followed by extraction with ethyl acetate. The obtained organic layer was washed with 1 M hydrochloric acid and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.14 g).

MS (ESI+): [M+H]$^+$ 399.1.

J) Methyl 1-(1-(tert-butoxycarbonyl)piperidin-4-yl)-3-ethyl-2-oxo-1,2-dihydropyridine-4-carboxylate A mixture of tert-butyl 4-(3-ethyl-2-oxo-4-(((trifluoromethyl)sulfonyl)oxy)pyridin-1(2H)-yl)piperidine-1-carboxylate (1.14 g), triethylamine (0.699 mL), methanol (3.05 mL), 1,1'-bis(diphenylphosphino)ferrocene-palladium(II) dichloride (0.184 g), and DMF (12.5 mL) was stirred at 90 C for 4 hours in a carbon monooxide atmosphere of 0.5 MPa. Water was added to the reaction mixture, followed by extraction with ethyl acetate twice. The obtained organic layer was washed with saturated saline twice and dried over anhydrous magnesium sulfate, and the solvent was distilled off under reduced pressure. The obtained residue was purified by silica gel column chromatography (NH, hexane/ethyl acetate) to obtain the title compound (0.798 g).

MS (ESI+): [M+H-tBu]$^+$ 309.1.

K) Methyl 1-(1-((2-cyclopropyl-2',4'-difluoro-5-isopropoxybiphenyl-4-yl)methyl)piperidin-4-yl)-3-ethyl-2-oxo-1,2-dihydropyridine-4-carboxylate A mixture of methyl 1-(1-(tert-butoxycarbonyl)piperidin-4-yl)-3-ethyl-2-oxo-1,2-dihydropyridine-4-carboxylate (150 mg) and formic acid (3 mL) was stirred at 70 C for 30 minutes, and then, the solvent was distilled off under reduced pressure. 2-Cyclopropyl-2',4'-difluoro-5-isopropoxybiphenyl-4-carbaldehyde (156 mg) and DMA (2 mL) were added to the obtained residue, and the mixture was stirred at room temperature for 10 minutes. Then, sodium triacetoxyborohydride (174 mg) was added thereto, and the mixture was stirred overnight at room temperature. A saturated aqueous solution of sodium bicarbonate was added to the reaction mixture, followed by extraction with ethyl acetate twice. The obtained organic layer was washed with saturated saline and dried over anhydrous magnesium sulfate, and the solvent was distilled off under reduced pressure. The obtained residue was purified by silica gel column chromatography (hexane/ethyl acetate) to obtain the title compound (208 mg).

MS (ESI+): [M+H]$^+$ 565.3.

L) 1-(1-((2-Cyclopropyl-2',4'-difluoro-5-isopropoxybiphenyl-4-yl)methyl)piperidin-4-yl)-3-ethyl-2-oxo-1,2-dihydropyridine-4-carboxylic acid A mixture of methyl 1-(1-((2-cyclopropyl-2',4'-difluoro-5-isopropoxybiphenyl-4-yl)methyl)piperidin-4-yl)-3-ethyl-2-oxo-1,2-dihydropyridine-4-carboxylate (208 mg), a 1 M aqueous sodium hydroxide solution (3 mL), and ethanol (6 mL) was stirred at 70 C for 1 hour. The reaction mixture was pH-adjusted to 3 using 1 M hydrochloric acid, followed by extraction with ethyl acetate twice. The obtained organic layer was dried over anhydrous sodium sulfate, and the solvent was distilled off under reduced pressure. The obtained residue was recrystallized (2-propanol/hexane) to obtain the title compound (156 mg).

$^1$H NMR (300 MHz, DMSO-$d_6$) delta 0.65 (2H, d, J=3.6 Hz), 0.70-0.79 (2H, m), 1.05 (3H, t, J=7.3 Hz), 1.30 (6H, d, J=5.9 Hz), 1.50-1.62 (1H, m), 1.92-2.07 (2H, m), 2.16-2.37 (2H, m), 2.67 (2H, q, J=7.2 Hz), 3.20-3.40 (2H, m), 3.45 (2H, brs), 4.21 (2H, brs), 4.63-4.77 (1H, m), 5.02 (1H, brs), 6.43 (1H, d, J=7.3 Hz), 6.92 (1H, s), 7.20 (1H, td, J=8.3, 2.4 Hz), 7.27 (1H, s), 7.32-7.52 (3H, m).

Example 7

1-(1-((6-Cyclopropyl-2,2',4'-trifluoro-3-isopropoxybiphenyl-4-yl)methyl)piperidin-4-yl)-3-ethyl-2-oxo-1,2-dihydropyridine-4-carboxylic acid

A) 2,2',3,4'-Tetrafluorobiphenyl-4-carbaldehyde (2,4-Difluorophenyl)boronic acid (5.39 g), a 2 M aqueous sodium carbonate solution (34.1 mL), tris(dibenzylideneacetone)dipalladium(0) (1.46 g), and dicyclohexyl(2',6'-dimethoxybiphenyl-2-yl)phosphine (1.40 g) were added at room temperature to a toluene (150 mL) solution of 4-bromo-2,3-difluorobenzaldehyde (5.03 g), and the mixture was stirred at 100 C for 16 hours in a nitrogen atmosphere. Water was added to the reaction mixture at room temperature, and the mixture was filtered through celite. Then, the filtrate was subjected to extraction with ethyl acetate. The organic layer was separated, washed with water and saturated saline in this order, and dried over anhydrous magnesium sulfate, and then, the solvent was distilled off under reduced pressure. The obtained residue was purified by silica gel column chromatography (hexane/ethyl acetate) to obtain the title compound (5.49 g).

$^1$H NMR (300 MHz, CDCl$_3$) delta 6.93-7.06 (2H, m), 7.23-7.30 (1H, m), 7.35-7.44 (1H, m), 7.70 (1H, ddd, J=8.1, 6.2, 1.8 Hz), 10.39 (1H, d, J=0.6 Hz).

B) 2,2',4'-Trifluoro-3-methoxybiphenyl-4-carbaldehyde

Sodium methoxide (28% methanol solution, 5.64 g) was added at room temperature to a methanol (120 mL) solution of 2,2',3,4'-tetrafluorobiphenyl-4-carbaldehyde (4.95 g), and the mixture was heated to reflux for 16 hours in a nitrogen atmosphere. Then, the solvent was distilled off under reduced pressure. The residue was diluted with ethyl acetate and water, followed by extraction with ethyl acetate. The organic layer was separated, washed with water and saturated saline in this order, and dried over anhydrous magnesium sulfate, and then, the solvent was distilled off under reduced pressure to obtain the title compound (5.14 g).

$^1$H NMR (300 MHz, CDCl$_3$) delta 4.13 (3H, d, J=2.6 Hz), 6.91-7.05 (2H, m), 7.09-7.16 (1H, m), 7.32-7.43 (1H, m), 7.67 (1H, dd, J=8.1, 1.4 Hz), 10.43 (1H, d, J=0.8 Hz).

C) 2,2',4'-Trifluoro-3-hydroxybiphenyl-4-carbaldehyde

48% hydrobromic acid (22.0 mL) was added at room temperature to an acetic acid (120 mL) solution of 2,2',4'-trifluoro-3-methoxybiphenyl-4-carbaldehyde (5.14 g), and the mixture was stirred at 120 C for 16 hours in a nitrogen atmosphere. Then, the solvent was distilled off under reduced pressure. The obtained residue was neutralized with a 1 M aqueous sodium hydroxide solution at room temperature, followed by extraction with ethyl acetate. The organic layer was separated, then washed with water and saturated saline in this order, and dried over anhydrous magnesium sulfate, and then, the solvent was distilled off under reduced pressure. The obtained residue was passed through a short silica gel column, and the solvent was distilled off under reduced pressure to obtain the title compound (4.60 g).

$^1$H NMR (300 MHz, CDCl$_3$) delta 6.91-7.05 (3H, m), 7.34-7.46 (2H, m), 9.96 (1H, d, J=1.8 Hz), 11.07 (1H, s).

D) 6-Bromo-2,2',4'-trifluoro-3-hydroxybiphenyl-4-carbaldehyde

Dibromoisocyanuric acid (2.25 g) was added at room temperature to a DMF (90 mL) solution of 2,2',4'-trifluoro-3-hydroxybiphenyl-4-carbaldehyde (3.29 g), and the mixture was stirred at the same temperature as above for 3 hours in a nitrogen atmosphere. A saturated aqueous solution of sodium thiosulfate was added to the reaction mixture at room temperature, followed by extraction with ethyl acetate. The organic layer was separated, then washed with water and saturated saline in this order, and dried over anhydrous magnesium sulfate, and then, the solvent was distilled off under reduced pressure. The obtained residue was purified by silica gel column chromatography (hexane/ethyl acetate) and silica gel column chromatography (diol, hexane/ethyl acetate) to obtain the title compound (3.15 g).

$^1$H NMR (300 MHz, CDCl$_3$) delta 6.93-7.06 (2H, m), 7.22-7.32 (1H, m), 7.71 (1H, d, J=1.9 Hz), 9.92 (1H, d, J=1.9 Hz), 10.90 (1H, brs).

E) 6-Bromo-3-isopropoxy-2,2',4'-trifluorobiphenyl-4-carbaldehyde

2-Iodopropane (461 mg) was added at room temperature to a mixture of 6-bromo-2,2',4'-trifluoro-3-hydroxybiphenyl-4-carbaldehyde (598 mg), potassium carbonate (499 mg), and DMF (10 mL), and the mixture was stirred at 60 C for 3 hours in a nitrogen atmosphere. Water was added to the reaction mixture, followed by extraction with ethyl acetate. The organic layer was separated, then washed with water and saturated saline in this order, and dried over anhydrous magnesium sulfate, and then, the solvent was distilled off under reduced pressure. The obtained residue was purified by silica gel column chromatography (hexane/ethyl acetate) to obtain the title compound (637 mg).

$^1$H NMR (300 MHz, CDCl$_3$) delta 1.39 (6H, dd, J=6.0, 3.1 Hz), 4.57-4.71 (1H, m), 6.91-7.07 (2H, m), 7.23-7.33 (1H, m), 7.94 (1H, d, J=1.8 Hz), 10.38 (1H, s).

F) 6-Cyclopropyl-3-isopropoxy-2,2',4'-trifluorobiphenyl-4-carbaldehyde

Cyclopropylboronic acid (424 mg), a 2 M aqueous sodium carbonate solution (3.29 mL), tris(dibenzylideneacetone)dipalladium(0) (151 mg), and dicyclohexyl(2',6'-dimethoxybiphenyl-2-yl)phosphine (135 mg) were added at room temperature to a toluene (15 mL) solution of 6-bromo-3-isopropoxy-2,2',4'-trifluorobiphenyl-4-carbaldehyde (615 mg), and the mixture was stirred at 100 C for 16 hours in an argon atmosphere. Water was added to the reaction mixture, and then, the mixture was filtered through celite. The filtrate was subjected to extraction with ethyl acetate. The organic layer was separated, then washed with water and saturated saline in this order, and dried over anhydrous magnesium sulfate, and then, the solvent was distilled off under reduced pressure. The obtained residue was purified by silica gel column chromatography (hexane/ethyl acetate) to obtain the title compound (529 mg).

$^1$H NMR (300 MHz, DMSO-d$_6$) delta 0.59-0.72 (2H, m), 0.74-0.87 (2H, m), 1.31 (6H, dd, J=6.0, 2.6 Hz), 1.50-1.62 (1H, m), 4.42-4.54 (1H, m), 7.19 (1H, d, J=1.1 Hz), 7.27 (1H, tdd, J=8.5, 2.5, 0.9 Hz), 7.41-7.50 (1H, m), 7.56 (1H, td, J=8.5, 6.5 Hz), 10.29 (1H, s).

G) Methyl 1-(1-((6-cyclopropyl-2,2',4'-trifluoro-3-isopropoxybiphenyl-4-yl)methyl)piperidin-4-yl)-3-ethyl-2-oxo-1,2-dihydropyridine-4-carboxylate Formic acid (3 mL) was added to methyl 1-(1-(tert-butoxycarbonyl)piperidin-4-yl)-3-ethyl-2-oxo-1,2-dihydropyridine-4-carboxylate (225 mg), and the mixture was stirred at 70 C for 30 minutes. Then, the solvent was distilled off. 6-Cyclopropyl-2,2',4'-trifluoro-3-isopropoxybiphenyl-4-carbaldehyde (206 mg), THF (3 mL), and DMA (1 mL) were added to the obtained residue, and the mixture was stirred at room temperature for 10 minutes. Then, sodium triacetoxyborohydride (261 mg) was added thereto, and the mixture was stirred overnight at room temperature. A saturated aqueous solution of sodium bicarbonate was added to the obtained reaction mixture, followed by extraction with ethyl acetate twice. The obtained organic layer was washed with saturated saline and then dried over anhydrous magnesium sulfate, and the solvent was distilled off under reduced pressure. The obtained residue was purified by silica gel column chromatography (hexane/ethyl acetate) to obtain the title compound (161 mg).

MS (ESI+): [M+H]$^+$ 583.3.

H) 1-(1-((6-Cyclopropyl-2,2',4'-trifluoro-3-isopropoxybiphenyl-4-yl)methyl)piperidin-4-yl)-3-ethyl-2-oxo-1,2-dihydropyridine-4-carboxylic acid A mixture of methyl 1-(1-((6-cyclopropyl-2,2',4'-trifluoro-3-isopropoxybiphenyl-4-yl)methyl)piperidin-4-yl)-3-ethyl-2-oxo-1,2-dihydropyridine-4-carboxylate (161 mg), a 1 M aqueous sodium hydroxide solution (1 mL), and ethanol (2 mL) was stirred at 70 C for 1 hour. The reaction mixture was pH-adjusted to 3 using 1 M hydrochloric acid, followed by extraction with ethyl acetate twice. The organic layer was separated and dried over anhydrous sodium sulfate, and the solvent was distilled off under reduced pressure. The obtained residue was crystallized (2-propanol/hexane) to obtain the title compound (123 mg).

$^1$H NMR (300 MHz, DMSO-$d_6$) delta 0.64-0.85 (4H, m), 1.01-1.10 (3H, m), 1.29 (6H, d, J=6.0 Hz), 1.46-1.60 (1H, m), 1.84-2.01 (2H, m), 2.04-2.34 (2H, m), 2.67 (2H, q, J=7.1 Hz), 2.70-3.45 (4H, m), 3.90-4.29 (2H, m), 4.33-4.55 (1H, m), 4.95 (1H, brs), 6.41 (1H, d, J=7.2 Hz), 7.02-7.30 (2H, m), 7.42 (1H, td, J=9.7, 2.5 Hz), 7.47-7.57 (2H, m), 12.76-13.80 (1H, m).

Example 43

1-(1-((6-Cyclopropyl-2,4'-difluoro-3-isopropoxybiphenyl-4-yl)methyl)piperidin-4-yl)-3-ethyl-2-oxo-1,2-dihydropyridine-4-carboxylic acid

A) 1-Bromo-2-fluoro-3-(methoxymethoxy)benzene

Chloro(methoxy)methane (11.8 mL) was added at 0 C to a THF (150 mL) solution of 3-bromo-2-fluorophenol (15.0 g) and N,N-diisopropylethylamine (41.1 mL). The reaction mixture was stirred overnight at room temperature in a nitrogen atmosphere and then filtered through celite. The obtained filtrate was washed with 1 M hydrochloric acid and a saturated aqueous solution of sodium bicarbonate in this order, and then, the solvent was distilled off under reduced pressure. The obtained residue was passed through a short silica gel column (NH, hexane/ethyl acetate), and the solvent was distilled off under reduced pressure to obtain the title compound (17.9 g)

$^1$H NMR (300 MHz, DMSO-$d_6$) delta 3.41 (3H, s), 5.27 (2H, s), 7.06-7.14 (1H, m), 7.24-7.34 (2H, m).

B) 2,4'-Difluoro-3-(methoxymethoxy)biphenyl

A mixture of 1-bromo-2-fluoro-3-(methoxymethoxy)benzene (17.9 g), (4-fluorophenyl)boronic acid (16.0 g), tris(dibenzylideneacetone)dipalladium(0) (3.49 g), a 2 M aqueous sodium carbonate solution (114 mL), dicyclohexyl(2',6'-dimethoxybiphenyl-2-yl)phosphine (3.13 g), and toluene (180 mL) was stirred at 100 C for 2 hours in a nitrogen atmosphere. The reaction mixture was cooled to room temperature and then passed through celite. The organic layer was separated, and the solvent was distilled off under reduced pressure. The obtained residue was passed through a short silica gel (NH) column, and the solvent was distilled off under reduced pressure to obtain the title compound (19.0 g).

$^1$H NMR (300 MHz, DMSO-$d_6$) delta 3.44 (3H, s), 5.28 (2H, s), 7.08-7.36 (5H, m), 7.54-7.63 (2H, m).

C) 2,4'-Difluoro-3-(methoxymethoxy)biphenyl-4-carbaldehyde n-Butyllithium (1.6 M hexane solution, 52.2 mL) was added at −78 C to an anhydrous THF (200 mL) solution of 2,4'-difluoro-3-(methoxymethoxy)biphenyl (19.0 g) in an argon atmosphere, and then, the mixture was stirred at −78 C for 1 hour. DMF (12.9 mL) was added thereto, and then, the mixture was stirred for 3 hours in an argon atmosphere while heated from −78 C to 0 C. A saturated aqueous solution of ammonium chloride was added to the reaction mixture at room temperature, followed by extraction with ethyl acetate. The organic layer was separated, then washed with saturated saline, and dried over anhydrous magnesium sulfate, and then, the solvent was distilled off under reduced pressure. The obtained residue was solidified with hexane to obtain the title compound (16.4 g).

$^1$H NMR (300 MHz, DMSO-$d_6$) delta 3.54 (3H, s), 5.31 (2H, d, J=0.8 Hz), 7.32-7.49 (3H, m), 7.62-7.73 (3H, m), 10.31 (1H, d, J=0.8 Hz).

D) 2,4'-Difluoro-3-hydroxybiphenyl-4-carbaldehyde

6 M hydrochloric acid (49.1 mL) was added to an ethanol (160 mL) solution of 2,4'-difluoro-3-(methoxymethoxy)biphenyl-4-carbaldehyde (16.4 g). The reaction mixture was stirred at 50 C for 30 minutes and further at room temperature for 2 hours. The resulting solid was collected by filtration and then washed with ethanol-water and water in this order to obtain the title compound (12.7 g).

$^1$H NMR (300 MHz, DMSO-$d_6$) delta 7.10 (1H, dd, J=7.8, 6.8 Hz), 7.31-7.40 (2H, m), 7.56 (1H, dd, J=8.2, 1.4 Hz), 7.62-7.70 (2H, m), 10.29 (1H, s), 11.02 (1H, s).

E) 6-Bromo-2,4'-difluoro-3-hydroxybiphenyl-4-carbaldehyde

Dibromoisocyanuric acid (8.87 g) was added at room temperature to a DMF (75 mL) solution of 2,4'-difluoro-3-hydroxybiphenyl-4-carbaldehyde (12.7 g), and the mixture was stirred at room temperature for 30 minutes. Water (50 mL) was added dropwise to the reaction mixture, and the mixture was stirred at room temperature for 1 hour. The resulting solid was collected by filtration, then washed with DMF-water, and dried to obtain the title compound (17.6 g).

$^1$H NMR (300 MHz, DMSO-$d_6$) delta 7.27-7.50 (4H, m), 7.77 (1H, d, J=1.8 Hz), 10.27 (1H, s), 11.15 (1H, s).

F) 6-Bromo-2,4'-difluoro-3-isopropoxybiphenyl-4-carbaldehyde

A mixture of 6-bromo-2,4'-difluoro-3-hydroxybiphenyl-4-carbaldehyde (3.50 g), 2-iodopropane (5.70 g), potassium carbonate (3.09 g), and DMF (15 mL) was stirred at 50 C for 1 hour. The reaction mixture was poured to water, followed by extraction with ethyl acetate twice. The organic layer was separated, then washed with saturated saline, and dried over anhydrous magnesium sulfate, and the solvent was distilled off under reduced pressure. The obtained residue was purified by silica gel column chromatography (hexane/ethyl acetate) to obtain the title compound (2.94 g)

$^1$H NMR (300 MHz, DMSO-$d_6$) delta 1.34 (6H, dd, J=6.1, 0.7 Hz), 4.50-4.64 (1H, m), 7.32-7.42 (2H, m), 7.43-7.51 (2H, m), 7.83 (1H, d, J=1.8 Hz), 10.26 (1H, s).

G) 6-Cyclopropyl-2,4'-difluoro-3-isopropoxybiphenyl-4-carbaldehyde

A mixture of 6-bromo-2,4'-difluoro-3-isopropoxybiphenyl-4-carbaldehyde (2.94 g), cyclopropylboronic acid (1.42 g), tris(dibenzylideneacetone)dipalladium(0) (0.531 g), a 2 M aqueous sodium carbonate solution (12.4 mL), dicyclohexyl(2',6'-dimethoxybiphenyl-2-yl)phosphine (0.510 g), and toluene (30 mL) was stirred overnight at 100 C in a nitrogen atmosphere. The reaction mixture was diluted with ethyl acetate and water and then filtered through celite. The organic layer was separated from the filtrate, and then, the solvent was distilled off under reduced pressure. The obtained residue was purified by silica gel column chromatography (hexane/ethyl acetate) to obtain the title compound (2.38 g).

$^1$H NMR (300 MHz, DMSO-$d_6$) delta 0.62-0.70 (2H, m), 0.75-0.84 (2H, m), 1.31 (6H, dd, J=6.1, 0.7 Hz), 1.52-1.65 (1H, m), 4.43-4.53 (1H, m), 7.15 (1H, d, J=1.2 Hz), 7.31-7.40 (2H, m), 7.43-7.51 (2H, m), 10.28 (1H, s).

H) Methyl 1-(1-((6-cyclopropyl-2,4'-difluoro-3-isopropoxybiphenyl-4-yl)methyl)piperidin-4-yl)-3-ethyl-2-oxo-1,2-dihydropyridine-4-carboxylate Formic acid (2 mL) was added to methyl 1-(1-(tert-butoxycarbonyl)piperidin-4-yl)-3-ethyl-2-oxo-1,2-dihydropyridine-4-carboxylate (300 mg), and the mixture was stirred at 70 C for 1 hour. Then, the solvent was distilled off under reduced pressure. Sodium triacetoxyborohydride (262 mg) was added to a mixture of the obtained residue, 6-cyclopropyl-2,4'-difluoro-3-isopropoxybiphenyl-4-carbaldehyde (260 mg), and THF (5.0 mL), and the mixture was stirred overnight at room temperature. A saturated aqueous solution of sodium bicarbonate was added to the reaction mixture at room temperature, followed by extraction with ethyl acetate. The organic layer was separated, and then, the solvent was distilled off under reduced pressure. The obtained residue was purified by silica gel column chromatography (hexane/ethyl acetate) to obtain the title compound (350 mg).

MS (ESI+): [M+H]$^+$ 565.4.

I) 1-(1-((6-Cyclopropyl-2,4'-difluoro-3-isopropoxybiphenyl-4-yl)methyl)piperidin-4-yl)-3-ethyl-2-oxo-1,2-dihydropyridine-4-carboxylic acid A 2 M aqueous sodium hydroxide solution (1.54 mL) was added at room temperature to a methanol (3 mL) solution of methyl 1-(1-((6-cyclopropyl-2,4'-difluoro-3-isopropoxybiphenyl-4-yl)methyl)piperidin-4-yl)-3-ethyl-2-oxo-1,2-dihydropyridine-4-carboxylate (348 mg), and the mixture was stirred at 50 C for 1 hour. The reaction mixture was cooled to room temperature and neutralized with 2 M hydrochloric acid, and the solvent was distilled off under reduced pressure. The obtained residue was crystallized from water, and the obtained solid was recrystallized (ethanol/diisopropyl ether) to obtain the title compound (240 mg).

$^1$H NMR (300 MHz, DMSO-$d_6$) delta 0.56-0.64 (2H, m), 0.72-0.81 (2H, m), 0.98-1.08 (3H, m), 1.26 (6H, d, J=6.0 Hz), 1.51-1.64 (1H, m), 1.68-1.92 (4H, m), 2.17 (2H, t, J=10.5 Hz), 2.65 (2H, q, J=7.3 Hz), 2.98 (2H, d, J=11.1 Hz), 3.56 (2H, s), 4.29-4.41 (1H, m), 4.63-4.78 (1H, m), 6.33 (1H, d, J=7.3 Hz), 6.84 (1H, s), 7.24-7.36 (2H, m), 7.37-7.46 (2H, m), 7.67 (1H, d, J=7.4 Hz).

Example 44

1-(1-((6-Cyclopropyl-3-ethoxy-2,4'-difluorobiphenyl-4-yl)methyl)piperidin-4-yl)-3-ethyl-2-oxo-1,2-dihydropyridine-4-carboxylic acid A) 6-Cyclopropyl-3-ethoxy-2,4'-difluorobiphenyl-4-carbaldehyde A mixture of 6-bromo-2,4'-difluoro-3-hydroxybiphenyl-4-carbaldehyde (2.60 g), cyclopropylboronic acid (1.43 g), tris(dibenzylideneacetone)dipalladium(0) (0.760 g), a 2 M aqueous sodium carbonate solution (12.5 mL), dicyclohexyl (2',6'-dimethoxybiphenyl-2-yl)phosphine (0.682 g), and toluene (70 mL) was stirred overnight at 100 C in a nitrogen atmosphere. The reaction mixture was diluted with ethyl acetate and water and then filtered through celite. The organic layer was separated from the filtrate, and then, the solvent was distilled off under reduced pressure. The obtained residue was purified by silica gel column chromatography (hexane/ethyl acetate) to obtain the title compound (1.60 g).

MS (ESI−): [M−H]$^−$ 273.0.

B) 6-Cyclopropyl-3-ethoxy-2,4'-difluorobiphenyl-4-carbaldehyde

A mixture of 6-cyclopropyl-3-ethoxy-2,4'-difluorobiphenyl-4-carbaldehyde (530 mg), iodoethane (603 mg), potassium carbonate (534 mg), and acetone (10 mL) was stirred at 50 C for 2 hours and then filtered through celite. The filtrate was concentrated under reduced pressure, and then, the obtained residue was purified by silica gel column chromatography (hexane/ethyl acetate) to obtain the title compound (400 mg).

MS (ESI+): [M+H]$^+$ 303.1.

C) Methyl 1-(1-((6-cyclopropyl-3-ethoxy-2,4'-difluorobiphenyl-4-yl)methyl)piperidin-4-yl)-3-ethyl-2-oxo-1,2-dihydropyridine-4-carboxylate Formic acid (2 mL) was added to methyl 1-(1-(tert-butoxycarbonyl)piperidin-4-yl)-3-ethyl-2-oxo-1,2-dihydropyridine-4-carboxylate (300 mg), and the mixture was stirred at 70 C for 1 hour. Then, the solvent was distilled off under reduced pressure. Sodium triacetoxyborohydride (262 mg) was added to a mixture of the obtained residue, 6-cyclopropyl-3-ethoxy-2,4'-difluorobiphenyl-4-carbaldehyde (249 mg), and THF (5.0 mL), and the mixture was stirred overnight at room temperature. A saturated aqueous solution of sodium bicarbonate was added to the reaction mixture at room temperature, followed by extraction with ethyl acetate. The organic layer was separated, and then, the solvent was distilled off under reduced pressure. The obtained residue was purified by silica gel column chromatography (hexane/ethyl acetate) to obtain the title compound (387 mg).

MS (ESI+): [M+H]$^+$ 551.7.

D) 1-(1-((6-Cyclopropyl-3-ethoxy-2,4'-difluorobiphenyl-4-yl)methyl)piperidin-4-yl)-3-ethyl-2-oxo-1,2-dihydropyridine-4-carboxylic acid A 2 M aqueous sodium hydroxide solution (1.73 mL) was added to a methanol (3 mL) solution of methyl 1-(1-((6-cyclopropyl-3-ethoxy-2,4'-difluorobiphenyl-4-yl)methyl)piperidin-4-yl)-3-ethyl-2-oxo-1,2-dihydropyridine-4-carboxylate (382 mg), and the mixture was stirred at 50 C for 1 hour. The reaction mixture was cooled to room temperature and neutralized with 2 M hydrochloric acid, and the solvent was distilled off under reduced pressure. The obtained residue was crystallized from water, and the obtained solid was recrystallized (ethanol/diisopropyl ether/hexane) to obtain the title compound (211 mg).

$^1$H NMR (300 MHz, DMSO-$d_6$) delta 0.56-0.65 (2H, m), 0.72-0.80 (2H, m), 0.99-1.08 (3H, m), 1.32 (3H, t, J=7.0 Hz), 1.52-1.64 (1H, m), 1.69-1.90 (4H, m), 2.19 (2H, t, J=10.5 Hz), 2.65 (2H, q, J=7.2 Hz), 2.99 (2H, d, J=11.3 Hz), 3.55

(2H, s), 4.04 (2H, q, J=7.0 Hz), 4.64-4.78 (1H, m), 6.33 (1H, d, J=7.3 Hz), 6.81 (1H, s), 7.26-7.35 (2H, m), 7.38-7.46 (2H, m), 7.66 (1H, d, J=7.3 Hz).

Example 45

1-(1-((6-Cyclopropyl-3-ethoxy-2,2',4'-trifluorobiphenyl-4-yl)methyl)piperidin-4-yl)-3-ethyl-2-oxo-1,2-dihydropyridine-4-carboxylic acid A) 6-Bromo-3-ethoxy-2,2',4'-trifluorobiphenyl-4-carbaldehyde Iodoethane (0.77 g) was added at room temperature to a mixture of 6-bromo-2,2',4'-trifluoro-3-hydroxybiphenyl-4-carbaldehyde (1.09 g), potassium carbonate (0.91 g), and DMF (20 mL), and the mixture was stirred at 60 C for 2 hours in a nitrogen atmosphere. Water was added to the reaction mixture at room temperature, followed by extraction with ethyl acetate. The organic layer was separated, washed with water and saturated saline in this order, and dried over anhydrous magnesium sulfate, and then, the solvent was distilled off under reduced pressure. The obtained residue was purified by silica gel column chromatography (hexane/ethyl acetate) to obtain the title compound (1.07 g).
$^1$H NMR (300 MHz, CDCl$_3$) delta 1.45 (3H, td, J=7.0, 0.8 Hz), 4.29-4.39 (2H, m), 6.92-7.06 (2H, m), 7.23-7.32 (1H, m), 7.93 (1H, d, J=1.8 Hz), 10.39 (1H, s).

B) 6-Cyclopropyl-3-ethoxy-2,2',4'-trifluorobiphenyl-4-carbaldehyde

Cyclopropylboronic acid (0.77 g), a 2 M aqueous sodium carbonate solution (5.94 mL), tris(dibenzylideneacetone)dipalladium(0) (0.272 g), and dicyclohexyl(2',6'-dimethoxybiphenyl-2-yl)phosphine (0.244 g) were added at room temperature to a toluene (20 mL) solution of 6-bromo-3-ethoxy-2,2',4'-trifluorobiphenyl-4-carbaldehyde (1.07 g), and the mixture was stirred at 100 C for 15 hours in an argon atmosphere. Water was added to the reaction mixture at room temperature, and then, the mixture was filtered through celite. The filtrate was subjected to extraction with ethyl acetate. The organic layer was separated, then washed with water and saturated saline in this order, and dried over anhydrous magnesium sulfate, and then, the solvent was distilled off under reduced pressure. The obtained residue was purified by silica gel column chromatography (hexane/ethyl acetate) to obtain the title compound (904 mg).
$^1$H NMR (300 MHz, CDCl$_3$) delta 0.59-0.67 (1H, m), 0.67-0.76 (1H, m), 0.77-0.83 (2H, m), 1.43 (3H, td, J=7.1, 0.7 Hz), 1.50-1.63 (1H, m), 4.28 (2H, qt, J=7.0, 1.3 Hz), 6.92-7.05 (2H, m), 7.24-7.36 (2H, m), 10.41 (1H, s).

C) Methyl 1-(1-((6-cyclopropyl-3-ethoxy-2,2',4'-trifluorobiphenyl-4-yl)methyl)piperidin-4-yl)-3-ethyl-2-oxo-1,2-dihydropyridine-4-carboxylate A mixture of methyl 1-(1-(tert-butoxycarbonyl)piperidin-4-yl)-3-ethyl-2-oxo-1,2-dihydropyridine-4-carboxylate (300 mg) and formic acid (6 mL) was stirred at 70 C for 30 minutes in a nitrogen atmosphere, and then, the solvent was distilled off under reduced pressure. Sodium triacetoxyborohydride (349 mg) was added to a mixture of the obtained residue, 6-cyclopropyl-3-ethoxy-2,2',4'-trifluorobiphenyl-4-carbaldehyde (296 mg), and THF (8 mL), and the mixture was stirred at room temperature for 16 hours in a nitrogen atmosphere. A saturated aqueous solution of sodium bicarbonate was added to the reaction mixture at room temperature, followed by extraction with ethyl acetate. The organic layer was separated, then washed with water and saturated saline in this order, and dried over anhydrous magnesium sulfate, and the solvent was distilled off under reduced pressure. The obtained residue was purified by silica gel column chromatography (hexane/ethyl acetate) to obtain the title compound (282 mg).
MS (ESI+): [M+H]$^+$ 569.3.

D) 1-(1-((6-Cyclopropyl-3-ethoxy-2,2',4'-trifluorobiphenyl-4-yl)methyl)piperidin-4-yl)-3-ethyl-2-oxo-1,2-dihydropyridine-4-carboxylic acid A 2 M aqueous sodium hydroxide solution (1.5 mL) was added to an ethanol (6 mL) solution of methyl 1-(1-((6-cyclopropyl-3-ethoxy-2,2',4'-trifluorobiphenyl-4-yl)methyl)piperidin-4-yl)-3-ethyl-2-oxo-1,2-dihydropyridine-4-carboxylate (264 mg), and the mixture was stirred at 80 C for 3 hours in a nitrogen atmosphere. Then, the solvent was distilled off under reduced pressure. Water was added to the residue, and the mixture was neutralized with 2 M hydrochloric acid, followed by extraction with a mixed solution of ethyl acetate and THF. The organic layer was separated, then washed with water and saturated saline in this order, and dried over anhydrous magnesium sulfate, and the solvent was distilled off under reduced pressure. The obtained residue was crystallized (hexane/ethyl acetate) and further recrystallized (hexane/ethanol) to obtain the title compound (173 mg).
$^1$H NMR (300 MHz, DMSO-d$_6$) delta 0.55-0.63 (2H, m), 0.72-0.80 (2H, m), 1.04 (3H, t, J=7.3 Hz), 1.32 (3H, t, J=7.0 Hz), 1.47-1.59 (1H, m), 1.68-1.93 (4H, m), 2.14-2.28 (2H, m), 2.66 (2H, q, J=7.2 Hz), 2.99 (2H, d, J=11.5 Hz), 3.52-3.62 (2H, m), 4.04 (2H, q, J=7.0 Hz), 4.64-4.79 (1H, m), 6.33 (1H, d, J=7.3 Hz), 6.86 (1H, s), 7.17-7.26 (1H, m), 7.40 (1H, td, J=9.7, 2.5 Hz), 7.50 (1H, td, J=8.5, 6.7 Hz), 7.66 (1H, d, J=7.4 Hz).

Example 47

1-(1-(4,5-Dicyclopropyl-3-fluoro-2-isopropoxybenzyl)piperidin-4-yl)-3-ethyl-2-oxo-1,2-dihydropyridine-4-carboxylic acid A) 4-Cyclopropyl-2,3-difluorobenzaldehyde Cyclopropylboronic acid (1.77 g), a 2 M aqueous sodium carbonate solution (21 mL), tris(dibenzylideneacetone)dipalladium(0) (0.882 g), and dicyclohexyl(2',6'-dimethoxybiphenyl-2-yl)phosphine (0.847 g) were added at room temperature to a toluene (70 mL) solution of 4-bromo-2,3-difluorobenzaldehyde (3.04 g), and the mixture was stirred at 100 C for 15 hours in an argon atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (2.18 g).
$^1$H NMR (300 MHz, CDCl$_3$) delta 0.82-0.90 (2H, m), 1.11-1.20 (2H, m), 2.14-2.25 (1H, m), 6.70 (1H, ddd, J=8.2, 6.3, 1.7 Hz), 7.51 (1H, ddd, J=8.3, 6.3, 1.8 Hz), 10.27 (1H, d, J=0.6 Hz).

B) 4-Cyclopropyl-3-fluoro-2-methoxybenzaldehyde

Sodium methoxide (28% methanol solution, 3.43 g) was added at room temperature to a methanol (100 mL) solution of 4-cyclopropyl-2,3-difluorobenzaldehyde (2.16 g), and the mixture was stirred at 70 C for 15 hours in a nitrogen atmosphere. Water was added to the reaction mixture, and methanol was distilled off under reduced pressure. The residue was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (2.11 g).

$^1$H NMR (400 MHz, CDCl$_3$) delta 0.79-0.84 (2H, m), 1.07-1.14 (2H, m), 2.13-2.22 (1H, m), 4.08 (3H, d, J=2.4 Hz), 6.59 (1H, dd, J=8.2, 6.4 Hz), 7.50 (1H, dd, J=8.3, 1.4 Hz), 10.31 (1H, d, J=0.6 Hz).

C) 4-Cyclopropyl-3-fluoro-2-hydroxybenzaldehyde

Boron tribromide (1 M dichloromethane solution, 18.5 mL) was added at −78 C to a dichloromethane (70 mL) solution of 4-cyclopropyl-3-fluoro-2-methoxybenzaldehyde (1.79 g), and the mixture was stirred at the same temperature as above for 2 hours in a nitrogen atmosphere and then stirred at 0 C for 1 hour. A saturated aqueous solution of sodium bicarbonate was added to the reaction mixture at 0 C, and dichloromethane was distilled off under reduced pressure. The obtained residue was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.50 g).

$^1$H NMR (300 MHz, CDCl$_3$) delta 0.81-0.89 (2H, m), 1.09-1.18 (2H, m), 2.17-2.28 (1H, m), 6.44 (1H, dd, J=8.2, 5.9 Hz), 7.23 (1H, dd, J=8.2, 1.3 Hz), 9.82 (1H, d, J=1.9 Hz), 11.02 (1H, s).

D) 5-Bromo-4-cyclopropyl-3-fluoro-2-hydroxybenzaldehyde

Dibromoisocyanuric acid (1.43 g) was added at room temperature to a DMF (50 mL) solution of 4-cyclopropyl-3-fluoro-2-hydroxybenzaldehyde (1.50 g), and the mixture was stirred at the same temperature as above for 3 hours in a nitrogen atmosphere. A saturated aqueous solution of sodium thiosulfate was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.73 g)

$^1$H NMR (400 MHz, CDCl$_3$) delta 1.04-1.18 (4H, m), 1.89-1.98 (1H, m), 7.55 (1H, d, J=1.9 Hz), 9.80 (1H, d, J=1.9 Hz), 10.81 (1H, s).

E) 4,5-Dicyclopropyl-3-fluoro-2-hydroxybenzaldehyde

Cyclopropylboronic acid (1.72 g), a 2 M aqueous sodium carbonate solution (13 mL), tris(dibenzylideneacetone)dipalladium(0) (0.611 g), and dicyclohexyl(2',6'-dimethoxybiphenyl-2-yl)phosphine (0.548 g) were added at room temperature to a toluene (50 mL) solution of 5-bromo-4-cyclopropyl-3-fluoro-2-hydroxybenzaldehyde (1.73 g), and the mixture was stirred at 100 C for 15 hours in an argon atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.31 g)

$^1$H NMR (300 MHz, CDCl$_3$) delta 0.62-0.69 (2H, m), 0.94-1.02 (2H, m), 1.04-1.12 (4H, m), 1.97-2.17 (2H, m), 6.97 (1H, dd, J=1.4, 0.8 Hz), 9.79 (1H, d, J=1.9 Hz), 10.78 (1H, s).

F) 4,5-Dicyclopropyl-3-fluoro-2-isopropoxybenzaldehyde

2-Iodopropane (862 mg) was added at room temperature to a mixture of 4,5-dicyclopropyl-3-fluoro-2-hydroxybenzaldehyde (744 mg), potassium carbonate (934 mg), and DMF (20 mL), and the mixture was stirred at 60 C for 2 hours in a nitrogen atmosphere. Water was added to the reaction mixture, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (865 mg).

$^1$H NMR (300 MHz, CDCl$_3$) delta 0.67-0.75 (2H, m), 0.90-1.02 (4H, m), 1.03-1.12 (2H, m), 1.34 (6H, dd, J=6.1, 0.8 Hz), 1.88-2.00 (1H, m), 2.11-2.23 (1H, m), 4.41-4.56 (1H, m), 7.19 (1H, d, J=1.0 Hz), 10.30 (1H, s).

G) Methyl 1-(1-(4,5-dicyclopropyl-3-fluoro-2-isopropoxybenzyl)piperidin-4-yl)-3-ethyl-2-oxo-1,2-dihydropyridine-4-carboxylate A mixture of methyl 1-(1-(tert-butoxycarbonyl)piperidin-4-yl)-3-ethyl-2-oxo-1,2-dihydropyridine-4-carboxylate (360 mg) in formic acid (8 mL) was stirred at 70 C for 30 minutes in a nitrogen atmosphere, and then, the solvent was distilled off under reduced pressure. Sodium triacetoxyborohydride (418 mg) was added at room temperature to a mixture of the obtained residue and 4,5-dicyclopropyl-3-fluoro-2-isopropoxybenzaldehyde (287 mg) in THF (10 mL), and the mixture was stirred at the same temperature as above for 15 hours in a nitrogen atmosphere. A saturated aqueous solution of sodium bicarbonate was added to the reaction mixture, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (381 mg).

MS (ESI+): [M+H]$^+$ 511.3.

H) 1-(1-(4,5-Dicyclopropyl-3-fluoro-2-isopropoxybenzyl)piperidin-4-yl)-3-ethyl-2-oxo-1,2-dihydropyridine-4-carboxylic acid A 2 M aqueous sodium hydroxide solution (2 mL) was added to an ethanol (8 mL) solution of methyl 1-(1-(4,5-dicyclopropyl-3-fluoro-2-isopropoxybenzyl)piperidin-4-yl)-3-ethyl-2-oxo-1,2-dihydropyridine-4-carboxylate (358 mg), and the mixture was stirred at 80 C for 3 hours in a nitrogen atmosphere. The solvent in the reaction mixture was distilled off under reduced pressure. The obtained residue was dissolved in water, and the solution was neutralized with 2 M hydrochloric acid, followed by extraction with a mixed solution of ethyl acetate and THF. The obtained organic layer was washed with water and saturated saline in this order and dried over anhydrous magnesium sulfate, and then, the solvent was distilled off under reduced pressure. The obtained residue was crystallized (ethyl acetate/hexane) and further recrystallized (ethyl acetate/hexane) to obtain the title compound (258 mg).

$^1$H NMR (300 MHz, DMSO-$d_6$) delta 0.58-0.65 (2H, m), 0.67-0.75 (2H, m), 0.91-1.06 (7H, m), 1.23 (6H, d, J=5.9 Hz), 1.63-1.89 (5H, m), 2.03-2.27 (3H, m), 2.63 (2H, q, J=7.2 Hz), 2.91 (2H, d, J=11.6 Hz), 3.46 (2H, s), 4.20-4.35 (1H, m), 4.60-4.75 (1H, m), 6.27 (1H, d, J=7.2 Hz), 6.73 (1H, s), 7.59 (1H, d, J=7.3 Hz).

Example 49

1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid A) 4-Bromo-3-fluoro-2-methoxybenzaldehyde Sodium methoxide (28% methanol solution, 69.1 g) was added to a solution of 4-bromo-2,3-difluorobenzaldehyde (52.8 g) in methanol (600 mL) at room temperature. The mixture was refluxed under nitrogen atmosphere for 2 hours and concentrated in vacuo to about ¼ volume. The mixture was diluted with ethyl acetate and water. The mixture was extracted with ethyl acetate. The organic layer was separated, washed with water and brine, dried over anhydrous magnesium sulfate and concentrated in vacuo to give the title compound (52.3 g).

$^1$H NMR (300 MHz, CDCl$_3$) delta 4.12 (3H, d, J=2.9 Hz), 7.34 (1H, dd, J=8.5, 5.7 Hz), 7.50 (1H, dd, J=8.5, 1.6 Hz), 10.34 (1H, s).

B) 4-Bromo-3-fluoro-2-hydroxybenzaldehyde

48% Hydrobromic acid (254 mL) was added to a solution of 4-bromo-3-fluoro-2-methoxybenzaldehyde (52.3 g) in acetic acid (350 mL) at room temperature. The mixture was stirred at 120 C under nitrogen atmosphere for 16 hours and concentrated in vacuo. The residue was diluted with ethyl acetate and water. The mixture was extracted with ethyl acetate. The organic layer was separated, washed with water and brine, dried over anhydrous magnesium sulfate and concentrated in vacuo. The residue was triturated with diisopropyl ether and collected by filtration to give the title compound (34.6 g).

$^1$H NMR (300 MHz, DMSO-$d_6$) delta 7.26 (1H, dd, J=8.5, 5.9 Hz), 7.42 (1H, dd, J=8.5, 1.4 Hz), 10.25 (1H, s), 11.36 (1H, brs).

C) 2,4'-Difluoro-3-hydroxybiphenyl-4-carbaldehyde (4-Fluorophenyl)boronic acid (33.2 g), 2M aqueous sodium carbonate solution (237 mL), palladium (II) acetate (2.49 g) and dicyclohexylphosphino-2',6'-dimethoxy-1,1'-biphenyl (9.74 g) were added to a solution of 4-bromo-3-fluoro-2-hydroxybenzaldehyde (34.6 g) in DME (350 mL) at room temperature. The mixture was stirred at 100 C under argon atmosphere for 16 hours. The mixture was cooled to room temperature. Water (700 mL) was added to the reaction mixture. The mixture was concentrated in vacuo to remove DME. The precipitate was collected by filtration and washed with water. The aqueous filtrate was set aside for further purification. Then the solid was washed with ethyl acetate. The solid was added to a mixture of ethyl acetate and 1M hydrochloric acid. The mixture was stirred at room temperature for 1 hour and filtrated through celite. The filtrate was extracted with ethyl acetate. The organic layer was separated, washed with water and brine, dried over anhydrous magnesium sulfate and concentrated in vacuo to give the title compound (20.6 g).

The aqueous filtrate was neutralized with 1M hydrochloric acid and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (8.96 g).

$^1$H NMR (300 MHz, DMSO-$d_6$) delta 7.05-7.15 (1H, m), 7.30-7.42 (2H, m), 7.56 (1H, dd, J=8.2, 1.3 Hz), 7.61-7.72 (2H, m), 10.29 (1H, s), 11.02 (1H, brs).

D) 6-Bromo-2,4'-difluoro-3-hydroxybiphenyl-4-carbaldehyde

Dibromoisocyanuric acid (24.8 g) was added to a solution of 2,4'-difluoro-3-hydroxybiphenyl-4-carbaldehyde (33.7 g) in DMF (400 mL) at room temperature. The mixture was stirred at the same temperature under nitrogen atmosphere for 3 hours. The mixture was quenched with aqueous saturated sodium thiosulfate solution at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (33.1 g).

$^1$H NMR (300 MHz, DMSO-$d_6$) delta 7.32-7.48 (4H, m), 7.77 (1H, d, J=1.7 Hz), 10.27 (1H, s), 11.28 (1H, brs).

E) 6-Bromo-2,4'-difluoro-3-isopropoxybiphenyl-4-carbaldehyde

2-Iodopropane (21.7 g) was added to a mixture of 6-bromo-2,4'-difluoro-3-hydroxybiphenyl-4-carbaldehyde (26.7 g) and potassium carbonate (23.6 g) in DMF (250 mL) at room temperature. The mixture was stirred at 60 C under nitrogen atmosphere for 3 hours. The mixture was quenched with water at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (28.5 g).

$^1$H NMR (300 MHz, DMSO-$d_6$) delta 1.34 (6H, d, J=6.0 Hz), 4.50-4.65 (1H, m), 7.32-7.42 (2H, m), 7.43-7.53 (2H, m), 7.83 (1H, d, J=1.7 Hz), 10.26 (1H, s).

F) 6-Cyclopropyl-2,4'-difluoro-3-isopropoxybiphenyl-4-carbaldehyde

Cyclopropylboronic acid (13.8 g), dicyclohexyl(2',6'-dimethoxy-[1,1'-biphenyl]-2-yl)phosphine (6.58 g), tris(dibenzylideneacetone)dipalladium (0) (7.34 g) and 2M aqueous sodium carbonate solution (120 mL) were added to a solution of 6-bromo-2,4'-difluoro-3-isopropoxybiphenyl-4-carbaldehyde (28.5 g) in toluene (250 mL) at room temperature. The mixture was stirred at 100 C under argon atmosphere for 16 hours. The mixture was filtrated through celite. The filtrate was extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (24.8 g).

$^1$H NMR (300 MHz, DMSO-d$_6$) delta 0.61-0.70 (2H, m), 0.75-0.85 (2H, m), 1.31 (6H, d, J=6.1 Hz), 1.59 (1H, tt, J=8.4, 5.3 Hz), 4.41-4.56 (1H, m), 7.15 (1H, d, J=1.0 Hz), 7.30-7.41 (2H, m), 7.43-7.52 (2H, m), 10.28 (1H, s).

G) Tert-butyl 4-(((4-methylphenyl)sulfonyl)oxy) piperidine-1-carboxylate

4-Methylbenzenesulfonyl chloride (52.1 g) was added to a solution of tert-butyl 4-hydroxypiperidine-1-carboxylate (50.0 g) in pyridine (248 mL) at room temperature. The mixture was stirred at room temperature overnight. After evaporation of the solvent, water and ethyl acetate were added to the residue. The organic layer was separated, washed with 1M hydrochloric acid and brine, dried over anhydrous magnesium sulfate and concentrated in vacuo. The residue was triturated in diisopropyl ether at 0 C ("C" represents "degrees Celsius") to give the title compound (76.1 g).

$^1$H NMR (300 MHz, CDCl$_3$) delta 1.43 (9H, s), 1.57-1.88 (4H, m), 2.45 (3H, s), 3.14-3.32 (2H, m), 3.49-3.68 (2H, m), 4.61-4.73 (1H, m), 7.34 (2H, d, J=8.0 Hz), 7.80 (2H, d, J=8.3 Hz).

H) 2-Fluoro-4-iodo-3-methylpyridine n-Butyl lithium (1.6M hexane solution, 53.8 mL) was added to a solution of diisopropylamine (8.71 g) in THF (200 mL) at −10 C. After being stirred at the same temperature under nitrogen atmosphere for 1 hour, a solution of 2-fluoro-3-iodopyridine (18.3 g) in THF (70 mL) was added to the reaction mixture at −78 C. The mixture was stirred at the same temperature under nitrogen atmosphere for 1 hour. A solution of iodomethane (12.8 g) in THF (30 mL) was added to the reaction mixture at −78 C. The mixture was stirred at the same temperature under nitrogen atmosphere for 2 hours. The mixture was quenched with aqueous saturated ammonium chloride solution at 0 C and extracted with ethyl acetate. The organic layer was separated, washed with water and brine, dried over anhydrous magnesium sulfate and concentrated in vacuo. The residue was passed through NH-silica and concentrated in vacuo. The residue was purified by a silica gel column chromatography (hexane/ethyl acetate) to give the title compound (17.2 g).

$^1$H NMR (300 MHz, CDCl$_3$) delta 2.39 (3H, d, J=1.5 Hz), 7.57-7.63 (1H, m), 7.65-7.70 (1H, m).

I) 4-Iodo-3-methylpyridin-2(1H)-one

12M Hydrochloric acid (13 mL) was added to a solution of 2-fluoro-4-iodo-3-methylpyridine (12.2 g) in DME (15 mL) at room temperature. The mixture was stirred at 100 C for 1.5 hours with an alkali trap. Water (150 mL) was added to the reaction mixture at room temperature. The mixture was stirred at the same temperature for 2 hours. The precipitate was collected by filtration, washed with water. A suspension of the solid in ethanol (20 mL) was stirred at 80 C for 30 minutes. Diisopropyl ether (150 mL) was added to the mixture. The mixture was stirred at room temperature for 30 minutes. The precipitate was collected by filtration, washed with diisopropyl ether to give the title compound (9.82 g).

$^1$H NMR (300 MHz, DMSO-d$_6$) delta 2.14 (3H, s), 6.55 (1H, d, J=6.9 Hz), 6.96 (1H, dd, J=6.9, 0.7 Hz), 11.68 (1H, brs).

J) Tert-butyl 4-(4-iodo-3-methyl-2-oxopyridin-1 (2H)-yl)piperidine-1-carboxylate Tert-butyl 4-(((4-methylphenyl)sulfonyl)oxy)piperidine-1-carboxylate (21.7 g) was added to a mixture of 4-iodo-3-methylpyridin-2(1H)-one (8.98 g) and potassium carbonate (21.1 g) in 1-methoxy-2-(2-methoxyethoxyl)ethane (160 mL) at room temperature. The mixture was stirred at 100 C under nitrogen atmosphere for 22 hours. The mixture was quenched with water at room temperature and extracted with ethyl acetate. The organic layer was separated, washed with water and brine, dried over anhydrous magnesium sulfate and concentrated in vacuo. Toluene was added to the residue. The mixture was concentrated in vacuo. The residue was purified by a silica gel column chromatography (hexane/ethyl acetate) to give the title compound (12.9 g).

$^1$H NMR (300 MHz, CDCl$_3$) delta 1.47 (9H, s), 1.57-1.72 (2H, m), 1.88 (2H, d, J=13.4 Hz), 2.35 (3H, s), 2.87 (2H, t, J=12.7 Hz), 4.29 (2H, d, J=11.1 Hz), 4.99 (1H, tt, J=12.3, 3.8 Hz), 6.63 (1H, d, J=7.4 Hz), 6.81 (1H, d, J=7.4 Hz).

K) Methyl 1-(1-(tert-butoxycarbonyl)piperidin-4-yl)-3-methyl-2-oxo-1,2-dihydropyridine-4-carboxylate

[1,1'-Bis(diphenylphosphino)ferrocene]dichloropalladium (II) (416 mg), triethylamine (1.59 mL) and methanol (6.91 mL) was added to a solution of tert-butyl 4-(4-iodo-3-methyl-2-oxopyridin-1(2H)-yl)piperidine-1-carboxylate (2.38 g) in DMF (15 mL) at room temperature. The mixture was stirred at 90 C under 0.5 MPa of carbon monoxide atmosphere for 7 hours. The mixture was quenched with water at room temperature and filtrated through celite. The filtrate was extracted with ethyl acetate. The organic layer was separated, washed with water and brine, dried over anhydrous magnesium sulfate and concentrated in vacuo. The residue was passed through a silica gel (NH, hexane/ethyl acetate) and concentrated in vacuo. The residue was triturated with diisopropyl ether/hexane and collected by filtration to give the title compound (1.77 g).

$^1$H NMR (300 MHz, CDCl$_3$) delta 1.48 (9H, s), 1.60-1.76 (2H, m), 1.89 (2H, d, J=12.8 Hz), 2.37 (3H, s), 2.81-2.99 (2H, m), 3.90 (3H, s), 4.28 (2H, brs), 5.00-5.16 (1H, m), 6.48 (1H, d, J=7.4 Hz), 7.18 (1H, d, J=7.4 Hz).

L) Methyl 3-methyl-2-oxo-1-(piperidin-4-yl)-1,2-dihydropyridine-4-carboxylate hydrochoride To 2M hydrogen chloride (2-propanol solution 2.85 L) was added methyl 1-(1-(tert-butoxycarbonyl)piperidin-4-yl)-3-methyl-2-oxo-1,2-dihydropyridine-4-carboxylate (200 g) at room temperature. The mixture was stirred at room temperature for 18 hours. Diisopropyl ether (11.5 L) was added to the reaction mixture and the precipitate was collected by filtration, washed with diisopropyl ether (2.86 L) to give the title compound (163.2 g).

$^1$H NMR (300 MHz, DMSO-d$_6$) delta 1.93 (2H, d, J=11.3 Hz), 2.06-2.25 (5H, m), 3.02-3.18 (2H, m), 3.40 (2H, d, J=12.8 Hz), 3.84 (3H, s), 4.98 (1H, tt, J=12.2, 3.9 Hz), 6.48 (1H, d, J=7.6 Hz), 7.50 (1H, d, J=7.2 Hz), 9.08 (2H, brs).

M) Methyl 1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylate hydrochloride Triethylamine (35.3 g) was added to a suspension of methyl 3-methyl-2-oxo-1-(piperidin-4-yl)-1,2-dihydropyridine-4-carboxylate hydrochoride (100 g) in THF (2.00 L) at room temperature. After being stirred at the same temperature for 30 minutes, 6-cyclopropyl-2,4'-difluoro-3-isopropoxybiphenyl-4-carbaldehyde (121 g) was added to the reaction mixture. The mixture was stirred at room temperature for 30 minutes. Sodium triacetoxyhydroborate (111 g) and acetic acid (20.9 g) were added to the reaction mixture. The mixture was stirred at room temperature for 16 hours. Aqueous saturated sodium hydrogen carbonate solution (1.30 L) and water (1.30 L) were added to the mixture at room temperature. The mixture was extracted with ethyl acetate (10 L). The organic layer was separated, washed with brine (4.00 L), dried over anhydrous sodium sulfate and concentrated in vacuo. The residue was dissolved in ethyl acetate (1.00 L). 4M hydrogen chloride (ethyl acetate solution, 87 ml) was added to the mixture at room temperature. Then crystalline seeds were added to the mixture. The mixture was diluted with diisopropyl ether (2.00 L) and stirred at room temperature for 1 hour. The precipitate was collected by filtration and washed with diisopropyl ether (1.50 L) to give the title compound (183.7 g).

$^1$H NMR (300 MHz, DMSO-d$_6$) delta 0.74-0.89 (4H, m), 1.30 (6H, d, J=6.0 Hz), 1.48-1.64 (1H, m), 1.93-2.06 (2H, m), 2.18 (3H, s), 2.29-2.47 (2H, m), 3.24-3.40 (2H, m), 3.41-3.53 (2H, m), 3.84 (3H, s), 4.30 (2H, d, J=4.9 Hz), 4.37-4.50 (1H, m), 4.99-5.17 (1H, m), 6.50 (1H, d, J=7.2 Hz), 7.25-7.39 (3H, m), 7.39-7.51 (3H, m), 10.90 (1H, brs).

N) 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid 2M aqueous sodium hydroxide solution (690 mL) was added to a solution of methyl 1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylate hydrochloride (270 g) in methanol (1.35 L) at room temperature. The mixture was stirred at 50 C for 2 hours and cooled to room temperature. Water (2.70 L) was added to the reaction mixture. The mixture was concentrated in vacuo to remove methanol and neutralized with 2M hydrochloric acid (460 mL) at room temperature. Crystalline seeds were added to the mixture. The mixture was stirred at room temperature for 17 hours. The precipitate was collected by filtration, washed with water (7.00 L) and dried in vacuo at 65 C for 24 hours to give the title compound (245.3 g).

$^1$H NMR (300 MHz, DMSO-d$_6$) delta 0.55-0.65 (2H, m), 0.71-0.84 (2H, m), 1.26 (6H, d, J=5.7 Hz), 1.51-1.65 (1H, m), 1.68-1.96 (4H, m), 2.10-2.26 (5H, m), 2.98 (2H, d, J=11.3 Hz), 3.56 (2H, s), 4.26-4.43 (1H, m), 4.61-4.79 (1H, m), 6.36 (1H, d, J=7.6 Hz), 6.84 (1H, s), 7.25-7.36 (2H, m), 7.38-7.49 (2H, m), 7.67 (1H, d, J=7.2 Hz).

O) 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid (350 g) was dissolved in 90% aqueous ethanol solution (700 mL) at 70 C. The mixture was filtrated through a filter paper with ethyl acetate (1.00 L). Ethyl acetate (4.25 L) was added to the filtrate at 65 C (inside temperature). Crystalline seeds were added to the mixture. The mixture was slowly cooled to 45 C (inside temperature) and stirred at the same temperature for 18 hours. The mixture was cooled to 30 C. The precipitate was collected by filtration, washed with ethyl acetate (1.50 L) and dried in vacuo at 70 C to give the title compound (306 g).

$^1$H NMR (300 MHz, DMSO-d$_6$) delta 0.55-0.64 (2H, m), 0.72-0.82 (2H, m), 1.26 (6H, d, J=6.0 Hz), 1.51-1.64 (1H, m), 1.67-1.94 (4H, m), 2.11-2.26 (5H, m), 2.99 (2H, d, J=11.3 Hz), 3.57 (2H, s), 4.27-4.43 (1H, m), 4.62-4.78 (1H, m), 6.37 (1H, d, J=7.2 Hz), 6.84 (1H, s), 7.25-7.36 (2H, m), 7.37-7.48 (2H, m), 7.67 (1H, d, J=7.2 Hz).

mp 144.8-145.7 C

Example 50

1-(1-((6-Cyclopropyl-3-ethoxy-2,4'-difluorobiphenyl-4-yl)methyl)piperidin-4-yl)-3-methyl-2-oxo-1,2-dihydropyridine-4-carboxylic acid A) Methyl 1-(1-((6-cyclopropyl-3-ethoxy-2,4'-difluorobiphenyl-4-yl)methyl)piperidin-4-yl)-3-methyl-2-oxo-1,2-dihydropyridine-4-carboxylate A mixture of methyl 1-(1-(tert-butoxycarbonyl)piperidin-4-yl)-3-methyl-2-oxo-1,2-dihydropyridine-4-carboxylate (306 mg) and formic acid (8 mL) was stirred at 70 C for 30 minutes in a nitrogen atmosphere, and then, the solvent was distilled off under reduced pressure. Sodium triacetoxyborohydride (370 mg) was added at room temperature to a mixture of the obtained residue, 6-cyclopropyl-3-ethoxy-2,4'-difluorobiphenyl-4-carbaldehyde (290 mg), and THF (8 mL), and the mixture was stirred at the same temperature as above for 15 hours in a nitrogen atmosphere. A saturated aqueous solution of sodium bicarbonate was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (301 mg).

$^1$H NMR (300 MHz, CDCl$_3$) delta 0.58-0.65 (2H, m), 0.74-0.82 (2H, m), 1.39 (3H, t, J=7.0 Hz), 1.57-1.67 (1H, m), 1.72-1.94 (4H, m), 2.28 (2H, td, J=11.6, 2.5 Hz), 2.37 (3H, s), 3.05 (2H, d, J=11.8 Hz), 3.58 (2H, s), 3.90 (3H, s), 4.04-4.13 (2H, m), 4.87-5.01 (1H, m), 6.47 (1H, d, J=7.4 Hz), 6.71 (1H, d, J=1.3 Hz), 7.09-7.18 (2H, m), 7.27-7.37 (3H, m).

B) 1-(1-((6-Cyclopropyl-3-ethoxy-2,4'-difluorobiphenyl-4-yl)methyl)piperidin-4-yl)-3-methyl-2-oxo-1,2-dihydropyridine-4-carboxylic acid A 2 M aqueous sodium hydroxide solution (2 mL) was added at room temperature to an ethanol (8 mL) solution of methyl 1-(1-((6-cyclopropyl-3-ethoxy-2,4'-difluorobiphenyl-4-yl)methyl)piperidin-4-yl)-3-methyl-2-oxo-1,2-dihydropyridine-4-carboxylate (283 mg), and the mixture was stirred at 80 C for 3 hours in a nitrogen atmosphere. Then, the solvent was distilled off under reduced pressure. Water was added to the obtained residue, and the mixture was neutralized with 2 M hydrochloric acid. The deposited crystal was collected by filtration and dissolved in ethanol. The obtained solution was filtered, and then, the filtrate was concentrated under reduced pressure. The obtained residue was crystallized (hexane/ethyl acetate) and further recrystallized (hexane/ethyl acetate) to obtain the title compound (151 mg).

$^1$H NMR (300 MHz, DMSO-d$_6$) delta 0.57-0.65 (2H, m), 0.72-0.80 (2H, m), 1.33 (3H, t, J=7.0 Hz), 1.51-1.63 (1H, m), 1.71-1.98 (4H, m), 2.17 (3H, s), 2.22-2.36 (2H, m), 3.03 (2H, d, J=11.4 Hz), 3.62 (2H, s), 4.04 (2H, q, J=7.0 Hz), 4.65-4.80

(1H, m), 6.38 (1H, d, J=7.3 Hz), 6.83 (1H, s), 7.26-7.36 (2H, m), 7.38-7.47 (2H, m), 7.65 (1H, d, J=7.4 Hz).

Example 51

1-(1-((2-Cyclopropyl-4'-fluoro-5-isopropoxybiphenyl-4-yl)methyl)piperidin-4-yl)-3-ethyl-2-oxo-1,2-dihydropyridine-4-carboxylic acid A) Methyl 1-(1-((2-cyclopropyl-4'-fluoro-5-isopropoxybiphenyl-4-yl)methyl)piperidin-4-yl)-3-ethyl-2-oxo-1,2-dihydropyridine-4-carboxylate A mixture of methyl 1-(1-(tert-butoxycarbonyl)piperidin-4-yl)-3-ethyl-2-oxo-1,2-dihydropyridine-4-carboxylate (300 mg) and formic acid (2 mL) was stirred at 70 C for 1 hour in a nitrogen atmosphere, and then, the solvent was distilled off under reduced pressure. Sodium triacetoxyborohydride (262 mg) was added to a mixture of the obtained residue, 2-cyclopropyl-4'-fluoro-5-isopropoxybiphenyl-4-carbaldehyde (246 mg), and THF (5 mL), and the mixture was stirred overnight at room temperature. A saturated aqueous solution of sodium bicarbonate was added to the reaction mixture at room temperature, followed by extraction with ethyl acetate. The solvent in the obtained organic layer was distilled off under reduced pressure. The obtained residue was purified by silica gel column chromatography (hexane/ethyl acetate) to obtain the title compound (390 mg).
MS (ESI+): [M+H]$^+$ 547.5.

B) 1-(1-((2-Cyclopropyl-4'-fluoro-5-isopropoxybiphenyl-4-yl)methyl)piperidin-4-yl)-3-ethyl-2-oxo-1, 2-dihydropyridine-4-carboxylic acid A 2 M aqueous sodium hydroxide solution (1 mL) was added at room temperature to a methanol (4 mL) solution of methyl 1-(1-((2-cyclopropyl-4'-fluoro-5-isopropoxybiphenyl-4-yl)methyl)piperidin-4-yl)-3-ethyl-2-oxo-1,2-dihydropyridine-4-carboxylate (390 mg), and the mixture was stirred at 60 C for 1 hour in a nitrogen atmosphere and then neutralized with 1 M hydrochloric acid. The reaction mixture was stirred at room temperature for 30 minutes, and then, the deposited crystal was collected by filtration and recrystallized (diisopropyl ether/ethanol) to obtain the title compound (240 mg).
$^1$H NMR (400 MHz, DMSO-d$_6$) delta 0.51-0.58 (2H, m), 0.72-0.79 (2H, m), 1.03 (3H, t, J=7.3 Hz), 1.26 (6H, d, J=6.0 Hz), 1.69-1.79 (3H, m), 1.80-1.92 (2H, m), 2.20 (2H, t, J=11.3 Hz), 2.65 (2H, q, J=7.2 Hz), 3.01 (2H, d, J=11.2 Hz), 3.54 (2H, s), 4.55-4.64 (1H, m), 4.64-4.75 (1H, m), 6.32 (1H, d, J=7.2 Hz), 6.77 (1H, s), 6.98 (1H, s), 7.26 (2H, t, J=8.9 Hz), 7.44-7.53 (2H, m), 7.65 (1H, d, J=7.3 Hz).

Example 60

1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid hydrochloride A) 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid hydrochloride 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid (15.0 g) was dissolved in isopropanol (150 mL) at 60 C. The mixture was cooled to room temperature. 2M hydrogen chloride (isopropanol solution, 21.0 mL) was added to the mixture at room temperature. After being stirred at room temperature for 30 minutes, diisopropyl ether (300 mL) and crystalline seeds were added to the mixture. The mixture was stirred for 1 hour under nitrogen atmosphere. The precipitate was collected by filtration, washed with diisopropyl ether (150 mL) and heptane (100 mL), and then dried at 60 C to give the title compound (14.3 g).
$^1$H NMR (300 MHz, DMSO-d$_6$) delta 0.74-0.88 (4H, m), 1.30 (6H, d, J=6.0 Hz), 1.49-1.62 (1H, m), 1.98 (2H, d, J=12.1 Hz), 2.19 (3H, s), 2.37 (2H, d, J=11.3 Hz), 3.21-3.52 (4H, m), 4.30 (2H, brs), 4.43 (1H, dt, J=12.0, 5.9 Hz), 5.07 (1H, brs), 6.48 (1H, d, J=7.6 Hz), 7.26 (1H, s), 7.30-7.38 (2H, m), 7.39-7.48 (3H, m), 10.86 (1H, brs), 13.57 (1H, brs).

B) 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid hydrochloride 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid hydrochloride (20.0 g) was dissolved in isopropanol/2-butanone (190 mL/190 mL) at 80 C. The mixture was filtrated through a filter paper with isopropanol/2-butanone (10 mL/10 mL). Heptane (250 mL) and crystalline seeds were added to the mixture at 60 C. Then heptane (350 mL) was added to the mixture at 55 to 60 C. The mixture was stirred at same temperature for 1.5 hour and cooled to room temperature for 2 hours. The mixture was stirred at 12 C for 1 hour. The precipitate was collected by filtration, and dried in vacuo at 60 C for 8 hours to give the title compound (18.2 g).
$^1$H NMR (300 MHz, DMSO-d$_6$) delta 0.73-0.91 (4H, m), 1.30 (6H, d, J=6.0 Hz), 1.48-1.62 (1H, m), 1.97 (2H, d, J=11.7 Hz), 2.19 (3H, s), 2.33-2.48 (2H, m), 3.22-3.53 (4H, m), 4.30 (2H, brs), 4.42 (1H, dt, J=12.1, 6.0 Hz), 5.10 (1H, t, J=12.1 Hz), 6.48 (1H, d, J=7.2 Hz), 7.27-7.39 (3H, m), 7.39-7.49 (3H, m), 11.18 (1H, brs), 13.56 (1H, brs).
mp 242 C Example 61

1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid 1/2 hydrosulfate 0.5M Sulfuric acid (2 mL) was added to a solution of 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid (515 mg) in ethanol (5 mL) at room temperature. The mixture was stirred at the same temperature under nitrogen atmosphere for 1 hour. Diisopropyl ether (15 mL) was added to the reaction mixture. The mixture was stirred at room temperature under nitrogen atmosphere for 1 hour. The precipitate was collected by filtration. The solid was recrystallized from ethanol-heptane to give the title compound (422 mg).
$^1$H NMR (300 MHz, DMSO-d$_6$) delta 0.59-0.71 (2H, m), 0.75-0.86 (2H, m), 1.29 (6H, d, J=6.0 Hz), 1.51-1.65 (1H, m), 1.80-2.13 (4H, m), 2.18 (3H, s), 3.31 (4H, brs), 3.94 (2H, brs), 4.35-4.50 (1H, m), 4.83 (1H, brs), 6.42 (1H, d, J=7.3 Hz), 6.93 (1H, s), 7.26-7.37 (2H, m), 7.38-7.48 (2H, m), 7.52-7.64 (1H, m).
mp 233 C

Example 62

1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid maleate Maleic acid (111 mg) was added to a solution of 1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylic acid (513 mg) in ethanol (5 mL) at room temperature. The mixture was stirred at the same temperature under nitrogen atmosphere for 1 hour and concentrated in vacuo. The residue was crystallized from ethyl acetate-hexane to give a colorless solid. The solid was recrystallized from ethanol-heptane to give the title compound (573 mg).

$^1$H NMR (300 MHz, DMSO-$d_6$) delta 0.63-0.72 (2H, m), 0.77-0.86 (2H, m), 1.30 (6H, d, J=6.0 Hz), 1.53-1.67 (1H, m), 1.87-2.16 (4H, m), 2.19 (3H, s), 3.31 (4H, brs), 4.11 (2H, brs), 4.44 (1H, brs), 4.89 (1H, brs), 6.07 (2H, s), 6.45 (1H, d, J=7.3 Hz), 6.98 (1H, s), 7.28-7.38 (2H, m), 7.39-7.54 (3H, m).

mp 193 C

Compounds of Examples 8 to 42, 46, 48, and 52 to 59 shown in the table below were produced according to the methods shown above in Examples or methods equivalent thereto.

The compounds of Examples produced according to the production methods mentioned above and the methods shown in Examples or methods equivalent thereto are shown in Table 1 below. Table 1 includes the compound names, structural formulas, and actual MS measurement value data of the compounds of Examples. The actual MS measurement values are indicated by values found in a positive mode (ESI+) or a negative mode (ESI−).

TABLE 1

| Example # | IUPAC NAME | Structure | MS |
|---|---|---|---|
| 1 | 1-(1-(4-cyclobutyl-5-cyclopropyl-2-ethoxybenzyl)piperidin-4-yl)-2-oxo-1,2-dihydropyridine-4-carboxylic acid | 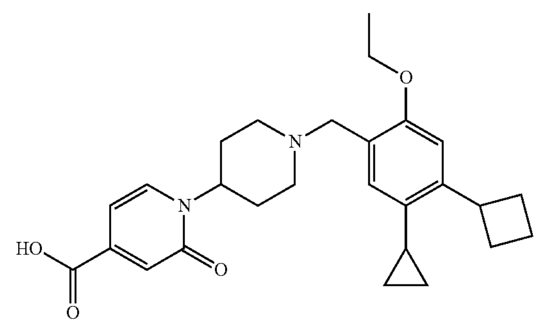 [SMILES: CCOc1cc(C2CCC2)c(C2CC2)cc1CN1CCC(n2ccc(C(=O)O)cc2=O)CC1] | 451.2 |
| 2 | 1-(1-((5-cyclopropyl-6-(4-fluorophenyl)-2-isopropoxypyridin-3-yl)methyl)piperidin-4-yl)-2-oxo-1,2-dihydropyridine-4-carboxylic acid | 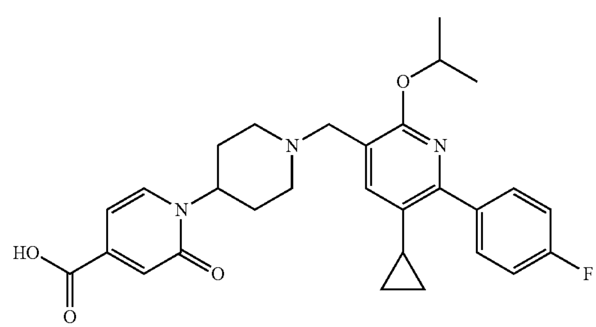 [SMILES: CC(C)Oc1nc(-c2ccc(F)cc2)c(C2CC2)cc1CN1CCC(n2ccc(C(=O)O)cc2=O)CC1] | 506.2 |
| 3 | 1-(1-((2-cyclopropyl-4'-fluoro-5-isopropoxybiphenyl-4-yl)methyl)piperidin-4-yl)-2-oxo-1,2-dihydropyridine-4-carboxylic acid | 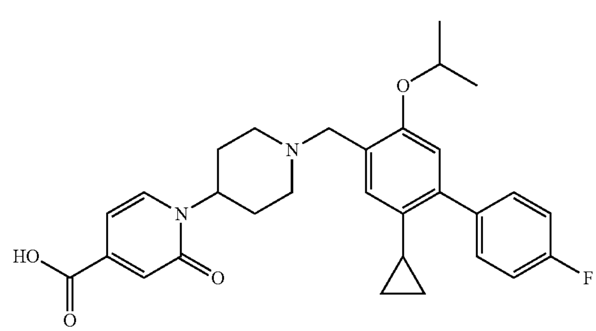 [SMILES: CC(C)Oc1cc(-c2ccc(F)cc2)c(C2CC2)cc1CN1CCC(n2ccc(C(=O)O)cc2=O)CC1] | 505.2 |

TABLE 1-continued

| Example # | IUPAC NAME | Structure | MS |
|---|---|---|---|
| 4 | 1-(1-(4,5-dicyclopropyl-2-isopropoxybenzyl)piperidin-4-yl)-2-oxo-1,2-dihydropyridine-4-carboxylic acid | 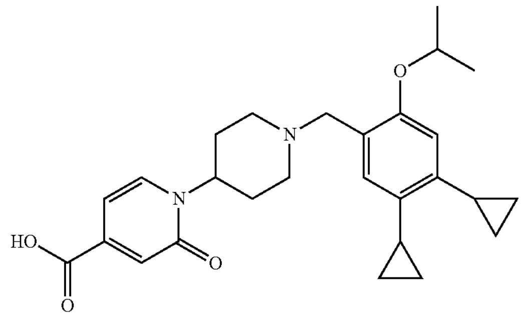 [SMILES: CC(C)Oc1cc(C2CC2)c(C2CC2)cc1CN1CCC(n2ccc(C(=O)O)cc2=O)CC1] | 451.1 |
| 5 | 1-(1-((2-chloro-6-cyclopropyl-2',4'-difluoro-3-isopropoxybiphenyl-4-yl)methyl)piperidin-4-yl)-2-oxo-1,2-dihydropyridine-4-carboxylic acid | 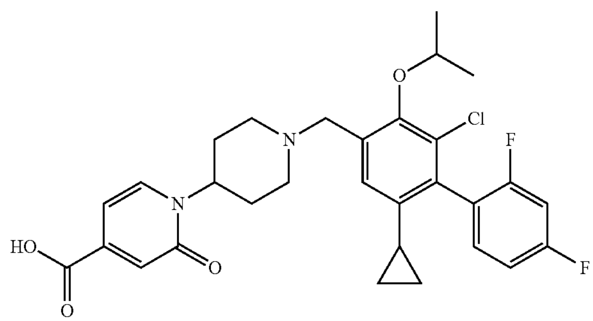 [SMILES: CC(C)Oc1c(CN2CCC(n3ccc(C(=O)O)cc3=O)CC2)cc(C2CC2)c(-c2ccc(F)cc2F)c1Cl] | 557.2 |
| 6 | 1-(1-((2-cyclopropyl-2',4'-difluoro-5-isopropoxybiphenyl-4-yl)methyl)piperidin-4-yl)-3-ethyl-2-oxo-1,2-dihydropyridine-4-carboxylic acid | 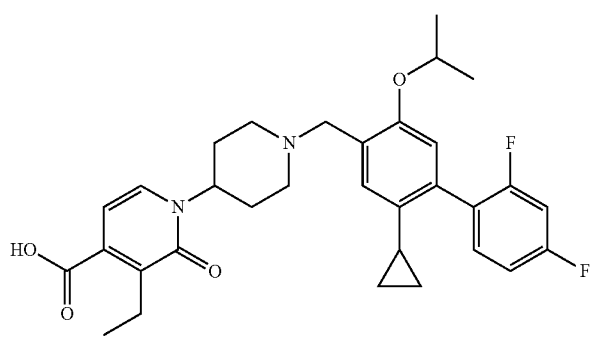 [SMILES: CCc1c(C(=O)O)ccn(C2CCN(Cc3cc(C4CC4)c(-c4ccc(F)cc4F)cc3OC(C)C)CC2)c1=O] | 551.2 |
| 7 | 1-(1-((6-cyclopropyl-2,2',4'-trifluoro-3-isopropoxybiphenyl-4-yl)methyl)piperidin-4-yl)-3-ethyl-2-oxo-1,2-dihydropyridine-4-carboxylic acid | 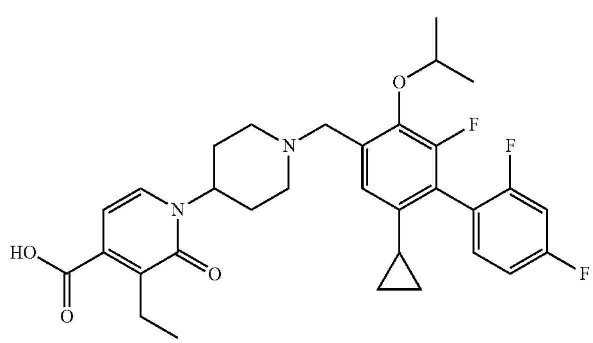 [SMILES: CCc1c(C(=O)O)ccn(C2CCN(Cc3cc(C4CC4)c(-c4ccc(F)cc4F)c(F)c3OC(C)C)CC2)c1=O] | 569.2 |

TABLE 1-continued

| Example # | IUPAC NAME | Structure | MS |
|---|---|---|---|
| 8 | 1-(1-((2,6-diethoxy-4'-fluorobiphenyl-4-yl)methyl)piperidin-4-yl)-2-oxo-1,2-dihydropyridine-4-carboxylic acid | 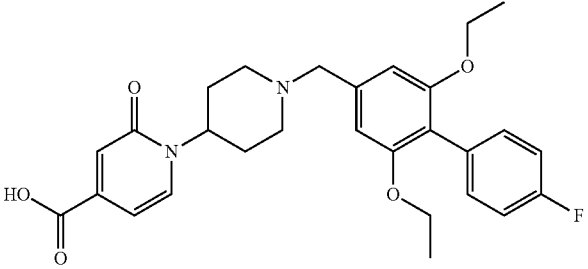 [SMILES: CCOc1cc(CN2CCC(n3ccc(C(=O)O)cc3=O)CC2)cc(OCC)c1-c1ccc(F)cc1] | 495.2 |
| 9 | 1-(1-((2-cyclopropyl-5-ethoxy-4'-fluorobiphenyl-4-yl)methyl)piperidin-4-yl)-2-oxo-1,2-dihydropyridine-4-carboxylic acid | 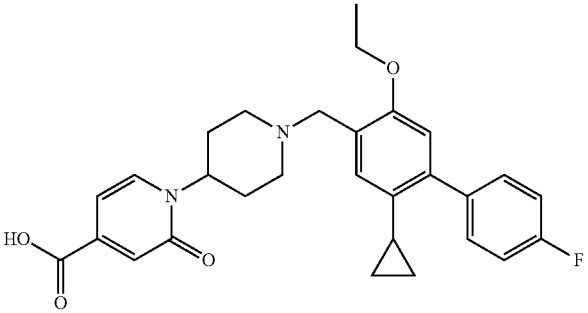 | 491.3 |
| 10 | 1-(1-((5-cyclopropyl-2-ethoxy-6-(4-fluorophenyl)pyridin-3-yl)methyl)piperidin-4-yl)-2-oxo-1,2-dihydropyridine-4-carboxylic acid | 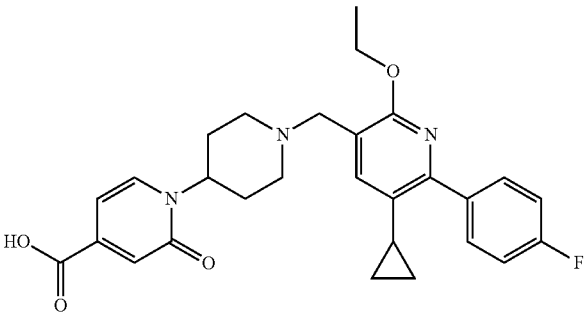 [SMILES: CCOc1nc(-c2ccc(F)cc2)c(C2CC2)cc1CN1CCC(n2ccc(C(=O)O)cc2=O)CC1] | 492.3 |
| 11 | 1-(1-((2-cyclopropyl-5-ethoxy-4'-fluorobiphenyl-4-yl)methyl)piperidin-4-yl)-2-oxo-1,2-dihydropyridine-4-carboxamide | 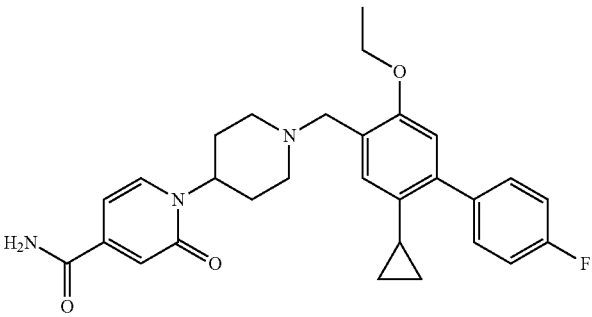 [SMILES: CCOc1cc(-c2ccc(F)cc2)c(C2CC2)cc1CN1CCC(n2ccc(C(N)=O)cc2=O)CC1] | 490.2 |
| 12 | 1-(1-((2-cyclopropyl-6-ethoxy-4'-fluorobiphenyl-4-yl)methyl)piperidin-4-yl)-2-oxo-1,2-dihydropyridine-4-carboxylic acid | 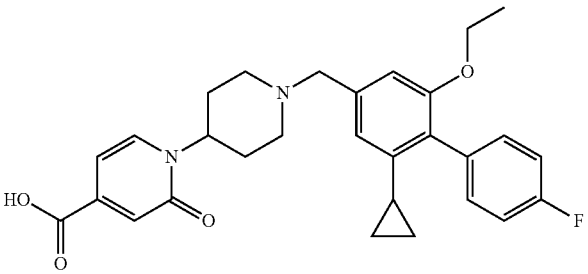 [SMILES: CCOc1cc(CN2CCC(n3ccc(C(=O)O)cc3=O)CC2)cc(C2CC2)c1-c1ccc(F)cc1] | 491.2 |

TABLE 1-continued

| Example # | IUPAC NAME | Structure | MS |
|---|---|---|---|
| 13 | 1-(1-((2-cyclobutyl-4'-fluoro-5-methoxybiphenyl-4-yl)methyl)piperidin-4-yl)-2-oxo-1,2'-dihydropyridine-4-carboxylic acid | 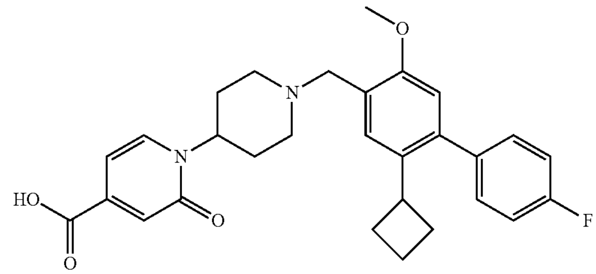 [SMILES: COc1cc(-c2ccc(F)cc2)c(C2CCC2)cc1CN1CCC(n2ccc(C(=O)O)cc2=O)CC1] | 491.2 |
| 14 | 1-(1-((2-cyclopropyl-5-ethoxy-4'-fluorobiphenyl-4-yl)methyl)piperidin-4-yl)-6-oxo-1,6-dihydropyridine-3-carboxylic acid | 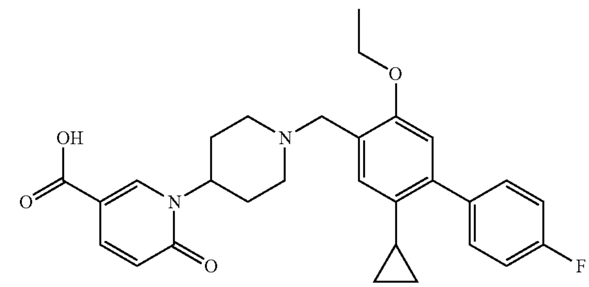 [SMILES: CCOc1cc(-c2ccc(F)cc2)c(C2CC2)cc1CN1CCC(n2cc(C(=O)O)ccc2=O)CC1] | 491.2 |
| 15 | 1-(1-((2-cyclopropyl-5-ethoxy-4'-fluorobiphenyl-4-yl)methyl)piperidin-4-yl)-5-methyl-2-oxo-1,2-dihydropyridine-4-carboxylic acid | 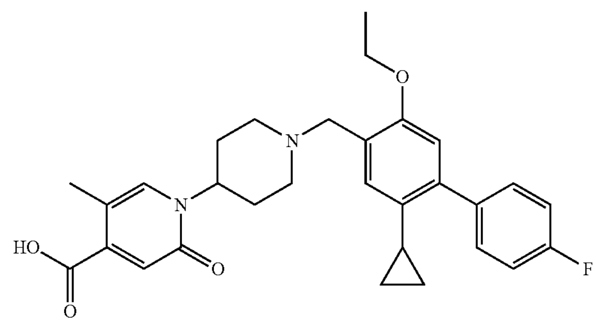 [SMILES: CCOc1cc(-c2ccc(F)cc2)c(C2CC2)cc1CN1CCC(n2cc(C)c(C(=O)O)cc2=O)CC1] | 505.2 |
| 16 | 5-bromo-1-(1-((2-cyclopropyl-5-ethoxy-4'-fluorobiphenyl-4-yl)methyl)piperidin-4-yl)-2-oxo-1,2-dihyropyridine-4-carboxylic acid | 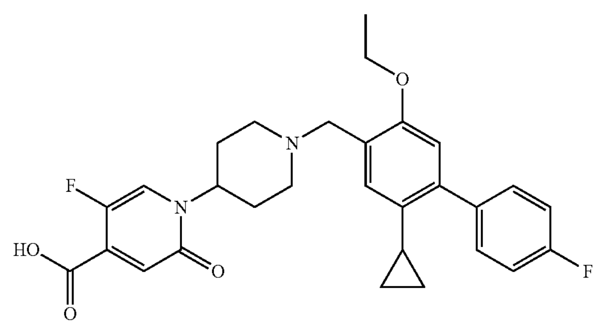 [SMILES: CCOc1cc(-c2ccc(F)cc2)c(C2CC2)cc1CN1CCC(n2cc(F)c(C(=O)O)cc2=O)CC1] | 569.1 |
| 17 | 1-(1-((2-cyclopropyl-5-ethoxy-2',4'-difluorophenyl-4-yl)methyl)piperidin-4-yl)-2-oxo-1,2-dihydropyridine-4-carboxylic acid | 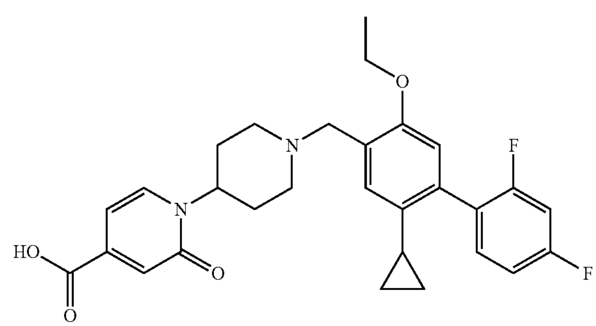 [SMILES: CCOc1cc(-c2ccc(F)cc2F)c(C2CC2)cc1CN1CCC(n2ccc(C(=O)O)cc2=O)CC1] | 509.2 |

TABLE 1-continued

| Example # | IUPAC NAME | Structure | MS |
|---|---|---|---|
| 18 | 1-(1-((2-cyclopropyl-4'-fluoro-5-methoxybiphenyl-4-yl)methyl)piperidin-4-yl)-2-oxo-1,2-dihydropyridine-4-carboxylic acid | 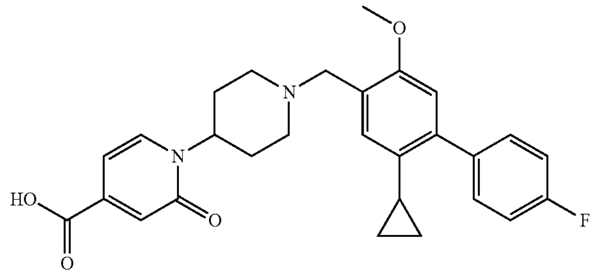 [SMILES: COc1cc(-c2ccc(F)cc2)c(C2CC2)cc1CN1CCC(n2ccc(C(=O)O)cc2=O)CC1] | 477.2 |
| 19 | 1-(1-((2-cyclopropyl-3',4'-difluoro-5-methoxybiphenyl-4-yl)methyl)piperidin-4-yl)-2-oxo-1,2-dihydropyridine-4-carboxylic acid | 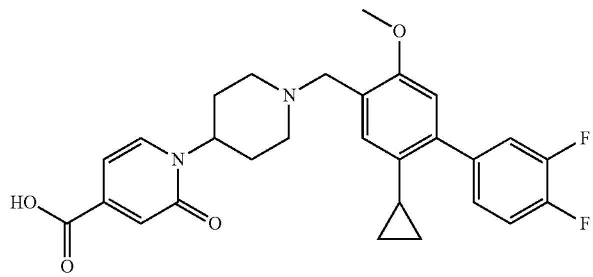 [SMILES: COc1cc(-c2ccc(F)c(F)c2)c(C2CC2)cc1CN1CCC(n2ccc(C(=O)O)cc2=O)CC1] | 495.1 |
| 20 | 1-(1-(4-cyclobutyl-5-cyclopropyl-2-isopropoxybenzyl)piperidin-4-yl)-2-oxo-1,2-dihydropyridine-4-carboxylic acid | 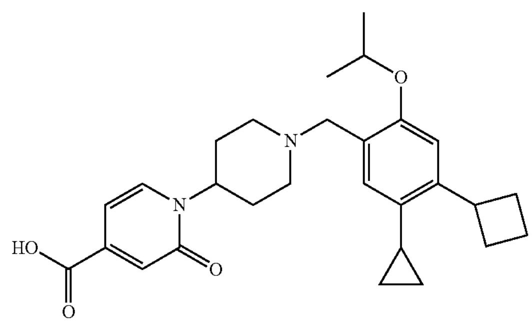 [SMILES: CC(C)Oc1cc(C2CCC2)c(C2CC2)cc1CN1CCC(n2ccc(C(=O)O)cc2=O)CC1] | 465.2 |
| 21 | 1-(1-((2-chloro-6-cyclopropyl-3-ethoxy-4'-fluorobiphenyl-4-yl)methyl)piperidin-4-yl)-2-oxo-1,2-dihydropyridine-4-carboxylic acid | 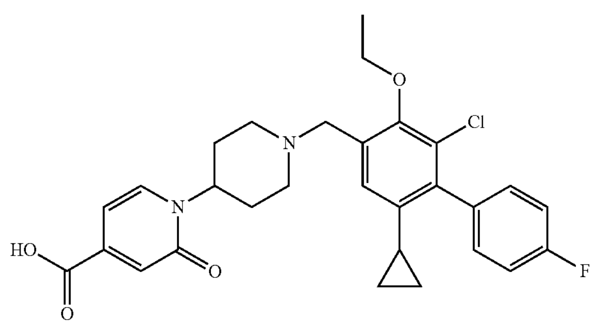 [SMILES: CCOc1c(CN2CCC(n3ccc(C(=O)O)cc3=O)CC2)cc(C2CC2)c(-c2ccc(F)cc2)c1Cl] | 525.1 |
| 22 | 1-(1-((2-cyclopropyl-3',4'-difluoro-5-isopropoxybiphenyl-4-yl)methyl)piperidin-4-yl)-2-oxo-1,2-dihydropyridine-4-carboxylic acid | 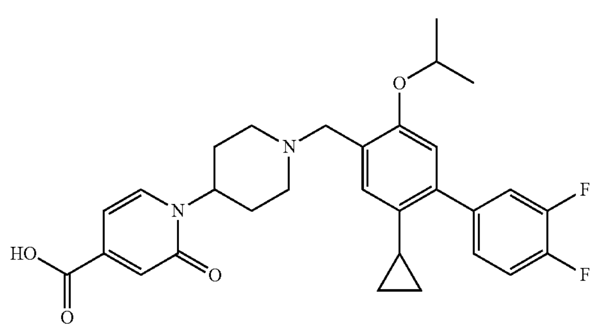 [SMILES: CC(C)Oc1cc(-c2ccc(F)c(F)c2)c(C2CC2)cc1CN1CCC(n2ccc(C(=O)O)cc2=O)CC1] | 523.2 |

TABLE 1-continued

| Example # | IUPAC NAME | Structure | MS |
|---|---|---|---|
| 23 | 1-(1-((2-cyclopropyl-2',4'-difluoro-5-isopropoxybiphenyl-4-yl)methyl)piperidin-4-yl)-2-oxo-1,2-dihydropyridine-4-carboxylic acid | 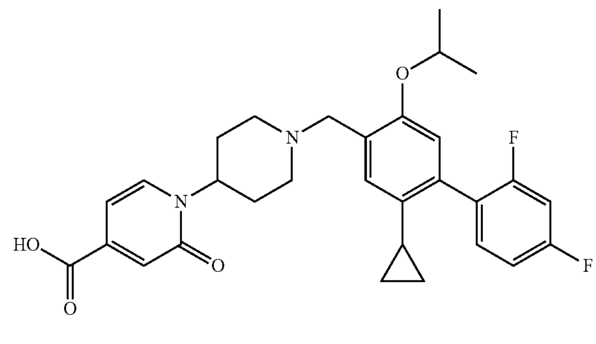 [SMILES: CC(C)Oc1cc(-c2ccc(F)cc2F)c(C2CC2)cc1CN1CCC(n2ccc(C(=O)O)cc2=O)CC1] | 523.2 |
| 24 | 1-(1-(4,5-dicyclopropyl-2-ethoxybenzyl)piperidin-4-yl)-2-oxo-1,2-dihydropyridine-4-carboxylic acid | 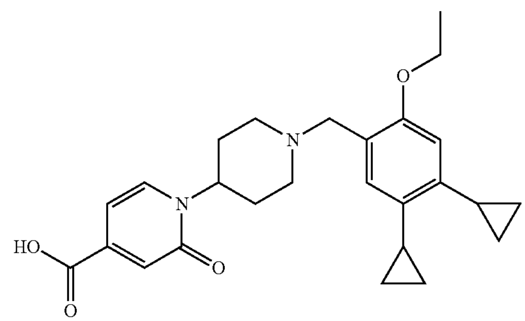 [SMILES: CCOc1cc(C2CC2)c(C2CC2)cc1CN1CCC(n2ccc(C(=O)O)cc2=O)CC1] | 437.2 |
| 25 | 1-(1-(4,5-dicyclopropyl-2-isopropoxybenzyl)piperidin-4-yl)-5-methyl-2-oxo-1,2-dihydropyridine-4-carboxylic acid | 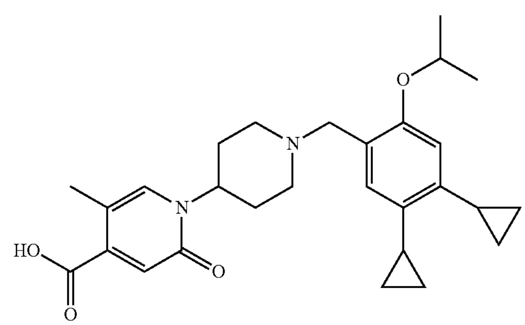 [SMILES: Cc1cn(C2CCN(Cc3cc(C4CC4)c(C4CC4)cc3OC(C)C)CC2)c(=O)cc1C(=O)O] | 465.2 |
| 26 | 5-cyclopropyl-1-(1-(4,5-dicyclopropyl-2-isopropoxybenzyl)piperidin-4-yl)-2-oxo-1,2-dihydropyridine-4-carboxylic acid | 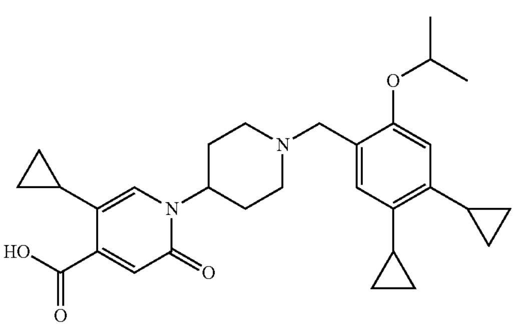 [SMILES: CC(C)Oc1cc(C2CC2)c(C2CC2)cc1CN1CCC(n2cc(C3CC3)c(C(=O)O)cc2=O)CC1] | 491.3 |

TABLE 1-continued

| Example # | IUPAC NAME | Structure | MS |
|---|---|---|---|
| 27 | 1-(1-(4,5-dicyclopropyl-2-isopropoxybenzyl)piperidin-4-yl)-2-oxo-5-propyl-1,2-dihydropyridine-4-carboxylic acid | 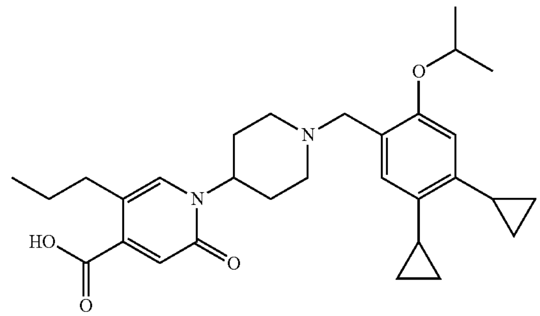 [SMILES: CCCc1cn(C2CCN(Cc3cc(C4CC4)c(C4CC4)cc3OC(C)C)CC2)c(=O)cc1C(=O)O] | 493.3 |
| 28 | 1-(1-(4,5-dicyclopropyl-2-isopropoxybenzyl)piperidin-4-yl)-3-methyl-2-oxo-1,2-dihydropyridine-4-carboxylic acid | 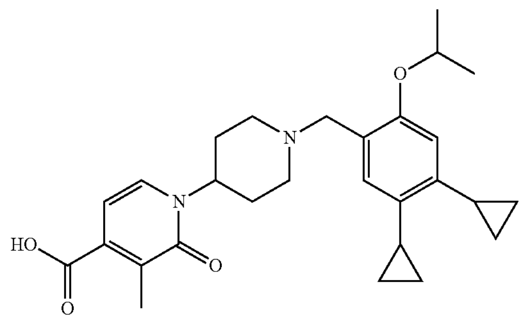 [SMILES: Cc1c(C(=O)O)ccn(C2CCN(Cc3cc(C4CC4)c(C4CC4)cc3OC(C)C)CC2)c1=O] | 465.2 |
| 29 | 1-(1-((2-chloro-6-cyclopropyl-4'-fluoro-3-methoxybiphenyl-4-yl)methyl)piperidin-4-yl)-2-oxo-1,2-dihydropyridine-4-carboxylic acid | 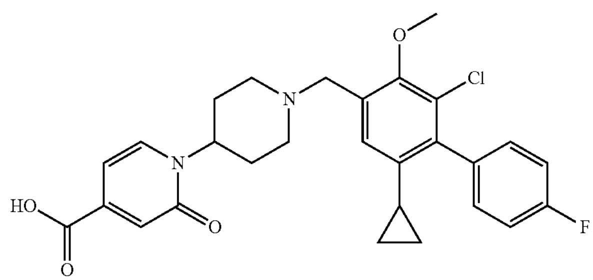 [SMILES: COc1c(CN2CCC(n3ccc(C(=O)O)cc3=O)CC2)cc(C2CC2)c(-c2ccc(F)cc2)c1Cl] | 511.1 |
| 30 | 1-(1-(4,5-dicyclopropyl-2-isopropoxybenzyl)piperidin-4-yl)-2-oxo-1,2-dihydropyridine-4-carboxamide | 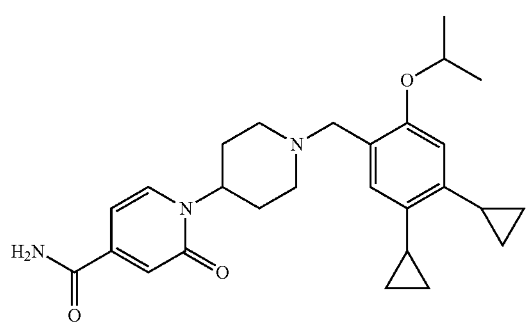 [SMILES: CC(C)Oc1cc(C2CC2)c(C2CC2)cc1CN1CCC(n2ccc(C(N)=O)cc2=O)CC1] | 450.2 |
| 31 | 1-(1-(4,5-dicyclopropyl-2-isopropoxybenzyl)piperidin-4-yl)-4-(1H-tetrazol-5-yl)pyridin-2(1H)-one | 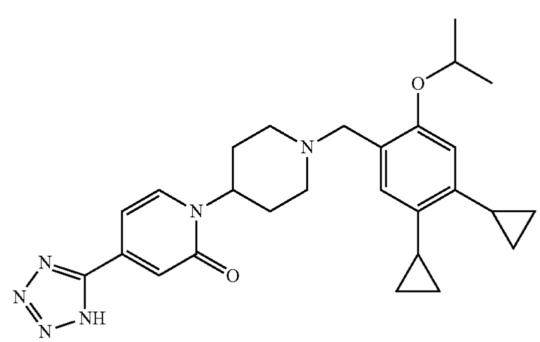 [SMILES: CC(C)Oc1cc(C2CC2)c(C2CC2)cc1CN1CCC(n2ccc(-c3nnn[nH]3)cc2=O)CC1] | 475.2 |

TABLE 1-continued

| Example # | IUPAC NAME | Structure | MS |
|---|---|---|---|
| 32 | ((1-(1-(4,5-dicyclopropyl-2-isopropoxybenzyl)piperidin-4-yl)-2-oxo-1,2-dihydropyridin-4-yl)oxy)acetic acid | 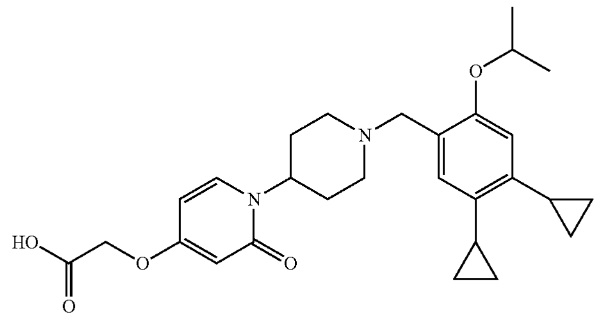 [SMILES: CC(C)Oc1cc(C2CC2)c(C2CC2)cc1CN1CCC(n2ccc(OCC(=O)O)cc2=O)CC1] | 481.1 |
| 33 | 1-(1-(4,5-dicyclopropyl-2-isopropoxybenzyl)piperidin-4-yl)-2-oxo-3-propyl-1,2-dihydropyridine-4-carboxylic acid | 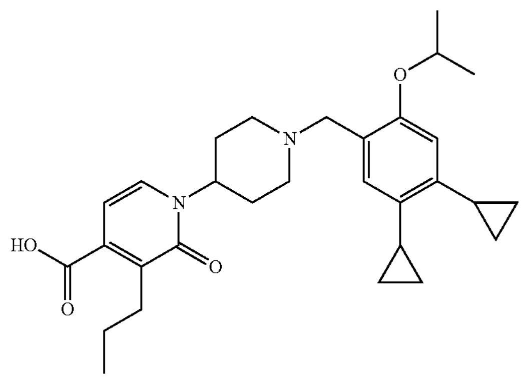 [SMILES: CCCc1c(C(=O)O)ccn(C2CCN(Cc3cc(C4CC4)c(C4CC4)cc3OC(C)C)CC2)c1=O] | 493.3 |
| 34 | 1-(1-(2-(cyclopentyloxy)-4,5-dicyclopropylbenzyl)piperidin-4-yl)-2-oxo-1,2-dihydropyridine-4-carboxylic acid | 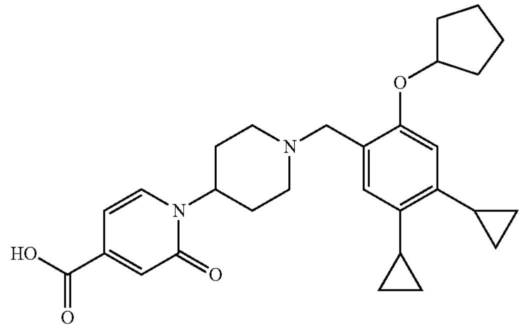 [SMILES: O=C(O)c1ccn(C2CCN(Cc3cc(C4CC4)c(C4CC4)cc3OC3CCCC3)CC2)c(=O)c1] | 477.2 |
| 35 | 1-(1-(4,5-dicyclopropyl-2-isopropoxybenzyl)piperidin-4-yl)-4-(5-oxo-4,5-dihydro-1,2,4-oxadiazol-3-yl)pyridin-2(1H)-one | 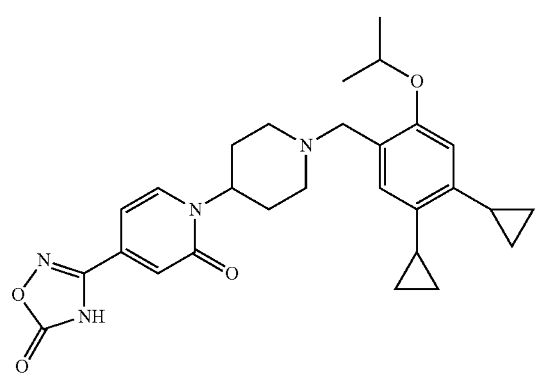 [SMILES: CC(C)Oc1cc(C2CC2)c(C2CC2)cc1CN1CCC(n2ccc(-c3noc(=O)[nH]3)cc2=O)CC1] | 491.2 |

TABLE 1-continued

| Example # | IUPAC NAME | Structure | MS |
|---|---|---|---|
| 36 | 1-(1-(3-chloro-4,5-dicyclopropyl-2-isopropoxybenzyl)piperidin-4-yl)-2-oxo-1,2-dihydropyridine-4-carboxylic acid | 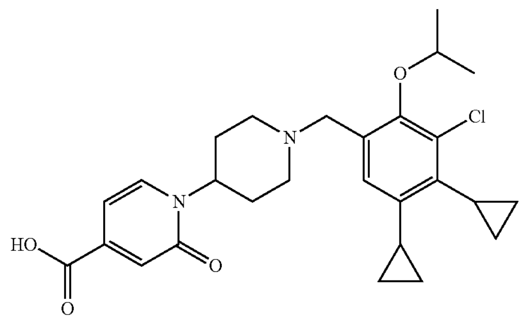 [SMILES: CC(C)Oc1c(CN2CCC(n3ccc(C(=O)O)cc3=O)CC2)cc(C2CC2)c(C2CC2)c1Cl] | 485.2 |
| 37 | 3-cyclopropyl-1-(1-((2-cyclopropyl-2',4'-difluoro-5-isopropoxybiphenyl-4-yl)methyl)piperidin-4-yl)-2-oxo-1,2-dihydropyridine-4-carboxylic acid | 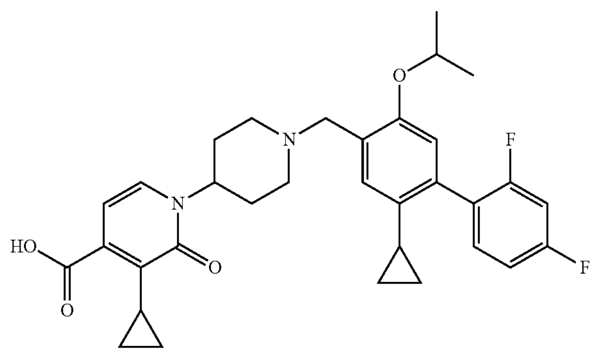 [SMILES: CC(C)Oc1cc(-c2ccc(F)cc2F)c(C2CC2)cc1CN1CCC(n2ccc(C(=O)O)c(C3CC3)c2=O)CC1] | 563.2 |
| 38 | 1-(1-((1-ethyl-5-isopropoxy-3-methyl-1H-indazol-6-yl)methyl)piperidin-4-yl)-2-oxo-1,2-dihydropyridine-4-carboxylic acid | 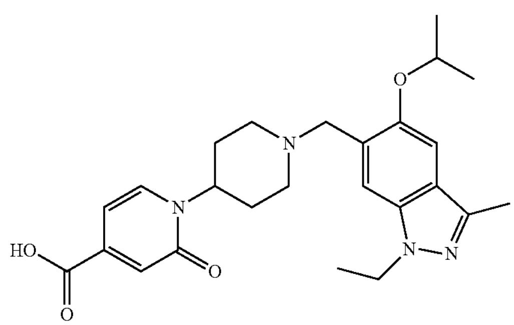 [SMILES: CCn1nc(C)c2cc(OC(C)C)c(CN3CCC(n4ccc(C(=O)O)cc4=O)CC3)cc21] | 453.2 |
| 39 | 1-(1-(3-chloro-4,5-dicyclopropyl-2-methoxybenzyl)piperidin-4-yl)-2-oxo-1,2-dihydropyridine-4-carboxylic acid | 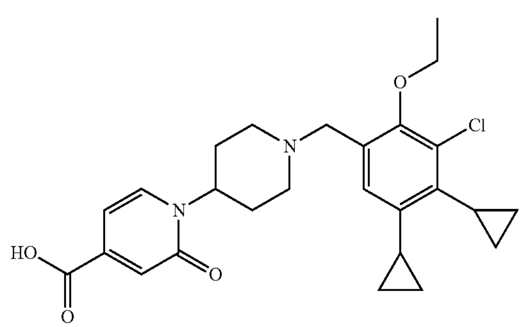 [SMILES: CCOc1c(CN2CCC(n3ccc(C(=O)O)cc3=O)CC2)cc(C2CC2)c(C2CC2)c1Cl] | 457.1 |

TABLE 1-continued

| Example # | IUPAC NAME | Structure | MS |
|---|---|---|---|
| 40 | 1-(1-(3-chloro-4,5-dicyclopropyl-2-ethoxybenzyl)piperidin-4-yl)-2-oxo-1,2-dihydropyridine-4-carboxylic acid | 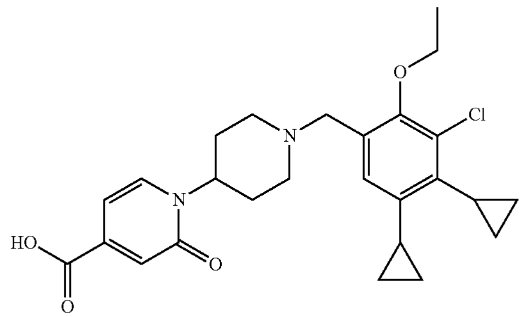 [SMILES: CCOc1c(CN2CCC(n3ccc(C(=O)O)cc3=O)CC2)cc(C2CC2)c(C2CC2)c1Cl] | 471.2 |
| 41 | 1-(1-((6-cyclopropyl-2',4'-difluoro-3-isopropoxy-2-methylbiphenyl-4-yl)methyl)piperidin-4-yl)-2-oxo-1,2-dihydropyridine-4-carboxylic acid | 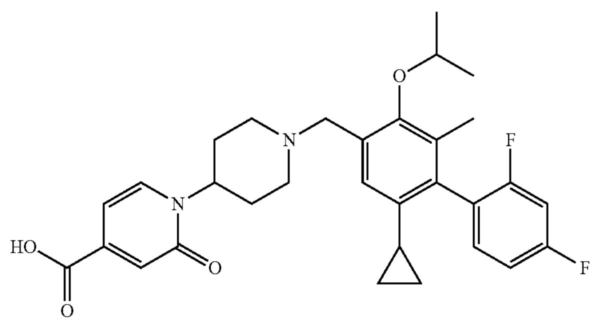 [SMILES: Cc1c(OC(C)C)c(CN2CCC(n3ccc(C(=O)O)cc3=O)CC2)cc(C2CC2)c1-c1ccc(F)cc1F] | 537.2 |
| 42 | 1-(1-((2-cyclopropyl-5-ethoxy-4'-fluorobiphenyl-4-yl)methyl)piperidin-4-yl)-6-oxo-1,6-dihydropyrimidine-4-carboxylic acid | 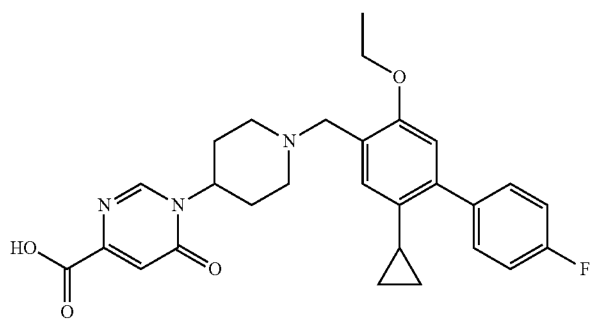 [SMILES: CCOc1cc(-c2ccc(F)cc2)c(C2CC2)cc1CN1CCC(n2cnc(C(=O)O)cc2=O)CC1] | 492.2 |
| 43 | 1-(1-((6-cyclopropyl-2,4'-difluoro-3-isopropoxybiphenyl-4-yl)methyl)piperidin-4-yl)-3-ethyl-2-oxo-1,2-dihydropyridine-4-carboxylic acid | 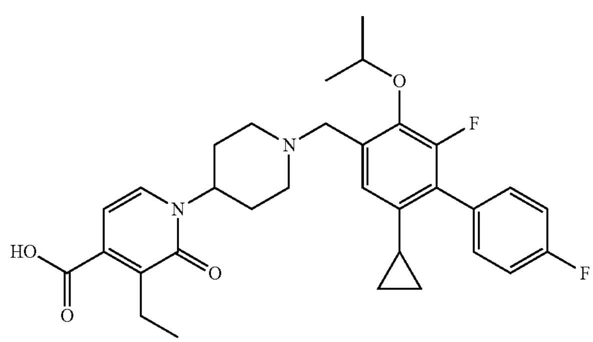 [SMILES: CCc1c(C(=O)O)ccn(C2CCN(Cc3cc(C4CC4)c(-c4ccc(F)cc4)c(F)c3OC(C)C)CC2)c1=O] | 551.2 |

TABLE 1-continued

| Example # | IUPAC NAME | Structure | MS |
|---|---|---|---|
| 44 | 1-(1-((6-cyclopropyl-3-ethoxy-2,4'-difluorobiphenyl-4-yl)methyl)piperidin-4-yl)-3-ethyl-2-oxo-1,2-dihydropyridine-4-carboxylic acid | 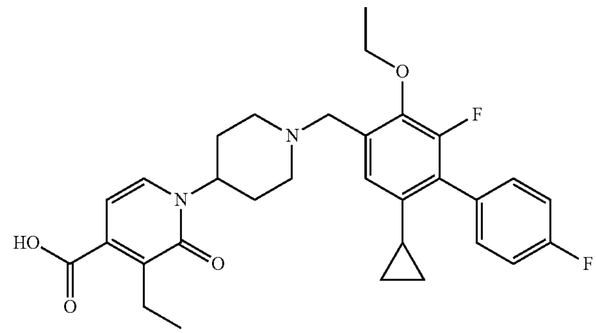 [SMILES: CCOc1c(CN2CCC(n3ccc(C(=O)O)c(CC)c3=O)CC2)cc(C2CC2)c(-c2ccc(F)cc2)c1F] | 537.2 |
| 45 | 1-(1-((6-cyclopropyl-3-ethoxy-2,2',4'-trifluorobiphenyl-4-yl)methyl)piperidin-4-yl)-3-ethyl-2-oxo-1,2-dihydropyridine-4-carboxylic acid | 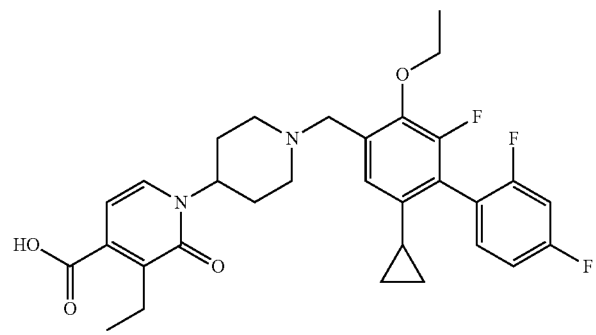 [SMILES: CCOc1c(CN2CCC(n3ccc(C(=O)O)c(CC)c3=O)CC2)cc(C2CC2)c(-c2ccc(F)cc2F)c1F] | 555.2 |
| 46 | 1-(1-((2-cyclopropyl-2',4'-difluoro-5-isopropoxybiphenyl-4-yl)methyl)piperidin-4-yl)-6-methyl-2-oxo-1,2-dihydropyridine-4-carboxylic acid | 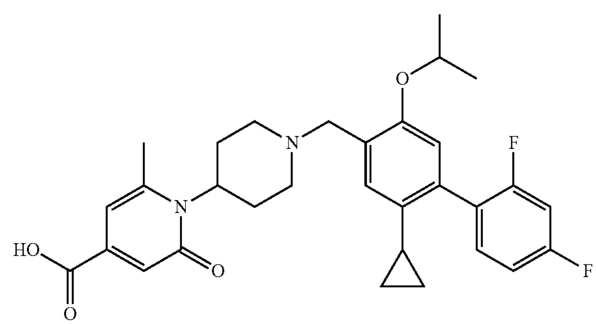 [SMILES: Cc1cc(C(=O)O)cc(=O)n1C1CCN(Cc2cc(C3CC3)c(-c3ccc(F)cc3F)cc2OC(C)C)CC1] | 537.3 |
| 47 | 1-(1-(4,5-dicyclopropyl-3-fluoro-2-isopropoxybenzyl)piperidin-4-yl)-3-ethyl-2-oxo-1,2-dihydropyridine-4-carboxylic acid | 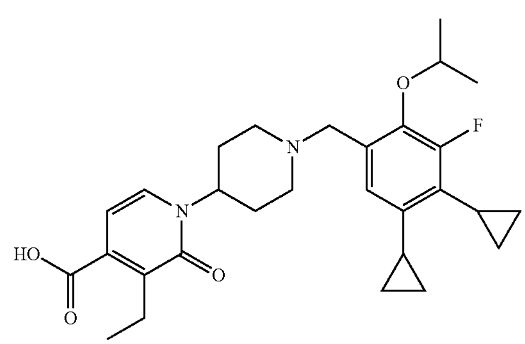 [SMILES: CCc1c(C(=O)O)ccn(C2CCN(Cc3cc(C4CC4)c(C4CC4)c(F)c3OC(C)C)CC2)c1=O] | 497.3 |

TABLE 1-continued

| Example # | IUPAC NAME | Structure | MS |
|---|---|---|---|
| 48 | 1-(1-(4,5-dicyclopropyl-2-ethoxy-3-fluorobenzyl)piperidin-4-yl)-3-ethyl-2-oxo-1,2-dihydropyridine-4-carboxylic acid | 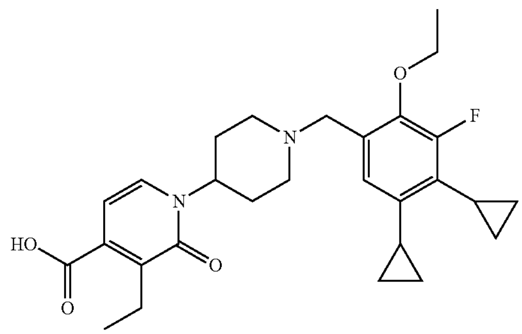 [SMILES: CCOc1c(CN2CCC(n3ccc(C(=O)O)c(CC)c3=O)CC2)cc(C2CC2)c(C2CC2)c1F] | 483.1 |
| 49 | 1-(1-((6-cyclopropyl-2,4'-difluoro-3-isopropylbiphenyl-4-yl)methyl)piperidin-4-yl)-3-methyl-2-oxo-1,2-dihydropyridine-4-carboxylic acid | 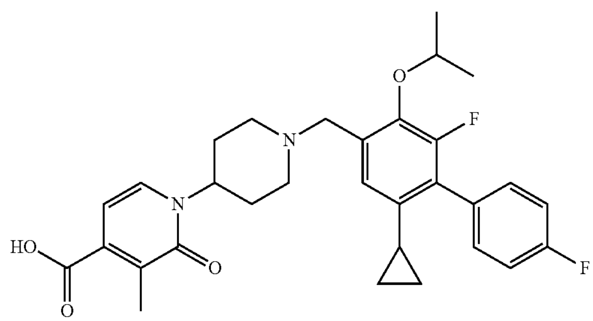 [SMILES: Cc1c(C(=O)O)ccn(C2CCN(Cc3cc(C4CC4)c(-c4ccc(F)cc4)c(F)c3OC(C)C)CC2)c1=O] | 537.2 |
| 50 | 1-(1-((6-cyclopropyl-3-ethoxy-2,4'-difluorobiphenyl-4-yl)methyl)piperidin-4-yl)-3-methyl-2-oxo-1,2-dihydropyridine-4-carboxylic acid | 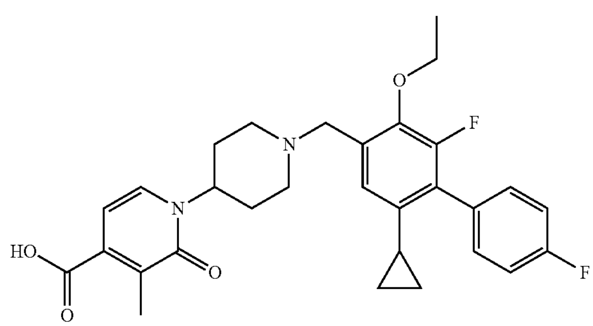 [SMILES: CCOc1c(CN2CCC(n3ccc(C(=O)O)c(C)c3=O)CC2)cc(C2CC2)c(-c2ccc(F)cc2)c1F] | 523.1 |
| 51 | 1-(1-((2-cyclopropyl-4'-fluoro-5-isopropoxybiphenyl-4-yl)methyl)piperidin-4-yl)-3-ethyl-2-oxo-1,2-dihydropyridine-4-carboxylic acid | 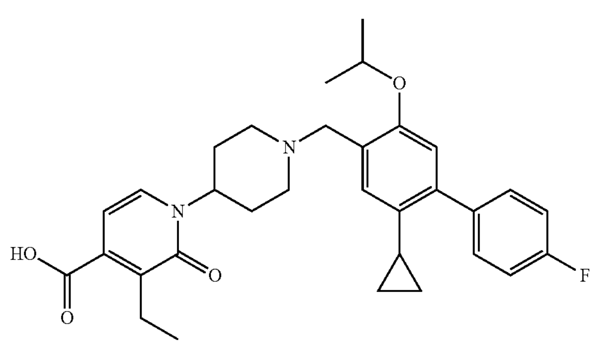 [SMILES: CCc1c(C(=O)O)ccn(C2CCN(Cc3cc(C4CC4)c(-c4ccc(F)cc4)cc3OC(C)C)CC2)c1=O] | 533.2 |

TABLE 1-continued

| Example # | IUPAC NAME | Structure | MS |
|---|---|---|---|
| 52 | 1-(1-((6-cyclopropyl-2,4'-difluoro-3-isopropoxybiphenyl-4-yl)methyl)piperidin-4-yl)-2-oxo-1,2-dihydropyridine-4-carboxylic acid | 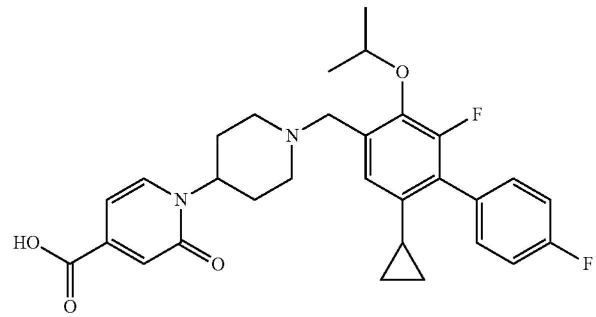 [SMILES: CC(C)Oc1c(CN2CCC(n3ccc(C(=O)O)cc3=O)CC2)cc(C2CC2)c(-c2ccc(F)cc2)c1F] | 523.1 |
| 53 | 1-(1-((6-cyclopropyl-2,4'-difluoro-3-methoxybiphenyl-4-yl)methyl)piperidin-4-yl)-3-methyl-2-oxo-1,2-dihydropyridine-4-carboxylic acid | 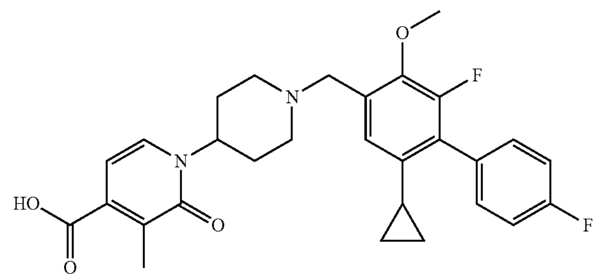 [SMILES: COc1c(CN2CCC(n3ccc(C(=O)O)c(C)c3=O)CC2)cc(C2CC2)c(-c2ccc(F)cc2)c1F] | 509.2 |
| 54 | 1-(1-((6-cyclopropyl-2,4'-difluoro-3-methoxybiphenyl-4-yl)methyl)piperidin-4-yl)-3-ethyl-2-oxo-1,2-dihydropyridine-4-carboxylic acid | 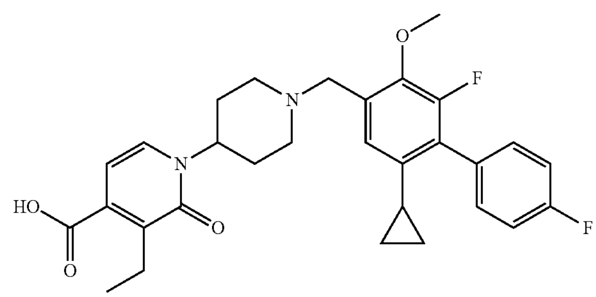 [SMILES: CCc1c(C(=O)O)ccn(C2CCN(Cc3cc(C4CC4)c(-c4ccc(F)cc4)c(F)c3OC)CC2)c1=O] | 523.1 |
| 55 | 1-(1-((6-chloro-2,4'-difluoro-3-isopropoxybiphenyl-4-yl)methyl)piperidin-4-yl)-3-ethyl-2-oxo-1,2-dihydropyridine-4-carboxylic acid | 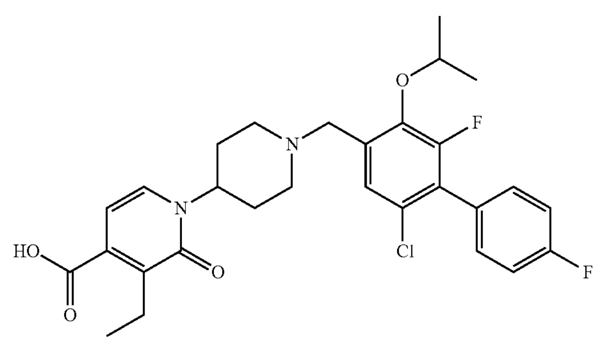 [SMILES: CCc1c(C(=O)O)ccn(C2CCN(Cc3cc(Cl)c(-c4ccc(F)cc4)c(F)c3OC(C)C)CC2)c1=O] | 545.0 |
| 56 | 1-(1-((2-chloro-6-cyclopropyl-4'-fluoro-3-isopropoxybiphenyl-4-yl)methyl)piperidin-4-yl)-3-ethyl-2-oxo-1,2-dihydropyridine-4-carboxylic acid | 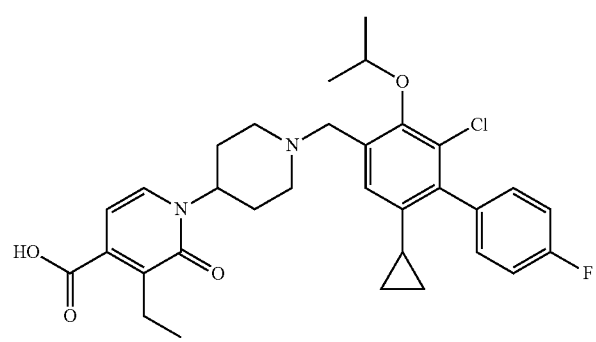 [SMILES: CCc1c(C(=O)O)ccn(C2CCN(Cc3cc(C4CC4)c(-c4ccc(F)cc4)c(Cl)c3OC(C)C)CC2)c1=O] | 567.1 |

TABLE 1-continued

| Example # | IUPAC NAME | Structure | MS |
|---|---|---|---|
| 57 | 1-(1-((6-cyclopropyl-4'-fluoro-3-isopropoxy-2-methylbiphenyl-4-yl)methyl)piperidin-4-yl)-3-ethyl-2-oxo-1,2-dihydropyridine-4-carboxylic acid | 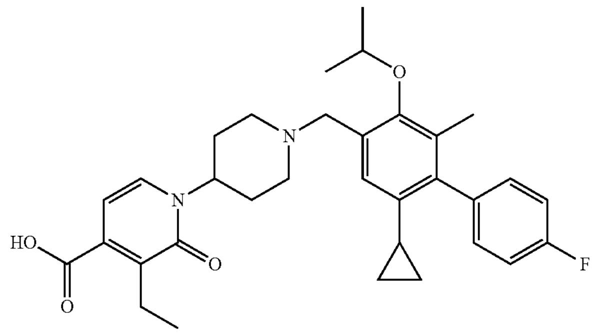 [SMILES: CCc1c(C(=O)O)ccn(C2CCN(Cc3cc(C4CC4)c(-c4ccc(F)cc4)c(C)c3OC(C)C)CC2)c1=O] | 547.2 |
| 58 | 1-(1-(4,5-dicyclopropyl-2-isopropoxybenzyl)piperidin-4-yl)-3-ethyl-2-oxo-1,2-dihydropyridine-4-carboxylic acid | 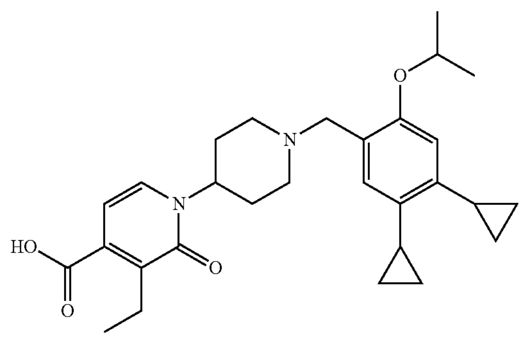 [SMILES: CCc1c(C(=O)O)ccn(C2CCN(Cc3cc(C4CC4)c(C4CC4)cc3OC(C)C)CC2)c1=O] | 479.1 |
| 59 | 1-(1-(4,5-dicyclopropyl-2-isopropoxybenzyl)piperidin-4-yl)-6-methyl-2-oxo-1,2-dihydropyridine-4-carboxylic acid | 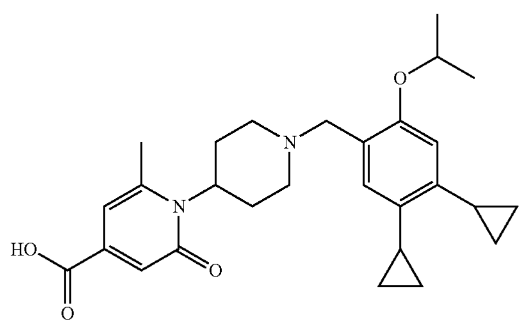 [SMILES: Cc1cc(C(=O)O)cc(=O)n1C1CCN(Cc2cc(C3CC3)c(C3CC3)cc2OC(C)C)CC1] | 465.1 |
| 60 | 1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylic acid hydrochloride | 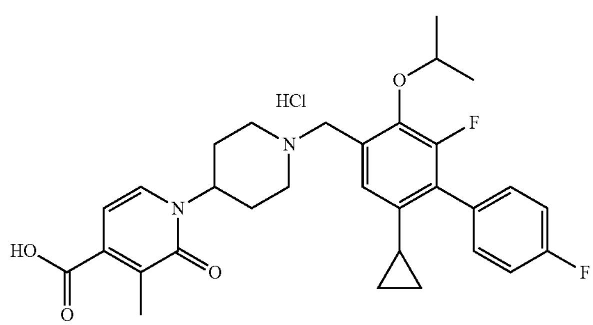 [SMILES: Cc1c(C(=O)O)ccn(C2CCN(Cc3cc(C4CC4)c(-c4ccc(F)cc4)c(F)c3OC(C)C)CC2)c1=O ; Cl] | 537.1 |

TABLE 1-continued

| Example # | IUPAC NAME | Structure | MS |
|---|---|---|---|
| 61 | 1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylic acid 1/2 hydrosulfate | 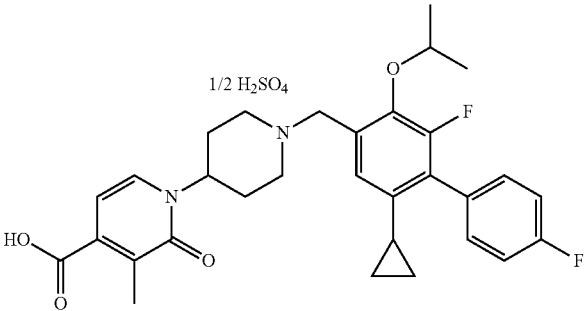 [SMILES: Cc1c(C(=O)O)ccn(C2CCN(Cc3cc(C4CC4)c(-c4ccc(F)cc4)c(F)c3OC(C)C)CC2)c1=O] | 537.1 |
| 62 | 1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylic acid maleate | 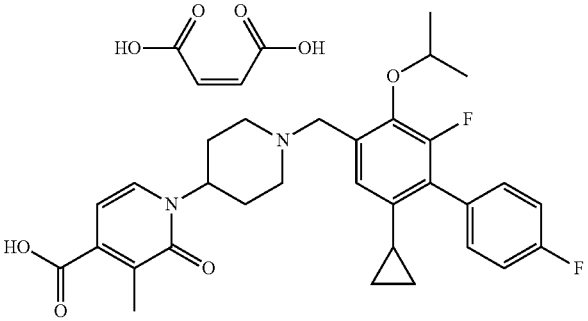 | 537.2 |

Test Example 1

Evaluation of Human SSTR5 Antagonist Activity Using Intracellular cAMP Concentration as Index The intracellular cAMP concentration was measured using HTRF cAMP dynamic 2 kit (Cisbio Bioassays). Each test compound diluted with an assay buffer (HBSS (Invitrogen Corp.) containing 5 mM HEPES (pH 7.5) (Invitrogen Corp.), 0.1% fatty-acid free BSA (Sigma-Aldrich Corp.), and 500 u ("u" represents "micro")M IBMX (Wako Pure Chemical Industries, Ltd.)) was added at a concentration of 2 uL/well to a 384-well white plate (Greiner Bio-One Co., Ltd.) to give the final concentration of 1 uM. A frozen stock of CHO (dhfr−) cells stably expressing the human SSTR5 gene (Accession No. NM_001053) was thawed in a thermostat bath of 37 C and suspended in a subculture medium (MEM alpha (Wako Pure Chemical Industries, Ltd.), 10% dialyzed serum (Gemini Bio-Products), and 50 ug/mL gentamicin (Invitrogen Corp.). After centrifugation of the cell suspension, the cells were resuspended in an assay buffer and added at a concentration of 2 uL/well (about 4,000 cells/well) to the plate. The compound and the cells were incubated for 15 minutes, and then, an assay buffer containing 0.1 nM (final concentration) somatostatin 28 (Toray Research Center) and 0.3 uM (final concentration) forskolin (Wako Pure Chemical Industries, Ltd.) was added thereto at a concentration of 2 uL/well, followed by incubation at room temperature for 30 minutes. cAMP-d2 and anti-cAMP-cryptate were each added thereto at a concentration of 3 uL/well. The plate was left standing at room temperature for 60 minutes. Then, the fluorescence resonance energy transfer (FRET) intensity was measured using Multi-label reader Envision (PerkinElmer). The FRET intensity of the wells supplemented with the test compound group was converted to a cAMP concentration using a calibration curve prepared from the FRET intensity of a well group containing an assay buffer supplemented with an arbitrary concentration of cAMP. The inhibitory activity of each compound was calculated according to the following expression:

Inhibitory activity(%)=(C−B)/(A−B)×100

A: cAMP concentration calculated from the wells supplemented with 0.3 uM forskolin
B: cAMP concentration calculated from the wells supplemented with 0.3 uM forskolin and 0.1 nM somatostatin 28
C: cAMP concentration calculated from the wells supplemented with 0.3 uM forskolin, 0.1 nM somatostatin 28, and 1 uM test compound Table 2 shows the inhibition rate (%) against SSTR5 at the concentration 1 uM of the test compound.

TABLE 2

| Example No. | Inhibition rate against SSTR5 at 1 uM |
|---|---|
| 1 | 84 |
| 2 | 134 |
| 3 | 116 |
| 4 | 120 |
| 5 | 88 |
| 6 | 94 |
| 7 | 124 |
| 43 | 133 |
| 44 | 87 |
| 45 | 98 |
| 47 | 111 |
| 49 | 99 |
| 50 | 87 |
| 51 | 89 |

As is evident from Table 2, the compound of the present invention exhibited a superior SSTR5 antagonist action.

Test Example 2

Antidiabetic Effect in Mice

Female KK-Ay/Ta mice (Clea Japan Inc.), a type 2 diabetes model, were used in this study. At the age of 7-week old, blood sample were collected from tail vein at 8:00 am, and animals were divided into separate groups (n=8) based on glycated hemoglobin (GHb), plasma glucose, insulin, triglyceride levels and body weight. Vehicle (0.5% (w/v) methylcellulose) or compounds (suspended in vehicle) were orally administered once a day for 2 weeks. After 2 weeks of treatment, GHb was determined by auto-analyzer HLC-723G8 (TOSOH, Japan).

TABLE 3

| group | average of delta GHb (%) |
|---|---|
| vehicle | −0.06 |
| Example 49 (1 mg/kg) | −0.51 |

Formulation Example 1

Production of Capsule

| | |
|---|---|
| 1) Compound of Example 1 | 30 mg |
| 2) Fine cellulose powder | 10 mg |
| 3) Lactose | 19 mg |
| 4) Magnesium stearate | 1 mg |
| Total: | 60 mg |

Ingredients 1), 2), 3), and 4) are mixed and filled in a gelatin capsule shell.

Formulation Example 2

Production of Tablet

| | |
|---|---|
| 1) Compound of Example 1 | 30 g |
| 2) Lactose | 50 g |
| 3) Corn starch | 15 g |
| 4) Carboxymethylcellulose calcium | 44 g |
| 5) Magnesium stearate | 1 g |
| Total of 1000 tablets: | 140 g |

The whole amounts of ingredients 1), 2), and 3) and 30 g of ingredient 4) are kneaded with water and granulated after vacuum drying. The granulated powders are mixed with 14 g of ingredient 4) and 1 g of ingredient 5). The mixture is compressed using a tableting machine. In this way, 1000 tablets each containing 30 mg of the compound of Example 1 are obtained.

INDUSTRIAL APPLICABILITY

The compound of the present invention has a somatostatin receptor subtype 5 antagonist action and is useful in the prophylaxis or treatment of diabetes mellitus, obesity, and the like.

All the publications, patents, and the patent applications cited herein are incorporated herein by reference in their entireties.

The invention claimed is:

1. A compound
selected from the group consisting of
1-(1-((2-cyclopropyl-4'-fluoro-5-isopropoxybiphenyl-4-yl)methyl)piperidin-4-yl)-2-oxo-1,2-dihydropyridine-4-carboxylic acid,
1-(1-((6-cyclopropyl-2,4'-difluoro-3-isopropoxybiphenyl-4-yl)methyl)piperidin-4-yl)-3-ethyl-2-oxo-1,2-dihydropyridine-4-carboxylic acid, and
1-(1-((6-cyclopropyl-2,4'-difluoro-3-isopropoxybiphenyl-4-yl)methyl)piperidin-4-yl)-3-methyl-2-oxo-1,2-dihydropyridine-4-carboxylic acid, or a salt thereof.

2. 1-(1-((2-Cyclopropyl-4'-fluoro-5-isopropoxybiphenyl-4-yl)methyl)piperidin-4-yl)-2-oxo-1,2-dihydropyridin-4-carboxylic acid or a salt thereof.

3. 1-(1-((6-Cyclopropyl-2,4'-difluoro-3-isopropoxybiphenyl-4-yl)methyl)piperidin-4-yl)-3-ethyl-2-oxo-1,2-dihydropyridine-4-carboxylic acid or a salt thereof.

4. 1-(1-((6-Cyclopropyl-2,4'-difluoro-3-isopropoxybiphenyl-4-yl)methyl)piperidin-4-yl)-3-methyl-2-oxo-1,2-dihydropyridine-4-carboxylic acid or a salt thereof.

5. A medicament comprising the compound of claim 1 or a salt thereof.

6. The medicament of claim 5, which is a somatostatin receptor 5 antagonist.

7. The medicament of claim 5, which is an agent for the treatment of diabetes mellitus.

8. A method for treating diabetes mellitus in a mammal, comprising administering to the mammal an effective amount of the compound according to claim 1 or a salt thereof.

9. A method for antagonizing somatostatin receptor subtype 5 in a mammal, comprising administering to the mammal an effective amount of the compound according to claim 1 or a salt thereof.

10. The compound according to claim 1 or a salt thereof for the treatment of diabetes mellitus.

* * * * *